US008389730B2

(12) United States Patent
Natarajan et al.

(10) Patent No.: US 8,389,730 B2
(45) Date of Patent: Mar. 5, 2013

(54) COMPOSITIONS AND METHODS FOR THE TREATMENT OF DISEASE ASSOCIATED WITH TRP-P8 EXPRESSION

(75) Inventors: Sateesh K. Natarajan, Bellevue, WA (US); Ofir Moreno, Seattle, WA (US); Thomas J. Graddis, Seattle, WA (US); David F. Duncan, San Diego, CA (US); Reiner Laus, Bellevue, WA (US); Feng Chen, Seattle, WA (US)

(73) Assignee: Dendreon Corporation, Seattle, WA (US)

( * ) Notice: Subject to any disclaimer, the term of this patent is extended or adjusted under 35 U.S.C. 154(b) by 0 days.

(21) Appl. No.: 13/115,893

(22) Filed: May 25, 2011

(65) Prior Publication Data

US 2012/0094977 A1    Apr. 19, 2012

Related U.S. Application Data

(63) Continuation of application No. 10/923,413, filed on Aug. 20, 2004.

(60) Provisional application No. 60/497,384, filed on Aug. 22, 2003.

(51) Int. Cl.
*A61K 31/445* (2006.01)
*C07D 211/30* (2006.01)

(52) U.S. Cl. .................... 546/225; 514/330

(58) Field of Classification Search .............. None
See application file for complete search history.

(56) References Cited

U.S. PATENT DOCUMENTS

| 3,821,221 | A | 6/1974 | Podesva et al. |
| 4,020,153 | A | 4/1977 | Rowsell et al. |
| 4,150,052 | A | 4/1979 | Watson et al. |
| 4,153,679 | A | 5/1979 | Rowsell et al. |
| 4,248,859 | A | 2/1981 | Rowsell et al. |
| 4,296,093 | A | 10/1981 | Rowsell et al. |
| 4,459,425 | A | 7/1984 | Amano et al. |
| 5,266,592 | A | 11/1993 | Grub et al. |
| 5,756,857 | A | 5/1998 | Kuribayashi et al. |
| 6,328,982 | B1 | 12/2001 | Shiroyama et al. |
| 6,497,859 | B1 | 12/2002 | Zanone et al. |
| 2004/0001801 | A1 | 1/2004 | Madison et al. |
| 2005/0090514 | A1 | 4/2005 | Reynolds et al. |
| 2007/0232603 | A1 | 10/2007 | Moreno et al. |

FOREIGN PATENT DOCUMENTS

| CA | 2530884 | | 1/2005 |
| EP | 1 121 927 | A2 | 8/2001 |
| EP | 1 121 927 | A3 | 8/2001 |
| EP | 1 157 617 | A2 | 11/2001 |
| JP | 47-16647 | | 10/1972 |
| JP | 47-16648 | | 10/1972 |
| JP | 2000 247910 | A | 9/2000 |
| WO | WO 93/23005 | A1 | 11/1993 |
| WO | WO 93/25177 | A1 | 12/1993 |
| WO | WO 02/095007 | A2 | 11/2002 |
| WO | WO 2005/002582 | A2 | 1/2005 |
| WO | WO 2005/002582 | A3 | 1/2005 |

OTHER PUBLICATIONS

Bardyshev, I.I. et al., "Synthesis and Pesticide Activity if some amino Derivatives of Terpenoids," *Vetsi Akademii Navuk BSSR, Seryya Khimichnykh Navuk*, vol. 4, pp. 89-91 (1984)—Abstract.
Clapham, David E. et al., "The TRP Ion Channel Family," *Nature Reviews Neuroscience*, vol. 2, No. 6, pp. 387-396 (Feb. 2002).
Clapham, D.E., "Hot and Cold TRP Ion Channels," *Science*, Mar. 22, 2002, vol. 295, pp. 2228-2229.
Duncan, Lyn M. et al., "Down-Regulation of the Novel Gene *Malastatin* Correlates with Potential for Melanoma Metastasis," *Cancer Research*, vol. 58, pp. 1515-1520 (Apr. 1998).
Fuessel, Susanne et al., "Multiple Tumor Marker Analyses (PSA, hK2, PSCA, Trp-p8) In Primary Prostate Cancers Using Quantitative RT-PCR," *Int'l Journal of Oncology*, vol. 23, No. 1, pp. 221-228 (Jul. 2003).
Hofmann et al., "Transient receptor potential channels as molecular substrates of receptor-mediated cation entry," *J. Mol. Med.*, (2000), 78:14-25.
Hunter, John J. et al., "Chromosonal Localization and Genomic Characterization of the Mouse Melastatin Gene (Mlsn1)," *Genomics*, vol. 54, No. 1, pp. 116-123 (Nov. 1998).
Kozolov, N.G. et al., "Reduction Amination of -Menthol by Aliphatic Nitriles," *Khimiya Prisrodnykh Soedinenii*, vol. 3, pp. 312-317 (1981)—Abstract.
McKemy, David D. et al., "Identification of Cold Receptor Reveals a General Role for TRP Channels in Thermosensation," *Nature*, vol. 416, No. 6876, pp. 52-58 (Mar. 2002).
Nagamine, Kentaro et al., "Molecular Cloning of a Novel Putative $CA^{2+}$ Channel Protein (TRPC7) Highly Expressed in Brain," *Genomics*, vol. 54, No. 1, pp. 124-131 (Nov. 1998).
Nealen, M.L., et al., "TRPM8 mRNA is Expressed in a Subset of Cold-Responsive Trigeminal Neurons form Rat," *J. Neurophysiol*, Mar. 12, 2003, vol. 90, pp. 515-520.
Peier, Andrea M. et al., "A TRP Channel That Senses Cold Stimuli and Menthol," *Cell*, vol. 108, pp. 705-715 (Mar. 2002).
Reid, Gordon, "A Cold- and Menthol-Activated Curent in Rat Dorsal Root Ganglion Neurones: Properties and Role in Cold Transduction," *The Journal of Physiology*, vol. 545.2, pp. 595-614 (2002).

(Continued)

*Primary Examiner* — Janet Andres
*Assistant Examiner* — Heidi Reese
(74) *Attorney, Agent, or Firm* — Kilpatrick Townsend and Stockton LLP

(57) ABSTRACT

Provided are small-molecule Trp-p8 modulators, including Trp-p8 agonists and Trp-p8 antagonists, and compositions comprising small-molecule Trp-p8 agonists as well as methods for identifying and characterizing novel small-molecule Trp-p8 modulators and methods for decreasing viability and/or inhibiting growth of Trp-p8 expressing cells, methods for activating Trp-p8-mediated cation influx, methods for stimulating apoptosis and/or necrosis, and related methods for the treatment of diseases, including cancers such as lung, breast, colon, and/or prostate cancers as well as other diseases, such as benign prostatic hyperplasia, that are associated with Trp-p8 expression.

5 Claims, 7 Drawing Sheets

OTHER PUBLICATIONS

Tsavaler, Larisa et al., "*Trp-p8* A Novel Prostate-Specific Gene, Is Up-Regulated in Prostate Cancer and Other Malignancies and Shares High Homology With Transient Receptor Potential Calcium Channel Proteins," *Cancer Research*, vol. 61, pp. 3760-3769 (2001).

Voisin, Daniel, et al., "Stereochemical Studies. X. Solvent Effects on the Optical Activity of Conformers and on Conformational Equilibrium," *Bulletin de la Societe Chimique de France*, vol. 7, pp. 2643-2651 (1971)—Abstract.

Chemical Abstracts, (1985), vol. 102, abstract No. 24839.

Chemical Abstracts, (1981), vol. 95, abstract No. 220155.

Chemical Abstracts, (1971), vol. 75, abstract No. 110429.

SEQUENCE LISTING

```
<160> NUMBER OF SEQ ID NOS: 2

<210> SEQ ID NO 1
<211> LENGTH: 5674
<212> TYPE: DNA
<213> ORGANISM: Human

<400> SEQUENCE: 1
aagaaaatcc tgcttgacaa aaaccgtcac ttaggaaaag atgtcctttc gggcagccag      60
gctcagcatg aggaacagaa ggaatgacac tctggacagc acccggaccc tgtactccag     120
cgcgtctcgg agcacagact tgtcttacag tgaaagcgac ttggtgaatt ttattcaagc     180
aaattttaag aaacgagaat gtgtcttctt tatcaaagat tccaaggcca cggagaatgt     240
gtgcaagtgt ggctatgccc agagccagca catggaaggc acccagatca accaaagtga     300
gaaatggaac tacaagaaac acaccaagga atttcctacc gacgcctttg gggatattca     360
gtttgagaca ctggggaaga aagggaagta tatacgtctg tcctgcgaca cggacgcgga     420
aatcctttac gagctgctga cccagcactg gcacctgaaa acacccaacc tggtcatttc     480
tgtgaccggg ggcgccaaga acttcgccct gaagccgcgc atgcgcaaga tcttcagccg     540
gctcatctac atcgcgcagt ccaaaggtgc ttggattctc acgggaggca cccattatgg     600
cctgatgaag tacatcgggg aggtggtgag agataacacc atcagcagga gttcagagga     660
gaatattgtg gccattggca tagcagcttg gggcatggtc tccaaccggg acaccctcat     720
caggaattgc gatgctgagg gctattttt agcccagtac cttatggatg acttcacaag     780
agatccactg tatatcctgg acaacaacca cacacatttg ctgctcgtgg acaatggctg     840
tcatggacat cccactgtcg aagcaaagct ccggaatcag ctagagaagt atatctctga     900
gcgcactatt caagattcca actatggtgg caagatcccc attgtgtgtt ttgcccaagg     960
aggtggaaaa gagactttga aagccatcaa tacctccatc aaaaataaaa ttccttgtgt    1020
```

| | |
|---|---|
| ggtggtggaa ggctcgggcc agatcgctga tgtgatcgct agcctggtgg aggtggagga | 1080 |
| tgccctgaca tcttctgccg tcaaggagaa gctggtgcgc ttttttacccc gcacggtgtc | 1140 |
| ccggctgcct gaggaggaga ctgagagttg atcaaatgg ctcaaagaaa ttctcgaatg | 1200 |
| ttctcaccta ttaacagtta ttaaaatgga agaagctggg gatgaaattg tgagcaatgc | 1260 |
| catctcctac gctctataca aagccttcag caccagtgag caagacaagg ataactggaa | 1320 |
| tgggcagctg aagcttctgc tggagtgaa ccagctggac ttagccaatg atgagatttt | 1380 |
| caccaatgac cgccgatggg agtctgctga ccttcaagaa gtcatgttta cggctctcat | 1440 |
| aaaggacaga cccaagtttg tccgcctctt tctggagaat ggcttgaacc tacgaagtt | 1500 |
| tctcacccat gatgtcctca ctgaactctt ctccaaccac ttcagcacgc ttgtgtaccg | 1560 |
| gaatctgcag atcgccaaga attcctataa tgatgccctc ctcacgtttg tctggaaact | 1620 |
| ggttgcgaac ttccgaagag gcttccggaa ggaagacaga aatggccggg acgagatgga | 1680 |
| catagaactc cacgacgtgt ctcctattac tcggcacccc ctgcaagctc tcttcatctg | 1740 |
| ggccattctt cagaataaga aggaactctc caaagtcatt tgggagcaga ccaggggctg | 1800 |
| cactctggca gccctgggag ccagcaagct tctgaagact ctggccaaag tgaagaacga | 1860 |
| catcaatgct gctggggagt ccgaggagct ggctaatgag tacgagaccc gggctgttga | 1920 |
| gctgttcact gagtgttaca gcagcgatga agacttggca gaacagctgc tggtctattc | 1980 |
| ctgtgaagct tggggtggaa gcaactgtct ggagctggcg gtggaggcca cagaccagca | 2040 |
| tttcatcgcc cagcctgggg tccagaattt tcttttctaag caatggtatg gagagatttc | 2100 |
| ccgagacacc aagaactgga agattatcct gtgtctgttt attatacccct tggtgggctg | 2160 |
| tggctttgta tcatttagga agaaacctgt cgacaagcac aagaagctgc tttggtacta | 2220 |
| tgtggcgttc ttcacctccc ccttcgtggt cttctcctgg aatgtggtct tctacatcgc | 2280 |
| cttcctcctg ctgtttgcct acgtgctgct catggatttc cattcggtgc cacacccccc | 2340 |
| cgagctggtc ctgtactcgc tggtcttgt cctcttctgt gatgaagtga cagtggta | 2400 |
| cgtaaatggg gtgaattatt ttactgacct gtgaatgtg atggacacgc tgggctttt | 2460 |
| ttacttcata gcaggaattg tatttcggct ccactcttct aataaaagct ctttgtattc | 2520 |
| tggacgagtc attttctgtc tggactacat tattttcact ctaagattga tccacatttt | 2580 |
| tactgtaagc agaaacttag gacccaagat tataatgctg cagaggatgc tgatcgatgt | 2640 |
| gttcttcttc ctgttcctct ttgcggtgtg gatggtggcc tttggcgtgg ccaggcaagg | 2700 |
| gatccttagg cagaatgagc agcgctggag gtggatattc cgttcggtca tctacgagcc | 2760 |
| ctacctggcc atgttcggcc aggtgcccag tgacgtggat ggtaccacgt atgactttgc | 2820 |
| ccactgcacc ttcactggga atgagtccaa gccactgtgt gtggagctgg atgagcacaa | 2880 |
| cctgccccgg ttccccgagt ggatcaccat cccctggtg tgcatctaca tgttatccac | 2940 |
| caacatcctg ctggtcaacc tgctggtcgc catgtttggc tacacggtgg gcaccgtcca | 3000 |
| ggagaacaat gaccaggtct ggaagttcca gaggtacttc ctggtgcagg agtactgcag | 3060 |
| ccgcctcaat atcccttcc ccttcatcgt cttcgcttac ttctacatgg tggtgaagaa | 3120 |
| gtgcttcaag tgttgctgca aggagaaaaa catggagtct tctgtctgct gtttcaaaaa | 3180 |
| tgaagacaat gagactctgg catgggaggg tgtcatgaag gaaaactacc ttgtcaagat | 3240 |
| caacacaaaa gccaacgaca cctcagagga aatgaggcat cgatttagac aactggatac | 3300 |
| aaagcttaat gatctcaagg gtcttctgaa agagattgct aataaatca ataaaatca | 3360 |
| aataaaactg tatgaaactc taatggagaa aaatctaatt atagcaagat catattaagg | 3420 |

```
aatgctgatg aacaattttg ctatcgacta ctaaatgaga gattttcaga cccctgggta    3480
catggtggat gattttaaat caccctagtg tgctgagacc ttgagaataa agtgtgtgat    3540
tggtttcata cttgaagacg gatataaagg aagaatattt cctttatgtg tttctccaga    3600
atggtgcctg tttctctctg tgtctcaatg cctgggactg gaggttgata gtttaagtgt    3660
gttcttaccg cctcctttt cctttaatct tattttgat gaacacatat ataggagaac    3720
atctatccta tgaataagaa cctggtcatg ctttactcct gtattgttat tttgttcatt    3780
tccaattgat tctctacttt tccctttttt gtattatgtg actaattagt tggcatattg    3840
ttaaaagtct ctcaaattag gccagattct aaaacatgct gcagcaagag gaccccgctc    3900
tcttcaggaa aagtgttttc atttctcagg atgcttctta cctgtcagag gaggtgacaa    3960
ggcagtctct tgctctcttg gactcaccag gctcctattg aaggaaccac ccccattcct    4020
aaatatgtga aaagtcgccc aaaatgcaac cttgaaaggc actactgact ttgttcttat    4080
tggatactcc tcttatttat tatttttcca ttaaaaataa tagctggcta ttatagaaaa    4140
tttagaccat acagagatgt agaaagaaca taaattgtcc ccattacctt aaggtaatca    4200
ctgctaacaa tttctggatg ttttttcaag tctattttt ttctatgtat gtctcaattc    4260
tctttcaaaa ttttacagaa tgttatcata ctacatatat acttttatg taagcttttt    4320
cacttagtat tttatcaaat atgttttttat tatattcata gccttcttaa acattatatc    4380
aataattgca taataggcaa cctctagcga ttaccataat tttgctcatt gaaggctatc    4440
tccagttgat cattgggatg agcatctttg tgcatgaatc ctattgctgt atttgggaaa    4500
attttccaag gttagattcc aataaatatc tatttattat taaatattaa aatatcgatt    4560
tattattaaa accatttata aggcttttc ataaatgtat agcaaatagg aattattaac    4620
ttgagcataa gatatgagat acatgaacct gaactattaa aataaaatat tatatttaac    4680
cctagtttaa gaagaagtca atatgcttat ttaaatatta tggatggtgg gcagatcact    4740
tgaggtcagg agttcgagac cagcctggcc aacatggcaa aaccacatct ctactaaaaa    4800
taaaaaaatt agctgggtgt ggtggtgcac tcctgtaatc ccagctactc agaaggctga    4860
ggtacaagaa ttgctggaac ctgggaggcg gaggttgcag tgaaccaaga ttgcaccact    4920
gcactccagc cggggtgaca gagtgagact ccgactgaaa ataaataaat aaataaataa    4980
ataaataaat aaataaatat tatggatggt gaagggaatg gtatagaatt ggagagatta    5040
tcttactgaa cacctgtagt cccagctttc tctggaagtg gtggtatttg agcaggatgt    5100
gcacaaggca attgaaatgc ccataattag tttctcagct ttgaatacac tataaactca    5160
gtggctgaag gaggaaattt tagaaggaag ctactaaaag atctaatttg aaaaactaca    5220
aaagcattaa ctaaaaaagt ttattttcct tttgtctggg cagtagtgaa aataactact    5280
cacaacattc actatgtttg caaggaatta acacaaataa aagatgcctt tttacttaaa    5340
cgccaagaca gaaaacttgc ccaatactga gaagcaactt gcattagaga gggaactgtt    5400
aaatgttttc aacccagttc atctggtgga tgttttgca ggttactctg agaattttgc    5460
ttatgaaaaa tcattatttt tagtgtagtt cacaataatg tattgaacat acttctaatc    5520
aaaggtgcta tgtccttgtg tatggtacta aatgtgtcct gtgtacttt gcacaactga    5580
gaatcctgcg gcttggttta atgagtgtgt tcatgaaata aataatggag gaattgtcaa    5640
aaaaaaaaaa aaaaaaaaaa aaaaaaaaaa aaaa                              5674
```

<210> SEQ ID NO 2
<211> LENGTH: 1104
<212> TYPE: PRT

<213> ORGANISM: Human

<400> SEQUENCE: 2

```
Met Ser Phe Arg Ala Ala Arg Leu Ser Met Arg Asn Arg Arg Asn Asp
1               5                   10                  15

Thr Leu Asp Ser Thr Arg Thr Leu Tyr Ser Ser Ala Ser Arg Ser Thr
            20                  25                  30

Asp Leu Ser Tyr Ser Glu Ser Asp Leu Val Asn Phe Ile Gln Ala Asn
        35                  40                  45

Phe Lys Lys Arg Glu Cys Val Phe Ile Lys Asp Ser Lys Ala Thr
    50                  55                  60

Glu Asn Val Cys Lys Cys Gly Tyr Ala Gln Ser Gln His Met Glu Gly
65                  70                  75                  80

Thr Gln Ile Asn Gln Ser Glu Lys Trp Asn Tyr Lys Lys His Thr Lys
                85                  90                  95

Glu Phe Pro Thr Asp Ala Phe Gly Asp Ile Gln Phe Glu Thr Leu Gly
            100                 105                 110

Lys Lys Gly Lys Tyr Ile Arg Leu Ser Cys Asp Thr Asp Ala Glu Ile
        115                 120                 125

Leu Tyr Glu Leu Leu Thr Gln His Trp His Leu Lys Thr Pro Asn Leu
    130                 135                 140

Val Ile Ser Val Thr Gly Gly Ala Lys Asn Phe Ala Leu Lys Pro Arg
145                 150                 155                 160

Met Arg Lys Ile Phe Ser Arg Leu Ile Tyr Ile Ala Gln Ser Lys Gly
                165                 170                 175

Ala Trp Ile Leu Thr Gly Gly Thr His Tyr Gly Leu Met Lys Tyr Ile
            180                 185                 190

Gly Glu Val Val Arg Asp Asn Thr Ile Ser Arg Ser Ser Glu Glu Asn
        195                 200                 205

Ile Val Ala Ile Gly Ile Ala Ala Trp Gly Met Val Ser Asn Arg Asp
    210                 215                 220

Thr Leu Ile Arg Asn Cys Asp Ala Glu Gly Tyr Phe Leu Ala Gln Tyr
225                 230                 235                 240

Leu Met Asp Asp Phe Thr Arg Asp Pro Leu Tyr Ile Leu Asp Asn Asn
                245                 250                 255

His Thr His Leu Leu Val Asp Asn Gly Cys His Gly His Pro Thr
            260                 265                 270

Val Glu Ala Lys Leu Arg Asn Gln Leu Glu Lys Tyr Ile Ser Glu Arg
        275                 280                 285

Thr Ile Gln Asp Ser Asn Tyr Gly Gly Lys Ile Pro Ile Val Cys Phe
    290                 295                 300

Ala Gln Gly Gly Gly Lys Glu Thr Leu Lys Ala Ile Asn Thr Ser Ile
305                 310                 315                 320

Lys Asn Lys Ile Pro Cys Val Val Glu Gly Ser Gly Gln Ile Ala
                325                 330                 335

Asp Val Ile Ala Ser Leu Val Glu Val Glu Asp Ala Leu Thr Ser Ser
            340                 345                 350

Ala Val Lys Glu Lys Leu Val Arg Phe Leu Pro Arg Thr Val Ser Arg
        355                 360                 365

Leu Pro Glu Glu Glu Thr Glu Ser Trp Ile Lys Trp Leu Lys Glu Ile
    370                 375                 380

Leu Glu Cys Ser His Leu Leu Thr Val Ile Lys Met Glu Glu Ala Gly
385                 390                 395                 400

Asp Glu Ile Val Ser Asn Ala Ile Ser Tyr Ala Leu Tyr Lys Ala Phe
```

```
                    405                 410                 415
Ser Thr Ser Glu Gln Asp Lys Asp Asn Trp Asn Gly Gln Leu Lys Leu
                420                 425                 430

Leu Leu Glu Trp Asn Gln Leu Asp Leu Ala Asn Asp Glu Ile Phe Thr
            435                 440                 445

Asn Asp Arg Arg Trp Glu Ser Ala Asp Leu Gln Glu Val Met Phe Thr
        450                 455                 460

Ala Leu Ile Lys Asp Arg Pro Lys Phe Val Arg Leu Phe Leu Glu Asn
465                 470                 475                 480

Gly Leu Asn Leu Arg Lys Phe Leu Thr His Asp Val Leu Thr Glu Leu
                485                 490                 495

Phe Ser Asn His Phe Ser Thr Leu Val Tyr Arg Asn Leu Gln Ile Ala
            500                 505                 510

Lys Asn Ser Tyr Asn Asp Ala Leu Leu Thr Phe Val Trp Lys Leu Val
        515                 520                 525

Ala Asn Phe Arg Arg Gly Phe Arg Lys Glu Asp Arg Asn Gly Arg Asp
530                 535                 540

Glu Met Asp Ile Glu Leu His Asp Val Ser Pro Ile Thr Arg His Pro
545                 550                 555                 560

Leu Gln Ala Leu Phe Ile Trp Ala Ile Leu Gln Asn Lys Lys Glu Leu
                565                 570                 575

Ser Lys Val Ile Trp Glu Gln Thr Arg Gly Cys Thr Leu Ala Ala Leu
            580                 585                 590

Gly Ala Ser Lys Leu Leu Lys Thr Leu Ala Lys Val Lys Asn Asp Ile
        595                 600                 605

Asn Ala Ala Gly Glu Ser Glu Glu Leu Ala Asn Glu Tyr Glu Thr Arg
610                 615                 620

Ala Val Glu Leu Phe Thr Glu Cys Tyr Ser Ser Asp Glu Asp Leu Ala
625                 630                 635                 640

Glu Gln Leu Leu Val Tyr Ser Cys Glu Ala Trp Gly Gly Ser Asn Cys
                645                 650                 655

Leu Glu Leu Ala Val Glu Ala Thr Asp Gln His Phe Ile Ala Gln Pro
            660                 665                 670

Gly Val Gln Asn Phe Leu Ser Lys Gln Trp Tyr Gly Glu Ile Ser Arg
        675                 680                 685

Asp Thr Lys Asn Trp Lys Ile Ile Leu Cys Leu Phe Ile Ile Pro Leu
690                 695                 700

Val Gly Cys Gly Phe Val Ser Phe Arg Lys Lys Pro Val Asp Lys His
705                 710                 715                 720

Lys Lys Leu Leu Trp Tyr Tyr Val Ala Phe Phe Thr Ser Pro Phe Val
                725                 730                 735

Val Phe Ser Trp Asn Val Val Phe Tyr Ile Ala Phe Leu Leu Leu Phe
            740                 745                 750

Ala Tyr Val Leu Leu Met Asp Phe His Ser Val Pro His Pro Pro Glu
        755                 760                 765

Leu Val Leu Tyr Ser Leu Val Phe Val Leu Phe Cys Asp Glu Val Arg
770                 775                 780

Gln Trp Tyr Val Asn Gly Val Asn Tyr Phe Thr Asp Leu Trp Asn Val
785                 790                 795                 800

Met Asp Thr Leu Gly Leu Phe Tyr Phe Ile Ala Gly Ile Val Phe Arg
                805                 810                 815

Leu His Ser Ser Asn Lys Ser Ser Leu Tyr Ser Gly Arg Val Ile Phe
            820                 825                 830
```

```
Cys Leu Asp Tyr Ile Ile Phe Thr Leu Arg Leu Ile His Ile Phe Thr
        835             840             845
Val Ser Arg Asn Leu Gly Pro Lys Ile Ile Met Leu Gln Arg Met Leu
    850             855             860
Ile Asp Val Phe Phe Phe Leu Phe Leu Phe Ala Val Trp Met Val Ala
865             870             875             880
Phe Gly Val Ala Arg Gln Gly Ile Leu Arg Gln Asn Glu Gln Arg Trp
                885             890             895
Arg Trp Ile Phe Arg Ser Val Ile Tyr Glu Pro Tyr Leu Ala Met Phe
                900             905             910
Gly Gln Val Pro Ser Asp Val Asp Gly Thr Thr Tyr Asp Phe Ala His
        915             920             925
Cys Thr Phe Thr Gly Asn Glu Ser Lys Pro Leu Cys Val Glu Leu Asp
    930             935             940
Glu His Asn Leu Pro Arg Phe Pro Glu Trp Ile Thr Ile Pro Leu Val
945             950             955             960
Cys Ile Tyr Met Leu Ser Thr Asn Ile Leu Leu Val Asn Leu Leu Val
                965             970             975
Ala Met Phe Gly Tyr Thr Val Gly Thr Val Gln Glu Asn Asn Asp Gln
                980             985             990
Val Trp Lys Phe Gln Arg Tyr Phe Leu Val Gln Glu Tyr Cys Ser Arg
                995             1000            1005
Leu Asn Ile Pro Phe Pro Phe Ile Val Phe Ala Tyr Phe Tyr Met Val
        1010            1015            1020
Val Lys Lys Cys Phe Lys Cys Cys Cys Lys Glu Lys Asn Met Glu Ser
1025            1030            1035            1040
Ser Val Cys Cys Phe Lys Asn Glu Asp Asn Glu Thr Leu Ala Trp Glu
                1045            1050            1055
Gly Val Met Lys Glu Asn Tyr Leu Val Lys Ile Asn Thr Lys Ala Asn
                1060            1065            1070
Asp Thr Ser Glu Glu Met Arg His Arg Phe Arg Gln Leu Asp Thr Lys
        1075            1080            1085
Leu Asn Asp Leu Lys Gly Leu Leu Lys Glu Ile Ala Asn Lys Ile Lys
    1090            1095            1100
```

COMPOSITIONS AND METHODS FOR THE TREATMENT OF DISEASE ASSOCIATED WITH TRP-P8 EXPRESSION

CROSS-REFERENCE TO RELATED APPLICATION

This application claims priority under 35 U.S.C. 119(e) to U.S. Provisional Patent Application No. 60/497,384 filed Aug. 22, 2003.

TECHNICAL FIELD OF THE INVENTION

The present invention relates generally to the fields of cell biology, biochemistry, and organic chemistry. More specifically, the present invention provides small-molecule modulators of Trp-p8 activity, which include Trp-p8 agonists and Trp-p8 antagonists, as well as compositions comprising small-molecule Trp-p8 modulators. Also provided are methods for identifying and characterizing novel small-molecule Trp-p8 modulators as well as methods for modulating Trp-p8-mediated cation influx and/or apoptosis in a cell and related methods for the treatment of diseases associated with Trp-p8 expression, activation, and/or signaling. Exemplary diseases suitably treated by the compositions and methods of the present invention include cancers, such as lung, breast, colon, and/or prostate cancers.

BACKGROUND OF THE INVENTION

Prostate carcinoma is the most common cancer diagnosed in men in the United States and has the second highest cancer death rate yielding only to lung adenocarcinoma. Parker et al., *CA Cancer J. Clin.* 46:5-27 (1996). Although it is possible to effectively treat organ-confined prostate cancer, there are very limited treatment options for metastatic disease. Thus, it is of great importance to find novel ways to diagnose early stage disease and to closely monitor both progression and treatment of the disease, as well as to develop new therapeutic approaches. To achieve this, it is important to understand the molecular mechanisms of prostate cancer development and to identify new biochemical markers for disease diagnosis and progression.

To date there are very few prostate-specific markers available. The best-known and well-characterized markers of proven prostate cancer diagnostic value are the proteins prostatic acid phosphatase (PAP), prostate specific antigen (PSA), and prostate-specific membrane antigen (PSMA). Each of these proteins has also become the target for novel immunotherapy approaches to the treatment of disease. Horoszewicz et al., *Anticancer Res.* 7:927-935 (1987); Barren et al., *Prostate* 30:65-68 (1997); Murphy et al., *Prostate* 33:281-285 (1997); Murphy et al., *Prostate* 26:164-168 (1995); Rochon et al., *Prostate* 25:219-223 (1995); Correale et al., *J. Immunol.* 161:3186-3194 (1998); and Murphy et al., *Prostate* 38:73-78 (1999).

It has been reported that a cation channel protein, variously designated Trp-p8 (transient receptor potential-p8), TRPM8, and CMR1 (cold and menthol receptor 1), is preferentially expressed in prostate. Cloning of the full-length human trp-p8 cDNA revealed a transcript corresponding to an 1104 amino acid polypeptide sharing homology with the trp family of calcium channels. Clapham et al., *Nature Reviews* 2:387-396 (2001) and Clapham et al., IUPHAR Compendium, TRP Channels (2002). Trp-p8 shows particularly high homology with the human TRPC7 gene—a putative $Ca^{2+}$ channel protein of the trp family that is highly expressed in brain tissue. Nagamine et al., *Genomics* 54:124-131 (1998). Trp-p8 also shows significant homology to human melastatin, another Trp family-related protein expressed in melanocytes and believed to be a tumor suppressor gene. Duncan et al., *Cancer Res.* 58:1515-1520 (1998); and Hunter et al., *Genomics* 54:116-123 (1998). Perhaps of greatest interest is the observation that the trp-p8 gene appears to be expressed in a large spectrum of nonprostatic in addition to prostatic neoplastic lesions. Tsavaler et al., *Cancer Res.* 61(9):3760-9 (2001).

The Trp superfamily comprises more than 20 related cation channel proteins that have been implicated in processes including sensory physiology to vasorelaxation and male fertility. Defects in Trp channels have been associated with changes in growth control and tumor suppression. While all Trp proteins are calcium channels, they vary significantly in their selectivity and mode of activation. Members of the Trp superfamily share significant sequence homology and predicted structural similarities, such as size of predicted transmembrane segments.

Trp-p8 is over-expressed in a range of cancers including prostate, breast, lung and colon, while within normal tissues, it is predominantly expressed in human prostate [Tsavaler et al., supra] and dorsal root ganglia (DRG, Dendreon, unpublished observation). Fuessel et al. reported that Trp-p8 is a highly prostate-specific and prostate carcinoma-associated gene thus qualifying it as a potential target for specific therapies. *International J. of Oncology* 23:221-228 (2003). Among other species, Trp-p8 orthologues are reportedly expressed in a subset of DRG and trigeminal ganglia (TG) neurons in rat [McKemy et al., *Nature* 416(6870:52-8 (2002)] and mouse [Peier et al., *Cell* 108(5):705-15 (2002)] as well. Thus, Trp-p8 is a pantumor-expressed marker with significant potential use in disease diagnosis and monitoring of disease progression during treatment as well as a viable target for cancer therapy.

In two articles published concurrently, it was reported for the first time that Trp-p8 orthologues, in response to cold and certain cooling compounds, initiate an influx of cations, such as calcium, from the extracellular space. McKemy et al., supra; and Peier et al., supra. Two of the best known modulators of Trp-p8 activity are the Trp-p8 agonists menthol and Icilin. Menthol is effective in inducing calcium influx at ~10-100 μM while Icilin is more potent with an effective concentration range of 0.1-1 μM.

The higher temperature threshold reported for Trp-p8 activation by the most widely studied agonist, menthol (2-isopropyl-5-methyl-cyclohexanol), is about 30-32° C. in a variety of cells (cold-sensitive neurons, Trp-p8 heterologously expressed in *Xenopus* oocytes, HEK293 and CHO cells). McKemy et al., *Nature*, supra; Peier et al., *Cell*, supra; Nealen et al., *J Neurophysiol.* 90(1):515-520 (2003); and Reid et al., *J Physiol.* 545(Pt 2):595-614 (2002).

Although certain agonist compounds have been shown to activate Trp-p8 expressing cells up to 32° C., there has been no report disclosing growth manipulation in cells at physiological temperature (i.e. 37° C.), the temperature at which a compound must be active in order to be an efficacious in vivo therapeutic.

Association of Trp-p8 with prostate, lung, breast, and colon cancers and the important role various ion channels play in vital cell functions suggest that Trp-p8 channel may have a significant function in cancer cell signaling and/or proliferation. Modulation of Trp-p8 activity, either by activating via an agonist or inhibiting via an antagonist, at a physiological temperature can be valuable as a therapeutic to manipulate the Trp-p8 expressing cells in a specific manner.

Accordingly, there remains a need in the art for small-molecule modulators of Trp-p8 activity, compositions comprising one or more small-molecule Trp-p8 modulators, and methods for the identification and use of small-molecules for modulating the activity of Trp-p8 in a cell and for the treatment of disease associated with the aberrant expression of Trp-p8.

SUMMARY OF THE INVENTION

The present invention fulfills these and other related needs by providing small molecule modulators of Trp-p8 activity, including Trp-p8 agonists and Trp-p8 antagonists, as well as compositions comprising such Trp-p8 modulators, and methods for identifying and using Trp-p8 modulators. Within certain embodiments, compounds of the present invention bind to and activate Trp-p8 and/or stimulate cation influx, including but not limited to calcium influx, in a cell wherein cation influx is correlative of Trp-p8 modulator induced toxicity. Thus, within these and other embodiments, Trp-p8 agonists of the present invention are effective in inhibiting growth of and/or inducing apoptosis and/or necrosis in a cell expressing Trp-p8. Within alternative embodiments are provided Trp-p8 antagonists that are effective in reducing the basal activity of Trp-p8 in a cell thereby reducing the viability of Trp-p8 expressing cells. Advantageously, therefore, agonists and antagonists of the present invention can be used to treat diseases including, but not limited to, cancers of the breast, lung, colon, and/or prostate, that are associated with Trp-p8 expression.

One or more Trp-p8 modulator can be formulated in compositions, including pharmaceutical compositions, comprising one or more pharmaceutically acceptable carrier or excipient and/or one or more additional therapeutic compound. Such compositions will find utility in methods for the treatment of one or more disease associated with Trp-p8 expression. Thus, in one embodiment, the present invention provides the following Trp-p8 modulators and derivatives thereof:

A compound of Formula I

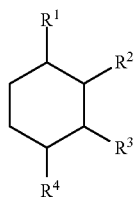

wherein $R^1$ is selected from the group consisting of H, OH, $CH_3$, $CH_3$—CH—$CH_3$ (isopropyl), and $CH_3$—C═$CH_2$ (isopropenyl);

$R^2$ is selected from the group consisting of H;

$R^3$ is selected from the group consisting of O, OH, acetate, lactate, carboxamide, butanamide, sulphanamide, and propanetriol; and $R^4$ is selected from the group consisting of $CH_3$—CH—$CH_3$ (isopropyl), isopropane-2-ol, and $CH_3$—C═$CH_2$ (isopropenyl).

Exemplary compounds of Formula I include the following:

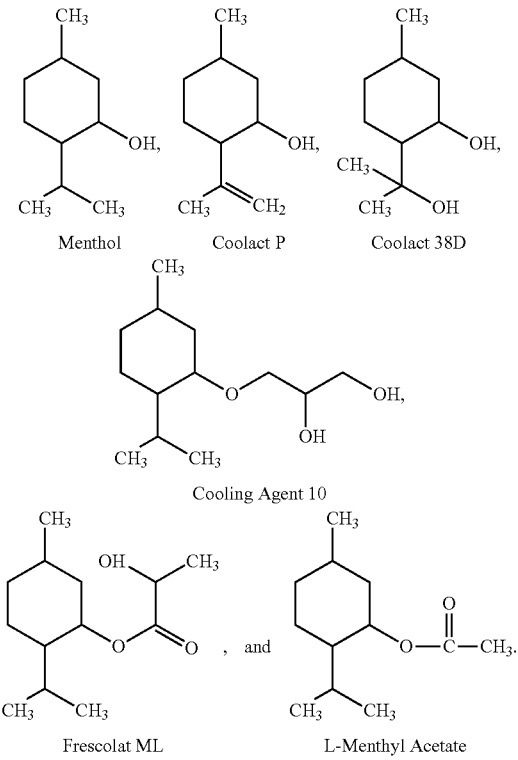

These exemplary Formula I Trp-p8 modulators have the following trade and chemical names: Menthol (2-isopropyl-5-methyl-cyclohexanol) (Sigma-Aldrich, Inc.; St. Louis, Mo.); Frescolat ML (Harris & Ford, LLC; Indianapolis, Ind.; Menthyl lactate); L-Menthyl Acetate (Millenium Chemicals; Olympia Fields, Ill.; Cyclohexanol-5-methyl-2-(1-methyl-ethyl)-acetate-[1R-(1 alpha,2beta,5alpha)]-); Cooling Agent 10 (Takasago International Corp.; Rockleigh, N.J.; (1)-Menthoxypropane-1,2-diol); Coolact P® (Takasago International Corp.; (−)-Isopulegol); and Coolact 38D® (Takasago International Corp.).

In another embodiment, the present invention further provides the following small-molecule Trp-p8 modulators and derivatives thereof:

A compound of Formula II

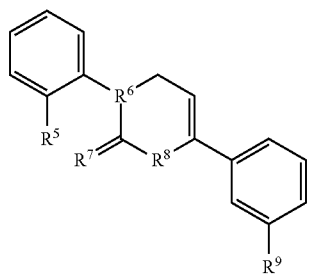

wherein $R^5$ is selected from the group consisting of H, OH, $CH_3$, $CH_3$—CH—$CH_3$ (isopropyl), and $CH_3$—C═$CH_2$ (isopropenyl);

$R^6$ is selected from the group consisting of N;

$R^7$ is selected from the group consisting of O and N;

$R^8$ is selected from the group consisting of NH, O, and S; and $R^9$ is selected from the group consisting of $NO_2$.

Compounds of Formula II are exemplified herein by Icilin (1-(2-hydroxyphenyl)-4-(3-nitrophenyl)-1,2,3,6-tetrahydropyrimidine-2-one aka 3,4-dihydro-3-(2-hydroxyphenyl)-6-(3-nitrophenyl)-(1H)-pyrimidin-2-one).

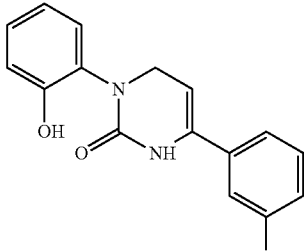

Icilin

In another embodiment, the present invention further provides the following acyclic carboxamide Trp-p8 agonists and derivatives thereof as presented in U.S. Pat. No. 4,153,679, incorporated herein by reference:

A compound of Formula III

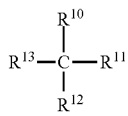

wherein $R^{10}$ is selected from the group consisting of H and a $C_1$-$C_5$ alkyl including, but not limited to, $CH_3$, $C_2H_5$, $CH_3$—CH—$CH_3$ (isopropyl) and $CH_3$—C=$CH_2$ (isopropenyl);

$R^{11}$ is selected from the group consisting of OH, carboxamide, butanamide, propanetriol, and CONR'R'', wherein R' is selected from the group consisting of H, $CH_3$, $C_2H_5$, $C_4H_8$ (cyclobutyl), and $C_4H_8O$, and wherein R'' is selected from the group consisting of $C_2H_5OOCH_2$, $C_2H_5$, $CH_3$—CH—$CH_3$ (isopropyl), $HOCH_2C(CH_3)_2$, $HOCH_2CH_2$, $C_4H_9$ (tertbutyl), and $C_4H_9$ (secbutyl);

$R^{12}$ is selected from the group consisting of H and a $C_1$-$C_5$ alkyl including, but not limited to, $CH_3$, $CH_3$—CH—$CH_3$ (isopropyl), $CH_3$—C=$CH_2$ (isopropenyl), $C_4H_9$ (secbutyl), $C_4H_9$ (isobutyl), $C_4H_9$ (n-butyl), and $C_5H_{11}$ (isohexyl); and $R^{13}$ is selected from the group consisting of H and a $C_1$-$C_5$ alkyl including, but not limited to, $CH_3$, $C_2H_5$, $CH_3$—CH—$CH_3$ (isopropyl), $CH_3$—C=$CH_2$ (isopropenyl), $C_4H_9$ (secbutyl), and $C_4H_9$ (isobutyl).

Compounds of Formula III are exemplified herein by WS-23 (2-Isopropyl-N,2,3-trimethylbutyramide aka N,2,3-trimethyl-2-isopropyl butamide).

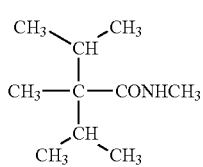

WS-23

In another embodiment, the present invention further provides the following 3-substituted-p-menthane Trp-p8 modulators and derivatives thereof exemplified by those presented in U.S. Pat. No. 4,150,052, incorporated herein by reference:

A compound of Formula IV

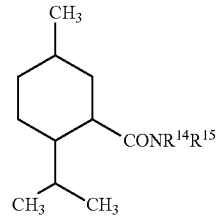

wherein $R^{14}$ is selected from the group consisting of H and an aliphatic group containing up to 25 carbon atoms;

$R^{15}$ is selected from the group consisting of H, OH and an aliphatic group containing up to 25 carbon atoms, with the proviso that when $R^{15}$ is H, $R^{14}$ may also be an aryl group of up to 10 carbon atoms and selected from the group consisting of substituted phenyl, phenalkyl, substituted phenalkyl, naphthyl, substituted naphthyl, and pyridyl; and $R^{14}$ and $R^{15}$, when taken together with the nitrogen atom to which they are attached, may form a cyclic or heterocyclic group of up to 25 carbon atoms, e.g., a piperidino or a morpholino group. Exemplary such cyclical groups may be selected from the group consisting of 3-phenyl-piperidin-1-yl, 3-phenyl-pyrrolidin-1-yl, 6,7-dimethoxy-1-methyl-3,4-dihydro-1H-isoquinolin-2-yl, and 4-pyrimidin-2-yl-piperazin-1-yl.

Typical values for $R^{14}$ and $R^{15}$ when aliphatic are methyl, ethyl, propyl, butyl, isobutyl, n-decyl, cyclopropyl, cyclohexyl, cyclopentyl, cycloheptylmethyl, 2-hydroxyethyl, 3-hydroxy-n-propyl, 6-hydroxy-n-hexyl, 2-aminoethyl, 2-acetoxyethyl, 2-ethylcarboxyethyl, 4-hydroxybut-2-ynyl, and carboxymethyl.

When $R^{14}$ is aryl, typical values are benzyl, naphthyl, 4-methoxyphenyl, 2-methoxy-4-methoxyphenyl, 3-methoxy-5-methoxyphenyl, 4-methyl-5-chlorophenyl, 4-hydroxyphenyl, 4-methylphenyl, 3-methyl-4-methylphenyl, 3-hydroxy-4-methylphenyl, 4-fluorophenyl, 4-chlorophenyl, 4-bromophenyl, 4-ethylphenyl, 2-fluoro-4-fluorophenyl, 4-nitrophenyl, 2-hydroxynaphthyl, pyridyl, [1-carbamoyl-2-(1H-indol-3-yl)-ethyl, 1,3-dioxo-2,3-dihydro-1H-isoindol-4-yl, 1,3-dioxo-2,3-dihydro-1H-isoindol-5-yl, 1-carbamoyl-2-(4-hydroxyphenyl)ethyl, 1-carbamoyl-2-phenylethyl, 1-hydroxymethyl-2-(1H-indol-3-yl)ethyl, 1-hydroxymethyl-2-(4-chlorophenyl)ethyl, 1-hydroxymethyl-2-(4-hydroxyphenyl)ethyl, 1-hydroxymethyl-2-hydroxy-2-phenylethyl, 1-hydroxymethyl-2-phenyl ethyl, 1-methoxymethyl-2-phenylethyl, 1-methyl-2-(4-chlorophenyl)-ethyl, 1-methyl-2-(5-fluoro-1H-indol-3-yl)-ethyl, 1-methyl-2-hydroxy-2-phenylethyl, 1-oxo-2-phenylethyl, 1-phenyl-cyclopentylmethyl, 2-(1-cyclopentyl-pyrrolidin-3-yl)-ethyl, 2-(1H-indol-3-yl)ethyl, 2-(2,3-dimethoxyphenyl)ethyl, 2-(2,4-dichlorophenyl)ethyl, 2-(2,4-dimethylphenyl)ethyl, dimethoxyphenyl)ethyl, 2-(2,5-dimethylphenyl)-ethyl, 2-(2,6-dimethylphenyl)ethyl, 2-(2-chloro-6-fluorophenyl)ethyl, 2-(2-chlorophenyl)ethyl, 2-(2-fluorophenyl)ethyl, 2-(2-furyl)ethyl, 2-(2-methoxy-5-bromophenyl)ethyl, 2-(2-methoxyphenyl)-ethyl, 2-(2-methylphenyl)ethyl, 2-(3,4-dichlorophenyl)ethyl, 2-(3,4-dimethoxyphenyl)ethyl, dimethoxyphenyl)ethyl, 2-(3-bromo-4-methoxyphenyl)ethyl, 2-(3-chlorophenyl)ethyl, 2-(3-ethoxyphenyl)ethyl, 2-(3-fluorophenyl)ethyl, 2-(3-hydroxy-4-methoxyphenyl)-ethyl, 2-(3-hydroxyphenyl)ethyl, 2-(3-methoxy-4-ethoxyphenyl)ethyl, 2-(3-methoxy-4-hydroxyphenyl)ethyl, 2-(3-methoxyphenyl)ethyl, 2-(3-methylphenyl)ethyl, 2-(3-trifluoromethylphenyl)ethyl, 2-(4-bromophenyl)-ethyl, 2-(4-chlorophenyl)ethyl, 2-(4-ethylphenyl)ethyl, 2-(4-fluorophenyl)ethyl, 2-(4-hydroxyphenyl)ethyl, 2-(4-methoxy-phenyl)-2-oxo-ethyl, 2-(4-methoxyphenyl)ethyl, 2-(4-methylphenyl)ethyl, 2-(4-methylphenyl)ethyl, 2-(4-methylsulfanylphenyl)ethyl, 2-(4-nitrophenyl)ethyl, 2-(4-sulfamoyl-phenyl)-ethyl, 2-(5-methoxy-1H-indol-3-yl)-ethyl, 2-(6-fluoro-1H-indol-3-yl)-ethyl, 2-(6-methoxy-1H-indol-3-yl)-ethyl, 2-(7-methyl-1H-indol-3-yl)-ethyl, 2-(N,N-dipropylamino)ethyl, 2-(pyridin-2-yl)-ethyl, 2-(pyridin-3-yl)-ethyl, 2-(pyridin-4-yl)-ethyl, 2,2-diphenylethyl, 2,3-difluorobenzyl, 2,3-dimethoxyphenyl, 2,4-dichlorophenyl, 2,4-difluorophenyl, 2,4-dimethoxyphenyl, 2,4-dimethylphenyl, 2-bromo-4-methylphenyl, 2-chloro-4-cyanophenyl, 2-chloro-4-fluorophenyl, 2-chloro-4-iodophenyl, 2-chloro-4-nitrophenyl, 2-chloro-5-nitrophenyl, 2-chlorophenyl, 2-cyclohex-1-enyl-ethyl, 2-fluoro-4-chlorophenyl, 2-fluoro-5-nitrophenyl, 2-hydroxy-2-(3-hydroxyphenyl)ethyl, 2-hydroxy-2-(4-hydroxyphenyl)ethyl, 2-hydroxy-2-phenylethyl, 2-iodophenyl, 2-methyl-1,3-dioxo-2,3-dihydro-1H-isoindol-5-yl, 2-methyl-2-phenylethyl, 2-methyl-4-broophenyl, 2-methyl-5-nitrophenyl, 2-methylphenyl, 2-nitro-4-fluorophenyl, 2-nitrophenyl, 2-oxo-2,3-dihydro-1H-benzoimidazol-5-yl, 2-oxo-2-phenylethyl, 2-phenyl-1H-benzoimidazol-5-yl, 2-phenyl-2-(4-chlorophenyl)ethyl, 2-phenyl-2-(4-fluorophenyl)-ethyl, 2-phenyl-2-(4-methoxyphenyl)ethyl, 2-phenylethenyl, 2-phenylethyl, 2-pyridin-2-yl-benzooxazol-5-yl, 2-pyridin-3-yl-1H-benzoimidazol-5-yl, 2-thiophen-2-yl-ethyl), 2-trilfouromethyl-1H-benzoimidazol-5-yl, 3,4,5-trifluorophenyl, 3,4,5-trimethoxyphenyl, 3,4-cyclopentanephenyl, 3,4-dichlorophenyl, 3,4-dimethylphenyl, 3,5-dimethoxyphenyl, 3-acetamidophenyl, 3-bromo-4-methylphenyl, 3-carboxamidophenyl, 3-chloro-4-methoxyphenyl, 3-chloro-4-methylphenyl, 3-chloro-4-morpholin-4-yl-phenyl, 3-hydroxymethylphenyl, 3-nitrophenyl, 3-oxo-indan-5-yl, 3-phenylpropyl, 3-yl-acetophenone, 4-(1,1-dioxo-1,6-thiomorpholin-4-ylmethyl)-phenyl, 4-(1-hydroxyethyl)phenyl, 4-(2-hydroxyethyl)phenyl, 4-(4-ethyl-piperazin-1-yl)-phenyl, 4-(4-methyl-1H-benzoimidazol-2-yl)-phenyl, 4-(4-methyl-piperazin-1-ylmethyl)-phenyl, 4-(morpholine-4-sulfonyl)-phenyl, 4-[1,3-dioxo-2-(2-trifluoromethyl-phenyl)-2,3-dihydro-1H-isoindol-5-yloxy]-phenyl, 4-[2-(2-methoxy-phenyl)-1,3-dioxo-2,3-dihydro-1H-isoindol-5-yloxy]-phenyl, 4-{2-[2-(3,4-dimethoxy-phenyl)-ethyl]-1,3-dioxo-2,3-dihydro-1H-isoindol-5-yloxy}-phenyl, 4-acetylphenyl, 4-azepan-1-ylmethyl-phenyl, 4-benzooxazol-2-yl-phenyl, 4-Biphenyl, 4-bromophenyl, 4-carboxamidophenyl, 4-chlorophenyl, 4-cyanophenyl, 4-ethoxyphenyl, 4-ethylphenyl, 4-fluorophenyl, 4-hydroxymethylphenyl, 4-methoxyphenyl, 4-methyl-2-oxo-2H-chromen-7-yl, 4-methylcyclohexyl, 4-methylphenyl, 4-methylsulfanylphenyl, 4-nitrobenzyl, 4-pyrrolidin-1-ylmethyl-phenyl, 4-trifluoromethylphenyl, benzo[1,3]dioxol-5-yl, benzoylamino, benzyloxy, bicyclo[2.2.1]hept-2-yl, C-1H-indazol-5-yl, cycloheptyl, indan-2-yl, N-(2-diethylamino-ethyl)-benzamide-4-yl, N'-quinoxalin-2-yl-amino, and phenylcyclopropyl.

Trp-p8 modulators of Formula IV are exemplified herein by the Trp-p8 agonists WS-3 (Millenium Chemicals; N-Ethyl-p-menthane-3-carboxamide aka cyclohexanecarboxamide, N-ethyl-5-methyl-2(1-methylethyl)) and by WS-12 (N-(4-methoxyphenyl)-p-menthan-3-carboxamide aka cyclohexanecarboxamide, N-(4-methoxyphenyl)-5-methyl-2(1-methylethyl)), and the compounds presented in Table 1.

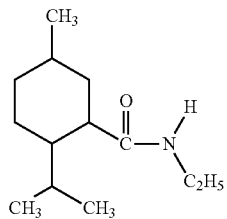

WS-3

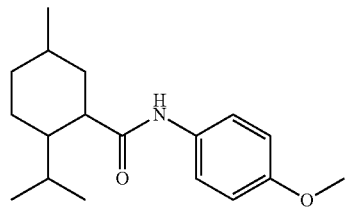

WS-12

In a further embodiment, the present invention provides the following Trp-p8 modulators and derivatives thereof that comprise at least one ketal moiety, including, but not limited to the Trp-p8 agonists 1-menthone glycerol ketal and 3,3,5-trimethylcyclohexaone glycerol ketal presented in U.S. Pat. No. 5,266,592, incorporated herein by reference: A compound comprising at least one ketal of Formula V

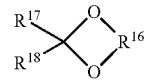

V wherein $R^{16}$ is selected from the group consisting of a $C_2$-$C_6$ alkylene group having at least one, but not more than three, hydroxyl group(s), preferably one hydroxyl group; and either $R^{17}$ and $R^{18}$, independently of one another, represent $C_1$-$C_{10}$-alkyl which is optionally substituted by 1 to 3 groups selected from the group consisting of hydroxyl, amino, thio, and halogen (e.g., fluorine, chlorine, bromine, or iodine), $C_5$-$C_7$-cycloalkyl, preferably cyclohexyl, $C_6$-$C_{12}$-aryl, preferably phenyl, with the proviso that the total of the C atoms of $R^{17}$ and $R^{18}$ is not less than 3; or $R^{17}$ and $R^{18}$ together represent an alkylene group that, together with the carbon atom that carries the groups $R^{17}$ and $R^{18}$, forms a 5-7-membered ring, it being possible for this alkylene group, in turn, to be substituted by $C_1$-$C_6$-alkyl groups.

Preferred groups $R^{17}$ and $R^{18}$ comprise methyl, isopropyl, and tert-butyl.

Trp-p8 modulators comprising a ketal of Formula V include the following compounds wherein $R^{16}$ is as defined above:

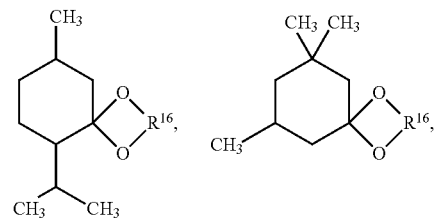

-continued

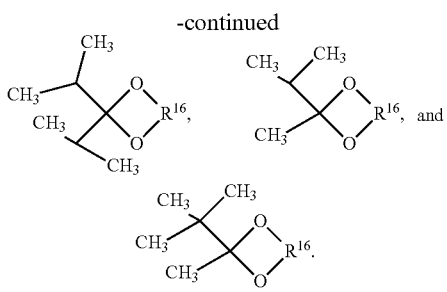

Compounds comprising a ketal of Formula V are exemplified herein by the Trp-p8 agonist Frescolat MGA (Harris & Ford, LLC; Menthone Glycerin Acetal),

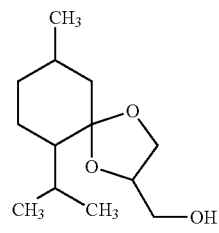

Frescolat MGA

In yet a further embodiment, the present invention provides Formula VI small-molecule Trp-p8 agonists and derivatives thereof exemplified herein by L-Carvone (Millenium Chemicals; (R)-5-Isopropenyl-2-methyl-2-cyclohexenone p-Mentha-6,8-dien-2-one),

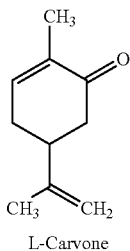

L-Carvone

Other embodiments of the present invention provide Trp-p8 modulators of Formula VII. A compound of Formula VII

VII

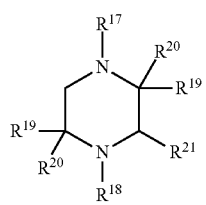

wherein $R^{17}$ is selected from the group consisting of 2-pyridyl, 2-nitro-4-trifluoromethylphenyl, 2-nitro-4-chlorophenyl, 2-methoxyphenyl, 2-chlorophenyl, phenyl, 2-methyl-quinolin-3-yl, 4-methoxyphenyl, 4-fluorophenyl, 3-azepan1-yl-5-(4-trifluoromethoxy)phenylamino[1,3,5]triazyl, cyclohexyl, diphenylmethyl, 2-phenylethyl, 4-hydroxy-cyclohexyl, cycloheptyl, cyclopentyl, C-benzo[1,3]dioxol-5-yl-methyl, 2-pyridyl, and 4-chlorobenzyl;

$R^{18}$ is selected from the group consisting of 1-benzyl-1H-pyrazolo[3,4-d]pyrimidin-4-yl, 3-benzylamino-2-nitrophenyl, 5-nitro-quinolin-8-yl, 1-yl-3-(2-isopropyl-5-methyl-cyclohexyloxy)-propan-2-ol, 1-phenyl-1H-pyrazolo[3,4-d] pyrimidin-4-yl, benzyl-2-methyl-quinazolin-4-yl, 3-methyl-5-morpholin-4-yl-2-nitro-phenyl, 2-nitro-5-piperazin-1-yl-ethanol, 1-yl-3-(2-isopropyl-5-methyl-cyclohexyloxy)-propan-2-ol, 4-(2,5-dimethyl-pyrrol-1-yl)-2-nitro-phenyl, 2-nitro-3-trifluoromethanesulfonyl-phenyl, 1-phenyl-1H-pyrazolo[3,4-d]pyrimidin-4-yl, 2-(2-Fluoro-phenoxymethyl)-2-cyano oxazolyl, adamantyl, 5-(benzo[1,3]dioxol-5-ylamino)-10b, 10c-dihydro-anthra[1,9-cd]isoxazol-6-one-yl, 2-methyl-thiazolo[3,2-b][1,2,4]triazol-6-ol 4-methylphenyl methyl, 3-benzyl-3H-quinazolin-4-one-2-yl, cyclopentyl, tetrahydronapthyl, cyclooctyl, cyclohexyl, C-[3-(4-chloro-phenyl)-2,5-dimethyl-pyrazolo[1,5-a]pyrimidin-7-yl]-methyl, C-(2-benzyl-5,6,7,8-tetrahydro-benzo [4,5]thieno[2,3-d]pyrimidin-4-yl)-methyl, and 1-yl-3-(2-isopropyl-5-methyl-cyclohexyloxy)-propan-2-ol;

$R^{19}$ and $R^{20}$ are each independently selected from the group consisting of H and O; and $R^{21}$ is selected from the group consisting of 4-methylphenyl, 2-chloro-4-fluorophenyl, and 4-chlorophenyl.

In other embodiments, the present invention provides Formula VIII small-molecule Trp-p8 modulators. A compound of Formula VIII

VIII

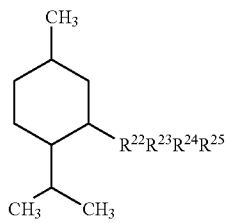

wherein $R^{22}$ is a linker moiety, which may be selected from the group consisting of oxyacetamide, urea, carbamate, thiourea, sulfonamide, amine, amide. Formula VIII antagonists are represented by the following sub-formulae (Formula VIII-A, Formula VIII-B, Formula VIII-C, Formula VIII-D, Formula VIII-E, Formula VIII-F, and Formula VIII-G):

VIII-A

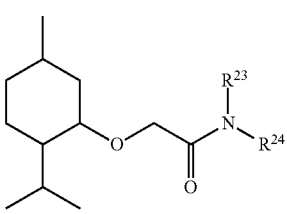

VIII-B

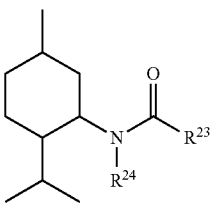

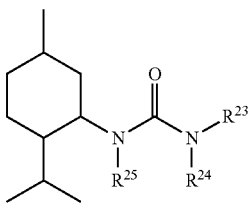
VIII-C

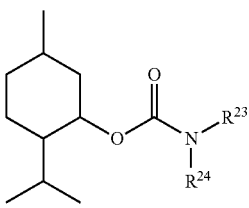
VIII-D

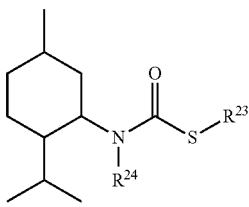
VIII-E

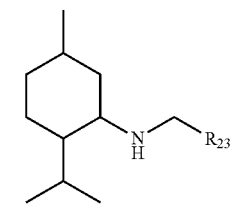
VIII-F

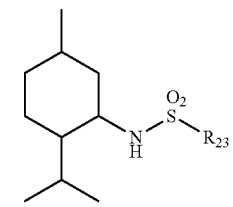
VIII-G

Irrespective of which of the seven $R^{22}$ linker moieties is employed, $R^{23}$ is selected from the group consisting of H, tetrahydro isoquinolinyl, tetrahydro quinolinyl, 3-methyl indolinyl, indolinyl, 2-(N-methyl, N-phenylethyl)amino ethyl, 3-methyl indolinyl, 1-phenyl ethyl, 2-chloro benzyl, 2-methoxybenzyl, 2-methoxyphenyl, 2-cyclohex-1-enyl ethyl, (1-phenyl-cyclophentyl)-methyl, 2-(tetrahydroquinolinyl)-ethyl, 1-propyl-1,2,3,4-tetrahydro-pyrrolo[1,2-a]pyrazine, cycloheptyl, 3-cyclohexylsulfanylpropyl, 2-cyclohex-1-enyl ethyl, 2-(N-isopropyl, N-phenylethyl)amino ethyl, 1-methyl-1,2,3,4-tetrhydro-pyrrolo[1,2-a]pyrazine, 2-cyclopentylethyl, 2-phenylcyclopropyl, 1-phenoxyethyl, 4-butyloxyphenyl, (2-nitrophenoxy)methyl, 4,7,7-trimethyl-2-oxabicyclo[2.2.1]heptan-3-one, C-(1-phenyl-5-propyl-1H-pyrazol-4-yl)-methyl, benzyl, 2-chlorobenzyl, 1-[3-(6,7-dimethoxy-1-methyl-3,4-dihydro-1H-isoquinolin-2-ylmethyl)-4-methoxy-phenyl]-2,3,4,9-tetrahydro-1H-b-carboline, C-[3-(4-butoxy-phenyl)-1H-pyrazol-4-yl]-methyl, 4-(azepane-1-sulfonyl)-phenyl, and 5-(7-chloro-quinolin-4-ylsulfanyl)-[1,3,4]thiadiazol-2-yl;

$R^{24}$ is selected from the group consisting of H, tetrahydro isoquinolinyl, tetrahydro quinolinyl, 3-methyl indolinyl, indolinyl, 3-methyl indolinyl, 1-propyl-1,2,3,4-tetrahydro-pyrrolo[1,2-a]pyrazine, 1-methyl-1,2,3,4-tetrhydro-pyrrolo[1,2-a]pyrazine, and 1-[3-(6,7-dimethoxy-1-methyl-3,4-dihydro-1H-isoquinolin-2-ylmethyl)-4-methoxy-phenyl]-2,3,4,9-tetrahydro-1H-b-carboline; and $R^{25}$ is selected from the group consisting of H.

Other aspects of the present invention provide compositions, including pharmaceutical compositions, comprising one or more small-molecule Trp-p8 modulators of Formula I, Formula II, Formula III, Formula IV, Formula V, Formula VI, Formula VII, and Formula VIII in combination with a pharmaceutically acceptable excipient, carrier and/or diluent. Exemplified herein within the Examples are specific Trp-p8 agonists of Formula I, Formula II, Formula III, Formula IV, Formula V, and Formula VI and Trp-p8 antagonists of Formula VII and Formula VIII. Also provided are Trp-p8 antagonists of Formula I, Formula Formula III, Formula IV, Formula V, and Formula VI and Trp-p8 agonists of Formula VII and Formula VIII.

Within still further aspects, compositions of the present invention comprise one or more compound of Formula I, Formula II, Formula III, Formula IV, Formula V, Formula VI, Formula VII, and/or Formula VIII formulated together with one or more cancer therapeutic agent. Alternatively, compositions of the present invention comprise a compound of Formula I, Formula II, Formula III, Formula IV, Formula V, Formula VI, Formula VII, and/or Formula VIII independently formulated with one or more cancer therapeutic agent. That is, one or more compound of Formula I, Formula II, Formula III, Formula IV, Formula V, Formula VI, Formula VII, and/or Formula VIII and the cancer therapeutic agent are separately formulated.

Suitable cancer therapeutic agents include, but are not limited to, antimitotic agents including, but not limited to, paclitaxel, vincristine, and etoposide; alkylating agents including, but not limited to, mechlorethamine, cyclophosphamide, and carmustine; antimetabolites including, but not limited to, methotrexate, gemcitabine, lometrexol, 5-fluorouracil, and 6-mercaptopurine; cytotoxic antibiotics including, but not limited to, doxorubicin, daunorubicin, bleomycin, mitomycin C, and streptozocin; platinum agents including, but not limited to, cisplatin and carboplatin; hormonal agents including, but not limited to, anti-estrogens such as tamoxifen and diethylstilbestrol as well as anti-androgens such as flutamide; antiangiogenesis agents; and farnesyl transferase inhibitors.

In certain aspects, compounds of Formula I, Formula II, Formula III, Formula IV, Formula V, Formula VI, Formula VII, and/or Formula VIII are administered in combination with cancer therapeutic agents that are themselves ineffective for modulating Trp-p8 activity in a cell expressing Trp-p8. Surprisingly, these types of combination therapy result in enhanced efficacy relative to the use of a single compound of Formula I, Formula II, Formula III, Formula IV, Formula V, Formula VI, Formula VII, and/or Formula VIII alone.

In other aspects, compounds of Formula I, Formula II, Formula III, Formula IV, Formula V, Formula VI, Formula VII, and/or Formula VIII are administered in combination with one or more additional Trp-p8 modulator including, but not limited to, a compound of Formula I, Formula II, Formula III, Formula IV, Formula V, Formula VI, Formula VII, and/or Formula VIII.

Within certain of these embodiments are provided small-molecule antagonists of the small-molecule Trp-p8 agonists presented herein. Thus, within certain embodiments are provided small-molecule Trp-p8 antagonists of Formula I, Formula II, Formula III, Formula IV, Formula V, Formula VI, Formula VII, and/or Formula VIII, and derivatives thereof, of one or more Formula I, Formula II, Formula III, Formula IV, Formula V, Formula VI, Formula VII, and/or Formula VIII Trp-p8 agonist.

Further embodiments of the present invention provide methods for decreasing cell viability and/or inhibiting cell growth, methods for stimulating cation influx, and methods for inducing apoptosis and/or necrosis in a cell expressing Trp-p8. Exemplary such methods comprise the step of contacting a cell with a compound of Formula I, Formula II, Formula III, Formula IV, Formula V, Formula VI, Formula VII, and/or Formula VIII in a concentration and for a time required to decrease cell viability and/or inhibit cell growth, to raise intracellular calcium, and/or to induce apoptosis and/or necrosis of the cell.

In still further embodiments, the present invention provides methods for treating a disease in a mammal, most typically a human, by administering one or more compound and/or composition of the present invention. In certain aspects, the methods include the administration of a composition comprising a combination of a compound of Formula I, Formula II, Formula III, Formula IV, Formula V, Formula VI, Formula VII, and/or Formula VIII with one or more cancer therapeutic agent delivered in a simultaneous manner, such as in a single formulation. In certain other aspects, the methods of the present invention include combination therapy wherein the compound of Formula I, Formula II, Formula III, Formula IV, Formula V, Formula VI, Formula VII, and/or Formula VIII is administered first in one formulation, followed by the cancer therapeutic agent in a separate formulation. The methods also include a cancer therapeutic agent being delivered first in one formulation, followed by a compound of Formula I, Formula II, Formula III, Formula IV, Formula V, Formula VI, Formula VII, and/or Formula VIII in a separate formulation.

Therapeutic methods of the present invention are particularly effective in the treatment of cancers associated with the expression of Trp-p8 including, but not limited to, certain colon, lung, breast, and prostate cancers.

The above-mentioned and additional features of the present invention and the manner of obtaining them will become apparent, and the invention will be best understood by reference to the following more detailed description, read in conjunction with the accompanying figures.

BRIEF DESCRIPTION OF THE FIGURES

FIG. 2A is a positive control demonstrating that CHO and CHO/Trp-p8 cells respond similarly to 1 μM Ionomycin at 37° C. in the calcium flux assay. FIG. 2B is a negative control demonstrating that parental CHO cells that do not express endogenous or exogenous Trp-p8 do not respond to Trp-p8 agonists even at a concentration of 10 μM. FIG. 2C demonstrates that the Trp-p8 agonist, designated herein as compound 1603, induced a specific, concentration-dependent response in CHO/Trp-p8 cells at 37° C.

Figure 1:
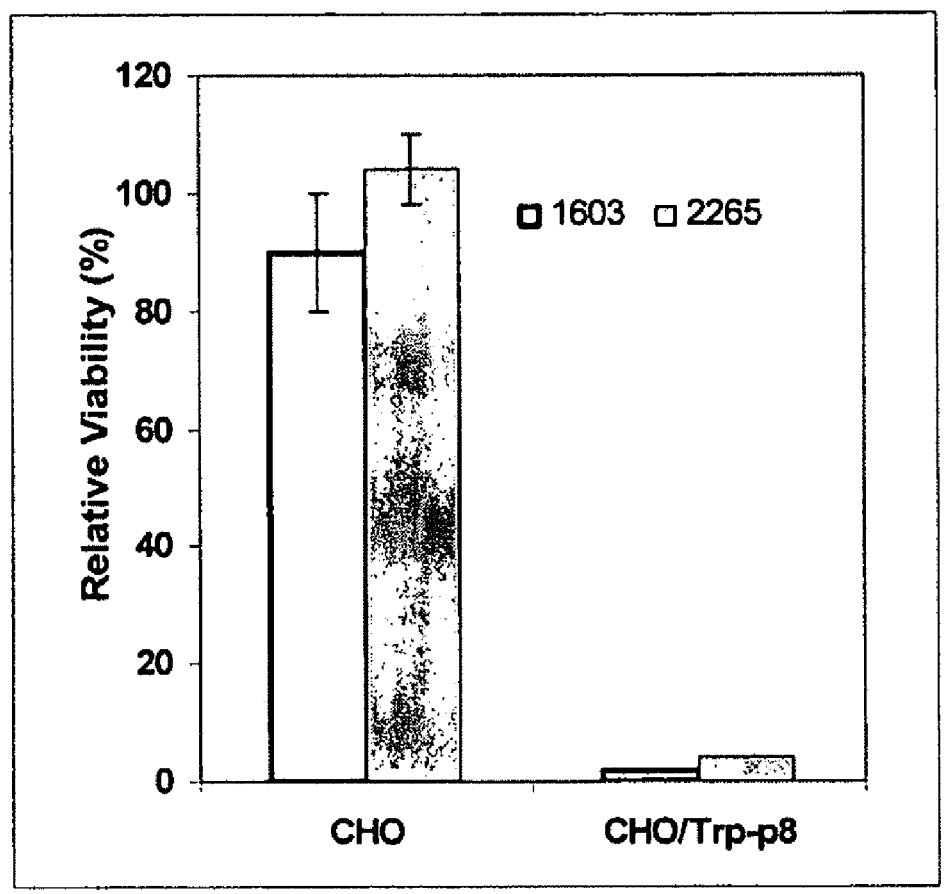
FIG. 1 is a graph depicting an exemplary ATP viability assay. Trp-p8 agonists were tested at 10 μM and agonist-specific killing of Trp-p8 expressing CHO cells (CHO/Trp-p8) measured at 37° C.

SEQ ID NO: 1 is the nucleotide sequence of a human Trp-p8 cDNA (GenBank Accession No. AY090109).

SEQ ID NO: 2 is the amino acid sequence encoded by the nucleotide sequence of SEQ ID NO: 1 (GenBank Accession No. NP_076985).

DETAILED DESCRIPTION OF THE INVENTION

The present invention is based upon the discovery that certain small-molecule agonists of Trp-p8 activity are capable of inhibiting the growth of and/or inducing apoptosis and/or necrosis in cells that express Trp-p8. Without wishing to be limited to any specific mode of action, it is believed that Trp-p8 agonist-mediated activation of the Trp-p8 receptor substantially increases cation influx, which is correlative of cellular toxicity. It is further believed that Trp-p8 antagonists can inhibit the basal level and/or native ligand-induced activity of endogenous Trp-p8 activation which, consequently, leads to reduced growth or death of cells expressing this cation channel protein.

Thus, the present invention provides small-molecule Trp-p8 modulators, including agonists and antagonists of Trp-p8 activity, as well as compositions, including pharmaceutical compositions, comprising one or more small-molecule Trp-p8 modulator in combination with one or more pharmaceutically acceptable carrier and/or excipient. The present invention also provides combination compositions comprising one or more Trp-p8 modulator and one or more additional therapeutic compound such as, for example, a cancer therapeutic agent. Trp-p8 modulators and compositions comprising Trp-p8 modulators will find utility in methods for activating Trp-p8-mediated cation influx in a cell, methods for inducing apoptosis and/or necrosis in a cell, as well as methods for the treatment of diseases associated with Trp-p8 expression including, but not limited to, cancers, such as breast, colon, lung, and prostate cancers.

DEFINITIONS

The term "Trp-p8 modulators" refers collectively to small-molecule agonists and antagonists that bind to and either increase or decrease, respectively, the activity of Trp-p8 in a cell. Trp-p8 agonists include compounds of Formula I, Formula II, Formula III, Formula N, Formula V, Formula VI, Formula VII, and Formula VIII and are exemplified herein by various compounds of Formulas I-VI, and chemical derivatives thereof. Trp-p8 antagonists include compounds of Formula I, Formula II, Formula III, Formula IV, Formula V, Formula VI, Formula VII, and Formula VIII and are exemplified herein by various compounds of Formulas VII-VIII, and chemical derivatives thereof. Additional Trp-p8 agonists or antagonists of Formula I, Formula II, Formula III, Formula IV, Formula V, Formula VI, Formula VII, and Formula VIII, not specifically exemplified herein, may be readily synthesized and characterized by a skilled artisan by employing the methodology expressly provided herein and/or as is readily available in the art.

The phrase "activate Trp-p8" means agonist-mediated activation of Trp-p8 expressed on the surface of a cell. For example, within certain embodiments, agonists of the present invention, when contacted with a cell and/or administered in vivo to a mammalian subject, activate Trp-p8 thereby facilitating the influx of cations, such as calcium ions, to such an intracellular level and/or for such a duration that is sufficient to cause toxicity to the cell as evidenced by a diminution in cell growth and/or an onset of necrotic and/or apoptotic cell death.

The term "aliphatic" is intended to include any straight-chained, branched-chained, or cyclic group free of aromatic unsaturation, and thus embraces alkyl, cycloalkyl, alkenyl, cycloalkenyl, alkynyl, hydroxyalkyl, acyloxyalkyl, alkoxy, alkoxyalkyl, aminoalkyl, acylaminoalkyl, carboxyalkyl, and similar combinations.

The term "alkyl," by itself or as part of another substituent, means, unless otherwise stated, a straight or branched chain, or cyclic hydrocarbon group, or combination thereof, which may be fully saturated, mono or polyunsaturated and can include di and multivalent groups, having the number of carbon atoms designated (i.e. $C_1$-$C_{10}$ means one to ten carbons). Examples of saturated hydrocarbon groups include groups such as methyl, ethyl, n-propyl, isopropyl, n-butyl, t-butyl, isobutyl, sec-butyl, cyclohexyl, (cyclohexyl)ethyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkenyl" denotes branched or unbranched hydrocarbon chains containing one or more carbon-carbon double bonds.

The term "alkynyl" refers to branched or unbranched hydrocarbon chains containing one or more carbon-carbon triple bonds.

The term "alkylene" by itself or as part of another substituent means a divalent group derived from an alkane, as exemplified by —$CH_2CH_2CH_2CH_2$—. Typically, an alkylene group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "cycloalkylene" by itself or as part of another substituent means a divalent group derived from a cycloalkane, as exemplified by cyclohexylene. Typically, a cycloalkylene group will have from 5-8 carbon atoms, with those groups having 6 carbon atoms being preferred in the present invention.

The term "alkenylene" by itself or as part of another substituent means a divalent group derived from an alkenyl, as exemplified by —CH═$CHCH_2CH_2$—. Typically, alkenylene groups will have from 2 to 24 carbon atoms, with those groups having 10 or fewer carbon atoms being preferred in the present invention.

The terms "alkoxy," "alkylamino" and "alkylthio" refer to those groups having an alkyl group attached to the remainder of the molecule through an oxygen, nitrogen or sulfur atom, respectively. Similarly, the term "dialkylamino" is used in a conventional sense to refer to —NR'R" wherein the R groups can be the same or different alkyl groups.

The term "heteroalkyl," by itself or in combination with another term, means, unless otherwise stated, a stable straight or branched chain, or cyclic hydrocarbon, or combinations thereof, fully saturated or containing from 1 to 3 degrees of unsaturation, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH═CH—O—$CH_3$, —Si($CH_3$)$_3$, —$CH_2$—CH═N—OCH—$_3$, and —CH═CH—N($CH_3$)—$CH_3$. Up to two heteroatoms may be consecutive, such as, for example, —$CH_2$—NH—$OCH_3$ and —$CH_2$—O—Si($CH_3$)$_3$. Also included in the term "heteroalkyl" are those groups described in more detail below as "heterocycloalkyl." The term "heteroalkylene" by itself or as part of another substituent means a divalent group derived from heteroalkyl, as exemplified by —$CH_2$—$CH_2$—S—$CH_2CH_2$— and —$CH_2$—S—$CH_2CH_2$—NH—$CH_2$—. For heteroalkylene groups, heteroatoms can also occupy either or both of the chain termini. Still further, for alkylene and heteroalkylene linking groups, no orientation of the linking group is implied.

The term "acyl" refers to those groups derived from an organic acid by removal of the hydroxy portion of the acid. Accordingly, acyl is meant to include, for example, acetyl, propionyl, butyryl, decanoyl, pivaloyl, benzoyl and the like.

An "activated carbonyl" group is a carbonyl group whose electrophilicity is enhanced as a result of the groups attached to either side of the carbonyl. Examples of such activated carbonyl groups are (polyfluoroalkyl)ketones, (polyfluoroalkyl)aldehydes, alpha-keto esters, alpha-keto acids, alpha-keto amides, 1,2-diketones, 2-acylthiazoles, 2-acylimidazoles, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "fluoroalkyl," are meant to include monofluoroalkyl and polyfluoroalkyl.

The term "aryl," employed alone or in combination with other terms (e.g., aryloxy, arylthioxy, arylalkyl) means, unless otherwise stated, an aromatic substituent which can be a single ring or multiple rings (up to three rings) which are fused together or linked covalently. The term "heteroaryl" is meant to include those aryl rings which contain from zero to four heteroatoms selected from N, O, and S, wherein the nitrogen and sulfur atoms are optionally oxidized, and the nitrogen atom(s) are optionally quaternized. The "heteroaryl" groups can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl ring systems are selected from the group of acceptable substituents described below. The term "arylalkyl" is meant to include those groups in which an aryl or heteroaryl group is attached to an alkyl group (e.g., benzyl, phenethyl, pyridylmethyl and the like) or a heteroalkyl group (e.g., phenoxymethyl, 2-pyridyloxymethyl, 3-(1-naphthyloxy)propyl, and the like).

Each of the above terms (e.g., "alkyl," "heteroalkyl" and "aryl") are meant to include both substituted and unsubstituted forms of the indicated group. Preferred substituents for each type of group are provided below.

Substituents for the alkyl and heteroalkyl groups (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R''', —OC(O)R', —C(O)R', —CO$_2$R', CONR'R", —OC(O)NR'R", —NR"C(O)R', —NR'—C(O)NR"R''', —NR"C(O)$_2$R', —NH—C(NH$_2$)=NH, —NR'C(NH$_2$)=NH, —NH—C(NH$_2$)=NR', —S(O)R', S(O)$_2$R', —S(O)$_2$NR'R", —CN and —NO$_2$ in a number ranging from zero to (2N+1), where N is the total number of carbon atoms in such group. R', R" and R''' each independently refer to hydrogen, unsubstituted (C$_1$-C$_8$) alkyl and heteroalkyl, unsubstituted aryl, aryl substituted with 1-3 halogens, unsubstituted alkyl, alkoxy or thioalkoxy groups, or aryl-(C$_1$-C$_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —CF$_3$ and —CH$_2$CF$_3$) and acyl (e.g., —C(O)CH$_3$, —C(O)CF$_3$, —C(O) CH$_2$OCH$_3$, and the like).

Similarly, substituents for the aryl groups are varied and are selected from: -halogen, —OR', —OC(O)R', —NR'R", —SR', —R', —CN, —NO$_2$, —CO$_2$R', —CONR'R", —C(O) R', —OC(O)NR'R", —NR"C(O)R', —NR"C(O)$_2$R', —NR'—C(O)NR"R''', —NH—C(NH$_2$)=NH, NR'C(NH$_2$) =NH, —NH—C(NH$_2$)=NR', —S(O)R', —S(O)$_2$R', —S(O)$_2$NR'R", —NR"—S(O)$_2$—R', —N$_3$, —CH(Ph)$_2$, perfluoro(C$_1$-C$_4$)alkoxy, and perfluoro(C$_1$-C$_4$)alkyl, in a number ranging from zero to the total number of open valences on the aromatic ring system; and where R', R" and R''' are independently selected from hydrogen, (C$_1$-C$_8$)alkyl and heteroalkyl, unsubstituted aryl, (unsubstituted aryl)-(C$_1$-C$_4$)alkyl, and (unsubstituted aryl)oxy-(C$_1$-C$_4$)alkyl.

Two of the substituents on adjacent atoms of the aryl ring may optionally be replaced with a substituent of the formula -T-C(O)—(CH$_2$)$_q$-U-, wherein T and U are independently —NH—, —O—, —CH$_2$— or a single bond, and the subscript q is an integer of from 0 to 2. Alternatively, two of the substituents on adjacent atoms of the aryl ring may optionally be replaced with a substituent of the formula -A-(CH$_2$)$_r$-B-, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl ring may optionally be replaced with a substituent of the formula —(CH$_2$)$_s$-X-(CH$_2$)$_t$—, where s and t are independently integers of from 0 to 3, and X is —O—, —NR'—, —S(O)—, —S(O)$_2$—, or —S(O)$_2$NR'—. The substituent R' in —NR'— and —S(O)$_2$NR'— is selected from hydrogen or unsubstituted (C$_1$-C$_6$)alkyl.

As used herein, the term "heteroatom" is meant to include oxygen (O), nitrogen (N), and sulfur (S).

The term "pharmaceutically acceptable salts" is meant to include salts of the active compounds of Formula I, Formula II, Formula III, Formula IV, Formula V, Formula VI, Formula VII, and/or Formula VIII that are prepared with relatively nontoxic acids or bases, depending on the particular substituents found on the compounds described herein. Examples of pharmaceutically acceptable base addition salts include, but are not limited to, sodium, potassium, calcium, ammonium, organic amino, magnesium salt, or other similar salt. Examples of pharmaceutically acceptable acid addition salts include, but are not limited to, those derived from inorganic acids like hydrochloric, hydrobromic, nitric, carbonic, monohydrogencarbonic, phosphoric, monohydrogenphosphoric, dihydrophosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like.

Small-Molecule Modulators of Trp-p8 Activity

Small-molecule Trp-p8 modulators that are suitably employed in the compositions and methods of the present invention are exemplified herein by the following Trop-p8 agonist compounds: Menthol (Sigma-Aldrich, Inc.; St. Louis, Mo.; (2-isopropyl-5-methyl-cyclohexanol)); Frescolat ML (Harris & Ford, LLC; Indianapolis, Ind.; Menthyl lactate); Frescolat MGA (Harris & Ford, LLC; Menthane Glycerin Acetal); L-Menthyl Acetate (Millenium Chemicals; Olympia Fields, Ill.; Cyclohexanol-5-methyl-2-(1-methylethyl)-acetate[1R-(1alpha,2beta,5 alpha)]-); L-Carvone (Millenium Chemicals; (R)-5-Isopropenyl-2-methyl-2-cyclohexenone p-Mentha-6,8-dien-2-one); WS-3 (Millenium Chemicals; N-Ethyl-p-menthane-3-carboxamide aka cyclohexanecarboxamide, N-ethyl-5-methyl-2(1-methylethyl)); Cooling Agent 10 (Takasago International Corp.; Rockleigh, N.J.; (1)-Menthoxypropane-1,2-diol); Coolact P® (Takasago International Corp.; (−)-Isopulegol); Coolact 38D' (Takasago International Corp.); Icilin (1-(2-hydroxyphenyl)-4-(3-nitrophenyl)-1,2,3,6-tetrahydropyrimidine-2-one aka 3,4-dihydro-3-(2-hydroxyphenyl)-6-(3-nitrophenyl)-(1H)-pyrimidin-2-one); WS-23 (2-Isopropyl-N,2,3-trimethylbutyramide aka N,2,3-trimethyl-2-isopropyl butamide), and WS-12 (N-

(4-methoxyphenyl)-p-menthan-3-carboxamide aka cyclohexanecarboxamide, N-(4-methoxyphenyl)-5-methyl-2(1-methylethyl)).

The present invention further contemplates that additional Trp-p8 agonists, including derivatives of the compounds of Formulas I, II, III, IV, V, VI, VII, and/or VIII disclosed herein, may also be suitably employed in the compositions and methods of the present invention.

Thus, in one embodiment, the present invention provides the following Trp-p8 modulators and derivatives thereof:

A compound of Formula I

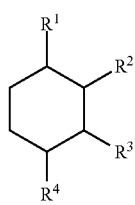

I wherein
$R^1$ is selected from the group consisting of H, OH, $CH_3$, $CH_3$—CH—$CH_3$ (isopropyl), and $CH_3$—C=$CH_2$ (isopropenyl);
$R^2$ is selected from the group consisting of H;
$R^3$ is selected from the group consisting of O, OH, acetate, lactate, carboxamide, butanamide, sulphanamide, and propanetriol; and
$R^4$ is selected from the group consisting of $CH_3$—CH—$CH_3$ (isopropyl), isopropane-2-ol, and $CH_3$—C=$CH_2$ (isopropenyl).

Exemplary compounds of Formula I include the following Trp-p8 agonists:

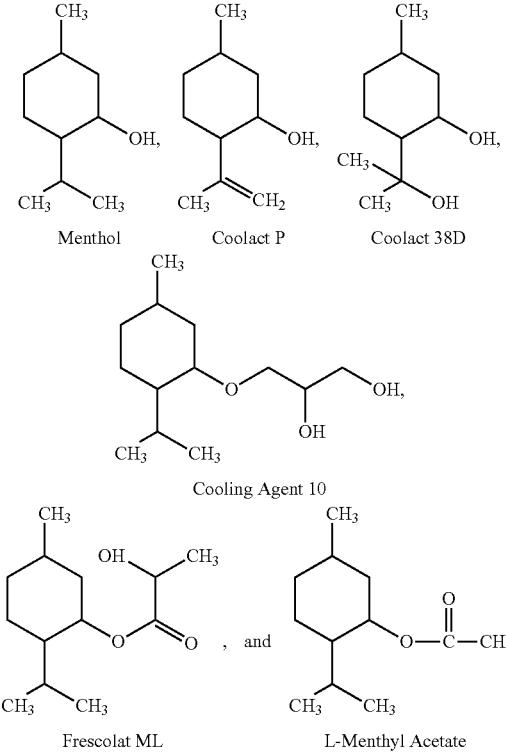

These exemplary Formula I Trp-p8 agonists have the following trade and chemical names: Menthol (2-isopropyl-5-methyl-cyclohexanol) (Sigma-Aldrich, Inc.; St. Louis, Mo.); Frescolat ML (Harris & Ford, LLC; Indianapolis, Ind.; Menthyl lactate); L-Menthyl Acetate (Millenium Chemicals; Olympia Fields, Ill.; Cyclohexanol-5-methyl-2-(1-methylethyl)-acetate-[1R-(1alpha,2beta, 5alpha)]-); Cooling Agent 10 (Takasago International Corp.; Rockleigh, N.J.; (1)-Menthoxypropane-1,2-diol); Coolact P® (Takasago International Corp.; (−)-Isopulegol); and Coolact 38D® (Takasago International Corp.).

In another embodiment, the present invention further provides the following small-molecule Trp-p8 modulators and derivatives thereof:

A compound of Formula II

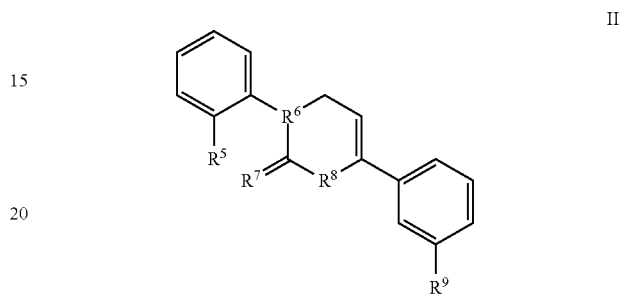

II wherein
$R^5$ is selected from the group consisting of H, OH, $CH_3$, $CH_3$—CH—$CH_3$ (isopropyl), and $CH_3$—C=$CH_2$ (isopropenyl);
$R^6$ is selected from the group consisting of N;
$R^7$ is selected from the group consisting of O and N;
$R^8$ is selected from the group consisting of NH, O, and S; and
$R^9$ is selected from the group consisting of $NO_2$.

Compounds of Formula II are exemplified herein by the Trp-p8 agonist Icilin (1-(2-hydroxyphenyl)-4-(3-nitrophenyl)-1,2,3,6-tetrahydropyrimidine-2-one aka 3,4-dihydro-3-(2-hydroxyphenyl)-6-(3-nitrophenyl)-(1H)-pyrimidin-2-one).

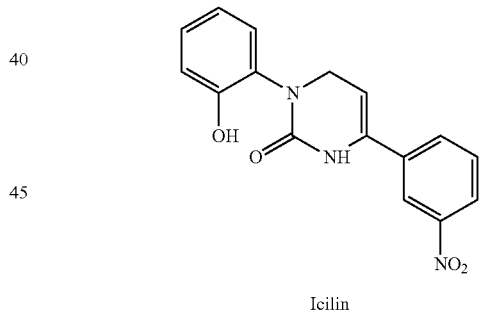

Icilin

In another embodiment, the present invention further provides the following acyclic carboxamide Trp-p8 modulators and derivatives thereof as presented in U.S. Pat. No. 4,153,679, incorporated herein by reference:

A compound of Formula III

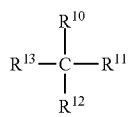

III wherein
$R^{10}$ is selected from the group consisting of H and a $C_1$-$C_5$ alkyl including, but not limited to, $CH_3$, $C_2H_5$, $CH_3$—CH—$CH_3$ (isopropyl), and $CH_3$—C=$CH_2$ (isopropenyl);

$R^{11}$ is selected from the group consisting of OH, carboxamide, butanamide, propanetriol, and CONR'R", wherein R' is selected from the group consisting of H, $CH_3$, $C_2H_5$, $C_4H_8$ (cyclobutyl), and $C_4H_8O$, and wherein R" is selected from the group consisting of $C_2H_5OOCH_2$, $C_2H_5$, $CH_3$—CH—$CH_3$ (isopropyl), $HOCH_2C(CH_3)_2$, $HOCH_2CH_2$, $C_4H_9$ (tertbutyl), $C_4H_9$ (secbutyl);

$R^{12}$ is selected from the group consisting of H and a $C_1$-$C_5$ alkyl including, but not limited to, $CH_3$, $CH_3$—CH—$CH_3$ (isopropyl), and $CH_3$—C=$CH_2$ (isopropenyl), $C_4H_9$ (secbutyl), $C_4H_9$ (isobutyl), $C_4H_9$ (n-butyl), $C_5H_{11}$ (isohexyl); and $R^{13}$ is selected from the group consisting of H and a $C_1$-$C_5$ alkyl including, but not limited to, $CH_3$, $C_2H_5$, $CH_3$—CH—$CH_3$ (isopropyl), $CH_3$—C=$CH_2$ (isopropenyl), $C_4H_9$ (secbutyl), $C_4H_9$ (isobutyl).

Compounds of Formula III are exemplified herein by the Trp-p8 agonist WS-23 (2-Isopropyl-N,2,3-trimethylbutyramide aka N,2,3-trimethyl-2-isopropyl butamide).

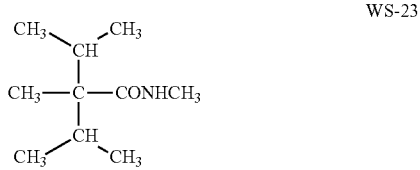

WS-23

In another embodiment, the present invention further provides the following 3-substituted-p-menthane Trp-p8 modulators and derivatives thereof as presented in U.S. Pat. No. 4,150,052, incorporated herein by reference:

A compound of Formula IV

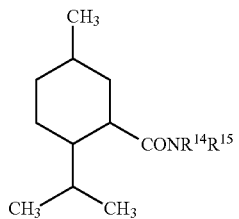

IV wherein $R^{14}$ is selected from the group consisting of H and an aliphatic group containing up to 25 carbon atoms;

$R^{15}$ is selected from the group consisting of H, OH and an aliphatic group containing up to 25 carbon atoms, with the proviso that when $R^{15}$ is H, $R^{14}$ may also be an aryl group of up to 10 carbon atoms and selected from the group consisting of substituted phenyl, phenalkyl, substituted phenalkyl, naphthyl, substituted naphthyl, and pyridyl; and $R^{14}$ and $R^{15}$, when taken together with the nitrogen atom to which they are attached, may form a cyclic or heterocyclic group of up to 25 carbon atoms, e.g., a piperidino or a morpholino group. Exemplary such cyclical groups may be selected from the group consisting of 3-phenyl-piperidin-1-yl, 3-phenyl-pyrrolidin-1-yl, 6,7-dimethoxy-1-methyl-3,4-dihydro-1H-isoquinolin-2-yl, and 4-pyrimidin-2-yl-piperazin-1-yl. Typical values for $R^{14}$ and $R^{15}$ when aliphatic are methyl, ethyl, propyl, butyl, isobutyl, n-decyl, cyclopropyl, cyclohexyl, cyclopentyl, cycloheptylmethyl, 2-hydroxyethyl, 3-hydroxy-n-propyl, 6-hydroxy-n-hexyl, 2-aminoethyl, 2-acetoxyethyl, 2-ethylcarboxyethyl, 4-hydroxybut-2-ynyl, and carboxymethyl.

When $R^{14}$ is aryl, typical values are benzyl, naphthyl, 4-methoxyphenyl, 2-methoxy-4-methoxyphenyl, 3-methoxy-5-methoxyphenyl, 4-methyl-5-chlorophenyl, 4-hydroxyphenyl, 4-methylphenyl, 3-methyl-4-methylphenyl, 3-hydroxy-4-methylphenyl, 4-fluorophenyl, 4-chlorophenyl, 4-bromophenyl, 4-ethylphenyl, 2-fluoro-4-fluorophenyl, 4-nitrophenyl, 2-hydroxynaphthyl, pyridyl, [1-carbamoyl-2-(1H-indol-3-yl)-ethyl, 1,3-dioxo-2,3-dihydro-1H-isoindol-4-yl, 1,3-dioxo-2,3-dihydro-1H-isoindol-5-yl, 1-carbamoyl-2-(4-hydroxyphenyl)ethyl, 1-carbamoyl-2-phenylethyl, 1-hydroxymethyl-2-(1H-indol-3-yl)ethyl, 1-hydroxymethyl-2-(4-chlorophenyl)ethyl, 1-hydroxymethyl-2-(4-hydroxyphenyl)ethyl, 1-hydroxymethyl-2-hydroxy-2-phenylethyl, 1-hydroxymethyl-2-phenyl ethyl, 1-methoxymethyl-2-phenylethyl, 1-methyl-2-(4-chlorophenyl)-ethyl, 1-methyl-2-(5-fluoro-1H-indol-3-yl)-ethyl, 1-methyl-2-hydroxy-2-phenylethyl, 1-oxo-2-phenylethyl, 1-phenyl-cyclopentylmethyl, 2-(1-cyclopentyl-pyrrolidin-3-yl)-ethyl, 2-(1H-indol-3-yl)ethyl, dimethoxyphenyl)ethyl, 2-(2,4-dichlorophenyl)ethyl, 2-(2,4-dimethylphenyl)ethyl, dimethoxyphenyl)ethyl, 2-(2,5-dimethylphenyl)-ethyl, 2-(2,6-dimethylphenyl)ethyl, 2-(2-chloro-6-fluorophenyl)ethyl, 2-(2-chlorophenyl)ethyl, 2-(2-fluorophenyl)ethyl, 2-(2-furyl)ethyl, 2-(2-methoxy-5-bromophenyl)ethyl, 2-(2-methoxyphenyl)-ethyl, 2-(2-methylphenyl)ethyl, 2-(3,4-dichlorophenyl)ethyl, 2-(3,4-dimethoxyphenyl)ethyl, dimethoxyphenyl)ethyl, 2-(3-bromo-4-methoxyphenyl)ethyl, 2-(3-chlorophenyl)ethyl, 2-(3-ethoxyphenyl)ethyl, 2-(3-fluorophenyl)ethyl, 2-(3-hydroxy-4-methoxyphenyl)-ethyl, 2-(3-hydroxyphenyl)ethyl, 2-(3-methoxy-4-ethoxyphenyl)ethyl, 2-(3-methoxy-4-hydroxyphenyl)ethyl, 2-(3-methoxyphenyl)ethyl, 2-(3-methylphenyl)ethyl, 2-(3-trifluoromethylphenyl)ethyl, 2-(4-bromophenyl)-ethyl, 2-(4-chlorophenyl)ethyl, 2-(4-ethylphenyl)ethyl, 2-(4-fluorophenyl)ethyl, 2-(4-hydroxyphenyl)ethyl, 2-(4-methoxy-phenyl)-2-oxo-ethyl, 2-(4-methoxyphenyl)ethyl, 2-(4-methylphenyl)ethyl, 2-(4-methylphenyl)ethyl, 2-(4-methylsulfanylphenyl)ethyl, 2-(4-nitrophenyl)ethyl, 2-(4-sulfamoyl-phenyl)-ethyl, 2-(5-methoxy-1H-indol-3-yl)-ethyl, 2-(6-fluoro-1H-indol-3-yl)-ethyl, 2-(6-methoxy-1H-indol-3-yl)-ethyl, 2-(7-methyl-1H-indol-3-yl)-ethyl, 2-(N,N-dipropylamino)ethyl, 2-(pyridin-2-yl)-ethyl, 2-(pyridin-3-yl)-ethyl, 2-(pyridin-4-yl)-ethyl, 2,2-diphenylethyl, 2,3-difluorobenzyl, 2,3-dimethoxyphenyl, 2,4-dichlorophenyl, 2,4-difluorophenyl, 2,4-dimethoxyphenyl, 2,4-dimethylphenyl, 2-bromo-4-methylphenyl, 2-chloro-4-cyanophenyl, 2-chloro-4-fluorophenyl, 2-chloro-4-iodophenyl, 2-chloro-4-nitrophenyl, 2-chloro-5-nitrophenyl, 2-chlorophenyl, 2-cyclohex-1-enyl-ethyl, 2-fluoro-4-chlorophenyl, 2-fluoro-5-nitrophenyl, 2-hydroxy-2-(3-hydroxyphenyl)ethyl, 2-hydroxy-2-(4-hydroxyphenyl)ethyl, 2-hydroxy-2-phenylethyl, 2-iodophenyl, 2-methyl-1,3-dioxo-2,3-dihydro-1H-isoindol-5-yl, 2-methyl-2-phenylethyl, 2-methyl-4-broophenyl, 2-methyl-5-nitrophenyl, 2-methylphenyl, 2-nitro-4-fluorophenyl, 2-nitrophenyl, 2-oxo-2,3-dihydro-1H-benzoimidazol-5-yl, 2-oxo-2-phenylethyl, 2-phenyl-1H-benzoimidazol-5-yl, 2-phenyl-2-(4-chlorophenyl)ethyl, 2-phenyl-2-(4-fluorophenyl)-ethyl, 2-phenyl-2-(4-methoxyphenyl)ethyl, 2-phenylethenyl, 2-phenylethyl, 2-pyridin-2-yl-benzooxazol-5-yl, 2-pyridin-3-yl-1H-benzoimidazol-5-yl, 2-thiophen-2-yl-ethyl), 2-trilfouromethyl-1H-benzoimidazol-5-yl, 3,4,5-trifluorophenyl, 3,4,5-trimethoxyphenyl, 3,4-cyclopentanephenyl, 3,4-dichlorophenyl, 3,4-dimethylphenyl, 3,5-dimethoxyphenyl, 3-acetamidophenyl, 3-bromo-4-methylphenyl, 3-carboxamidophenyl, 3-chloro-4-methoxyphenyl, 3-chloro-4-methylphenyl, 3-chloro-4-morpholin-4-yl-phenyl, 3-hydroxymethylphenyl, 3-nitrophenyl, 3-oxo-indan-5-yl, 3-phenylpropyl, 3-yl-acetophenone, 4-(1,1-dioxo-116-thiomorpholin-4-ylmethyl)-phenyl, 4-(1-hydroxyethyl)phenyl, 4-(2-hydroxyethyl)phenyl, 4-(4-ethyl-piperazin-1-yl)-phenyl, 4-(4-methyl-1H-benzoimidazol-2-yl)-phenyl, 4-(4-methyl-piperazin-1-ylmethyl)-phenyl, 4-(morpholine-4-sulfonyl)-phenyl, 4-[1,3-dioxo-2-(2-trifluoromethyl-phenyl)-2,3-dihydro-1H-isoindol-5-yloxy]-phenyl, 4-[2-(2-methoxy-phenyl)-1,3-dioxo-2,3-dihydro-1H-isoindol-5-yloxy]-phenyl, 4-{2-[2-(3,4-dimethoxy-phenyl)-ethyl]-1,3-dioxo-2,3-dihydro-1H-isoindol-5-yloxy}-phenyl, 4-acetylphenyl, 4-azepan-1-ylmethyl-phenyl, 4-benzooxazol-2-yl-phenyl, 4-Biphenyl, 4-bromophenyl, 4-carboxamidophenyl, 4-chlorophenyl, 4-cyanophenyl, 4-ethoxyphenyl, 4-ethylphenyl, 4-fluorophenyl, 4-hydroxymethylphenyl, 4-methoxyphenyl, 4-methyl-2-oxo-2H-chromen-7-yl, 4-methylcyclohexyl, 4-methylphenyl, 4-methylsulfanylphenyl, 4-nitrobenzyl, 4-pyrrolidin-1-ylmethyl-phenyl, 4-trifluoromethylphenyl, benzo[1,3]dioxol-5-yl, benzoylamino, benzyloxy, bicyclo[2.2.1]hept-2-yl, C-1H-indazol-5-yl, cycloheptyl, indan-2-yl, N-(2-diethylamino-ethyl)-benzamide-4-yl, N'-quinoxalin-2-yl-amino, and phenylcyclopropyl.

Trp-p8 modulators of Formula IV are exemplified herein by the Trp-p8 agonists WS-3 (Millenium Chemicals; N-Ethyl-p-menthane-3-carboxamide aka cyclohexanecarboxamide, N-ethyl-5-methyl-2(1-methylethyl)) and by WS-12 (N-(4-methoxyphenyl)-p-menthan-3-carboxamide aka cyclohexanecarboxamide, N-(4-methoxyphenyl)-5-methyl-2(1-methylethyl)), and the compounds presented in Table 1.

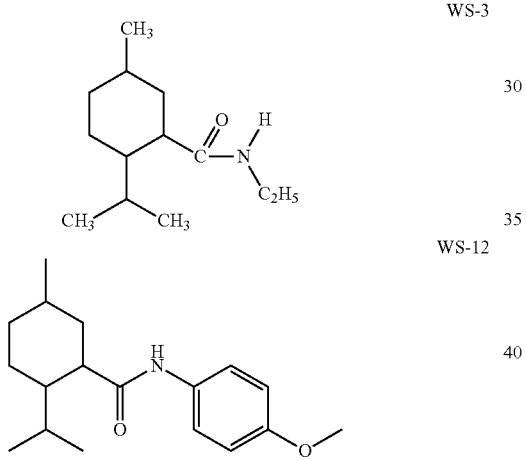

WS-3

WS-12

In a further embodiment, the present invention provides the following Trp-p8 modulators and derivatives thereof that comprise at least one ketal moiety, including, but not limited to the Trp-p8 agonists 1-menthone glycerol ketal and 3,3,5-trimethylcyclohexaone glycerol ketal presented in U.S. Pat. No. 5,266,592, incorporated herein by reference:

A compound comprising at least one ketal of Formula V

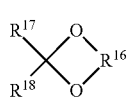

V wherein $R^{16}$ is selected from the group consisting of a $C_2$-$C_6$ alkylene group having at least one, but not more than 3, hydroxyl group(s), preferably 1 hydroxyl group, and Either $R^{17}$ and $R^{18}$ independently of one another represent $C_1$-$C_{10}$-alkyl which is optionally substituted by 1 to 3 groups selected from the group consisting of hydroxyl, amino, thio, and halogen (e.g., fluorine, chlorine, bromine, or iodine), $C_5$-$C_7$-cycloalkyl, preferably cyclohexyl, $C_6$-$C_{12}$-aryl, preferably phenyl, with the proviso that the total of the C atoms of $R^{17}$ and $R^{18}$ is not less than 3, or $R^{17}$ and $R^{18}$ together represent an alkylene group that, together with the carbon atom that carries the groups $R^{17}$ and $R^{18}$, forms a 5-7-membered ring, it being possible for this alkylene group, in turn, to be substituted by $C_1$-$C_6$-alkyl groups.

Preferred groups $R^{17}$ and $R^{18}$ comprise methyl, isopropyl, and tert-butyl.

Compounds comprising a ketal of Formula V include the following Trp-p8 modulator compounds wherein $R^{16}$ is as defined above:

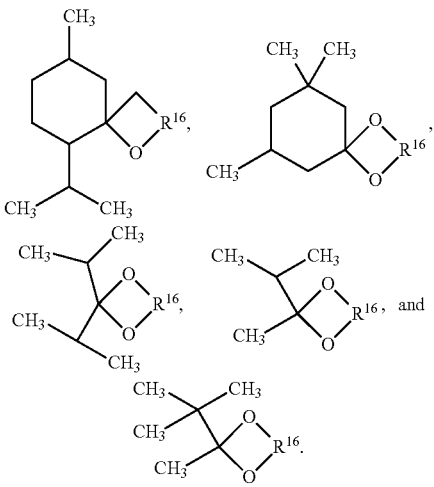

Compounds comprising a ketal of Formula V are exemplified herein by the Trp-p8 agonist Frescolat MGA (Harris & Ford, LLC; Menthone Glycerin Acetal),

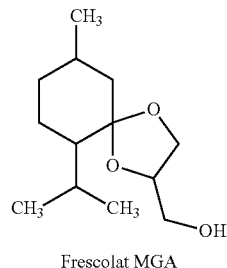 [SMILES: CC1CCC(C(C)C)C2(C1)OCC(CO)O2]

Frescolat MGA

In yet a further embodiment, the present invention provides Formula VI small-molecule Trp-p8 modulators and derivatives thereof exemplified herein by L-Carvone (Millenium Chemicals; (R)-5-Isopropenyl-2-methyl-2-cyclohexenone p-Mentha-6,8-dien-2-one),

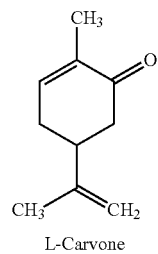

L-Carvone

Still further embodiments of the present invention provide small-molecule antagonists of the small-molecule Trp-p8 agonists presented herein. Thus, within certain embodiments are provided Formula I, Formula II, Formula III, Formula IV, Formula V, Formula VI, Formula VII, and/or Formula VIII small-molecule antagonists, and derivatives thereof, of the Formula I, Formula II, Formula III, Formula IV, Formula V, Formula VI, Formula VII, and/or Formula VIII Trp-p8 agonists disclosed herein above.

Presented herein in the Examples are specific Trp-p8 antagonists that are exemplary of the Trp-p8 modulators of Formula VII

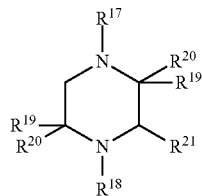

VII wherein

R$^{17}$ is selected from the group consisting of 2-pyridyl, 2-nitro-4-trifluoromethylphenyl, 2-nitro-4-chlorophenyl, 2-methoxyphenyl, 2-chlorophenyl, phenyl, 2-methyl-quinolin-3-yl, 4-methoxyphenyl, 4-fluorophenyl, 3-azepan1-yl-5-(4-trifluoromethoxy)phenylamino[1,3,5]triazyl, cyclohexyl, diphenylmethyl, 2-phenylethyl, 4-hydroxy-cyclohexyl, cycloheptyl, cyclopentyl, C-benzo91,3]-dioxol-5-yl-methyl, 2-pyridyl, and 4-chlorobenzyl;

R$^{18}$ is selected from the group consisting of 1-benzyl-1H-pyrazolo[3,4-d]pyrimidin-4-yl, 3-benzylamino-2-nitrophenyl, 5-nitro-quinolin-8-yl, 1-yl-3-(2-isopropyl-5-methyl-cyclohexyloxy)-propan-2-ol, 1-phenyl-1H-pyrazolo[3,4-d]pyrimidin-4-yl, benzyl-2-methyl-quinazolin-4-yl, 3-methyl-5-morpholin-4-yl-2-nitro-phenyl, 2-nitro-5-piperazin-1-yl-ethanol, 1-yl-3-(2-isopropyl-5-methyl-cyclohexyloxy)-propan-2-ol, 4-(2,5-dimethyl-pyrrol-1-yl)-2-nitro-phenyl, 2-nitro-3-trifluoromethanesulfonyl-phenyl, 1-phenyl-1H-pyrazolo[3,4-d]pyrimidin-4-yl, 2-(2-Fluoro-phenoxymethyl)-2-cyano oxazolyl, adamantly, 5-(benzo[1,3]dioxol-5-ylamino)-10b, 10c-dihydro-anthra[1,9-cd]isoxazol-6-one-yl, 2-methyl-thiazolo[3,2-b][1,2,4]triazol-6-ol 4-methylphenyl methyl, 3-benzyl-3H-quinazolin-4-one-2-yl, cyclopentyl, tetrahydronapthyl, cyclooctyl, cyclohexyl, C-[3-(4-chloro-phenyl)-2,5-dimethyl-pyrazolo[1,5-a]pyrimidin-7-yl]-methyl, C-(2-benzyl-5,6,7,8-tetrahydro-benzo[4,5]thieno[2,3-d]pyrimidin-4-yl)-methyl, and 1-yl-3-(2-isopropyl-5-methyl-cyclohexyloxy)-propan-2-ol;

R$^{19}$ and R$^{20}$ are each independently selected from the group consisting of H and O; and R$^{21}$ is selected from the group consisting of 4-methylphenyl, 2-chloro-4-fluorophenyl, and 4-chlorophenyl.

In other embodiments, the present invention provides Formula VIII small-molecule modulators, and derivatives thereof, including Formula VIII antagonists of the Formula IV Trp-p8 agonists disclosed herein above and in the Examples.

A compound of Formula VIII

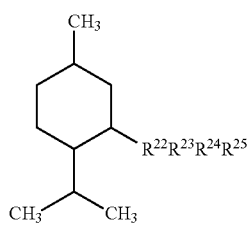

VIII wherein

R$^{22}$ is a linker moiety, which may be selected from the group consisting of oxyacetamide, urea, carbamate, thiourea, sulfonamide, amine, amide. Formula VIII antagonists are represented by the following sub-formulae (Formula VIII-A, Formula VIII-B, Formula VIII-C, Formula VIII-D, Formula VIII-E, Formula VIII-F, and Formula VIII-G):

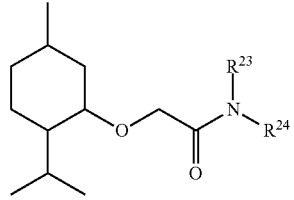

VIII-A

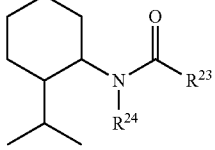

VIII-B

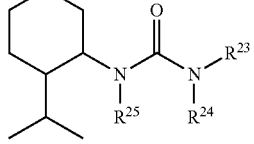

VIII-C

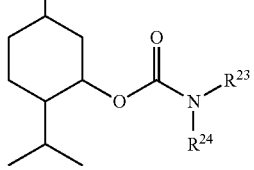

VIII-D

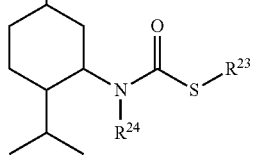

VIII-E

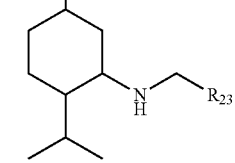

VIII-F

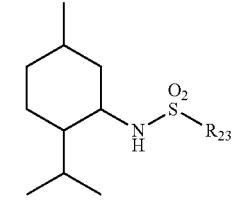

VIII-G

Irrespective of which of the seven R$^{22}$ linker moieties is employed, R$^{23}$ is selected from the group consisting of H, tetrahydro isoquinolinyl, tetrahydro quinolinyl, 3-methyl indolinyl, indolinyl, 2-(N-methyl, N-phenylethyl)amino ethyl, 3-methyl indolinyl, 1-phenyl ethyl, 2-chloro benzyl, 2-methoxybenzyl, 2-methoxyphenyl, 2-cyclohex-1-enyl ethyl, (1-phenyl-cyclophentyl)-methyl, 2-(tetrahydroquinolinyl)-ethyl, 1-propyl-1,2,3,4-tetrahydro-pyrrolo[1,2-a]pyrazine, cycloheptyl, 3-cyclohexylsulfanylpropyl, 2-cyclohex-1-enyl ethyl, 2-(N-isopropyl, N-phenylethyl)amino ethyl, 1-methyl-1,2,3,4-tetrhydro-pyrrolo[1,2-a]pyrazine, 2-cyclopentylethyl, 2-phenylcyclopropyl, 1-phenoxyethyl, 4-butyloxyphenyl, (2-nitrophenoxy)methyl, 4,7,7-trimethyl-2-oxa-bicyclo[2.2.1]heptan-3-one, C-(1-phenyl-5-propyl-1H-pyrazol-4-yl)-methyl, benzyl, 2-chlorobenzyl, 1-[3-(6,7-dimethoxy-1-methyl-3,4-dihydro-1H-isoquinolin-2-ylmethyl)-4-methoxy-phenyl]-2,3,4,9-tetrahydro-1H-b-carboline, C-[3-(4-butoxy-phenyl)-1H-pyrazol-4-yl]-methyl, 4-(azepane-1-sulfonyl)-phenyl, and 5-(7-chloro-quinolin-4-ylsulfanyl)-[1,3,4]thiadiazol-2-yl;

$R^{24}$ is selected from the group consisting of H, tetrahydro isoquinolinyl, tetrahydro quinolinyl, 3-methyl indolinyl, indolinyl, 3-methyl indolinyl, 1-propyl-1,2,3,4-tetrahydro-pyrrolo[1,2-a]pyrazine, 1-methyl-1,2,3,4-tetrhydro-pyrrolo[1,2-a]pyrazine, and 1-(3-(6,7-dimethoxy-1-methyl-3,4-dihydro-1H-isoquinolin-2-ylmethyl)-4-methoxy-phenyl]-2,3,4,9-tetrahydro-1H-b-carboline; and $R^{25}$ is selected from the group consisting of H.

Synthesis of Small-Molecule Trp-p8 Modulators

As noted above, compounds of the present invention include compounds of Formula I, Formula II, Formula III, Formula IV, Formula V, Formula VI, Formula VII, and Formula VIII. Within certain aspects, compounds of the present invention can be obtained from commercial sources and/or can be made using commercially available starting materials by employing synthetic methodology readily available in the art. Compounds of Formulae I-VIII may be isolated using typical isolation and purification techniques known in the art, including, for example, chromatographic and recrystallization methods.

Exemplary compositions and methodology for their synthesis are disclosed in the following patents, each of which is incorporated herein by reference: U.S. Pat. No. 4,150,052 discloses N-substituted p-menthane 3-carboxyamide compounds having a physiological cooling action on the skin; U.S. Pat. No. 4,153,679 discloses compositions comprising acyclic tertiary and secondary carboxamides that have a physiological cooling action on the skin; U.S. Pat. No. 4,020,153 discloses cyclic sulphonamides and sulphinamides having a physiological cooling action on the skin; European Patent Application No. 1 157 617 discloses alpha-keto enamine derivatives in a variety of food, cosmetic, pharmaceutical, and perfume compositions; U.S. Pat. No. 4,296,093 discloses alkyl substituted cyclohexanamides having a physiological cooling effect on the skin; U.S. Pat. No. 5,756,857 discloses cyclohexanol derivatives having a cool feeling; U.S. Pat. No. 4,248,859 discloses alicyclic amides having a physiological cooling effect; U.S. Pat. No. 5,266,592 discloses ketals, such as glycerol ketals, for example 1-menthone glycerol ketal or 3,3,5-trimethylcyclohexanone glycerol ketal, that have a physiological cooling effect; U.S. Pat. No. 6,328,982 discloses compositions comprising a cooling compound such as 1-menthol (2-isopropyl-5-methyl-cyclohexanol), 1-isopulegol, 3-(1-menthoxy)propane-1,2-diol and p-menthane-3,8-diol; and U.S. Pat. No. 4,459,425 discloses 3-1-menthoxypropane-1,2-diol and its associated cooling activity.

Those of skill in the art will readily recognize that compounds suitably included in the compositions and methods of the present invention can exist in a number of cis and trans isomers, E/Z forms, diastereomers, as well as optical isomers. Thus, compounds used in the compositions and methods of the present invention include all such combinations and variations.

In compounds of Formula I, Formula II, Formula III, Formula IV, Formula V, and Formula VI carbon atoms to which four non-identical substituents are bonded are asymmetric. Accordingly, compounds of Formula I, Formula II, Formula III, Formula IV, Formula V, or Formula VI may exist as enantiomers, diastereomers or a mixture thereof. The enantiomers and diastereomers may be separated by chromatographic or crystallization methods, or by other methods known in the art. The asymmetric carbon atom may be in one of two configurations, R or S, both of which are within the scope of the present invention. The presence of small amounts of the opposing enantiomer or diastereomer in the final purified product does not affect the therapeutic application of such compounds.

Compounds of Formulae I-W may be further treated to form pharmaceutically acceptable salts. Treatment of a compound of the invention with an acid or base may form, respectively, a pharmaceutically acceptable acid addition salt and a pharmaceutically acceptable base addition salt, each as defined above. Various inorganic and organic acids and bases known in the art, including those described herein above, may be used to effect the conversion to the salt.

The present invention also relates to pharmaceutically acceptable isomers, hydrates, and solvates of compounds of Formula I, Formula II, Formula III, Formula IV, Formula V, and Formula VI. Compounds of these formulae may also exist in various isomeric and tautomeric forms including pharmaceutically acceptable salts, hydrates and solvates of such isomers and tautomers.

This invention also encompasses prodrug derivatives of the compounds of Formula I, Formula II, Formula III, Formula IV, Formula V, and Formula VI. The term "prodrug" refers to a pharmacologically inactive derivative of a parent drug molecule that requires biotransformation, either spontaneous or enzymatic, within the organism to release the active drug. Prodrugs are variations or derivatives of the compounds of Formulae I-VI of the present invention that have groups cleavable under metabolic conditions. Prodrugs become the compounds of the invention which are pharmaceutically active in vivo when they undergo solvolysis under physiological conditions or undergo enzymatic degradation. An exemplary prodrug technology that may be suitably employed with the compounds of the present invention is the protease activated cancer therapy (PACT) technology described in detail within U.S. patent application Ser. No. 10/156,214 and PCT Application Publication No. WO 02/095007, both of which are incorporated herein by reference.

Synthesis of compounds of Formula I, may be achieved, as described below in reference to compounds of Formula IV, by reacting an acid chloride, obtained by reacting p-menthane-3-carboxylic acid with thionyl chloride, with the appropriate amine. As noted below, typically, the reaction is carried out in solution at room temperature in the presence of a hydrogen chloride receptor (e.g., sodium hydroxide).

Synthesis of (1)-Menthoxypropane-1,2-diol (Cooling Agent 10) from l-menthol (2-isopropyl-5-methyl-cyclohexanol) is described in U.S. Pat. No. 4,459,425, incorporated herein by reference. Briefly, 1-menthol and metallic sodium or sodium hydride are introduced into a solvent (e.g., toluene or xylene) and heated. When the temperature reaches 100° C., or higher, the reaction starts and generation of hydrogen gas occurs. After confirming that the generation of hydrogen has stopped, the mixture is further heated at the reflux temperature of the solvent to complete the reaction.

Allyl halide (e.g., allyl chloride or allyl bromide) is then added to the reaction mixture in small portions. As the reaction proceeds, sodium halide deposits and the reaction solution becomes slurry-like. After the reaction is completed, the reaction solution is cooled, and after addition of water, the resulting mixture is stirred. Then, a solvent, (e.g., benzene, toluene, ether, hexane, or petroleum ether) is added. The organic layer is separated and washed with saturated saline water. After the solvent is recovered, the residue is distilled under reduced pressure to obtain 3-1-menthoxypropate-1-ene.

The 3-1-menthoxypropane-1-ne is oxidized into the corresponding oxide by use of an organic peracid. The oxide is hydrolyzed to form the desired 3-1-methoxypropane-1,2-diol. That is, an organic acid, (e.g., formic acid or acetic acid) and aqueous hydrogen peroxide are mixed with 3-1-menthoxypropane-1-ene and gradually heated carefully while stirring. The organic acid and the hydrogen peroxide react, forming an organic peracid that participates in the oxidation reaction. The reaction is exothermic, and rapid heating should be avoided. When the temperature of the reaction solution reaches near 50° C., the heating is stopped. It is, thereafter, necessary for the temperature of the reaction solution to be maintained at about 70° C. by external cooling to prevent a further temperature increase caused by the heat of reaction. If the temperature of the reaction solution is excessively high, the organic peracid decomposes before it participates in the oxidation reaction, resulting in a reduction in yield.

After the reaction is completed, a solvent (e.g., benzene, toluene, xylene, or petroleum ether) is added to perform the extraction. The extracted liquid is washed with water. Upon recovery of the solvent by distillation, a crude oxide in the form of an organic acid ester is produced. The crude oxide thus formed is mixed with an about 20% aqueous solution or caustic soda, for example, and is hydrolyzed by boiling for about 1 hour to produce the desired 3-1-menthoxypropane-1,2-diol.

Synthesis of compounds of Formula II, exemplified herein by 1-(2-hydroxyphenyl)-4-(3-nitrophenyl)-1,2,3,6-tetrahydropyrimidine-2-one (Icilin aka AG-3-5), is disclosed in U.S. Pat. No. 3,821,221, incorporated herein by reference. Briefly, β-diethlyamino-m-nitropropiophenone hydrochloride is added to 50% aqueous ethanol and the mixture refluxed with stirring until the hydrochloride is dissolved. O-aminophenol is added and the solution refluxed for 30 minutes, then set aside to cool. The reaction product is crystallized out of solution to yield 3-(o-hydroxyanilino)-m-nitrophropiophenone (mp of 107° C. to 109° C.). β-(o-hydroxyanilino)-m-nitrophropiophenone is dissolved in ethanol and concentrated HCl is added to acidify the solution. The solvent is evaporated in vacuo and β-(o-hydroxyanilino-m-nitropropiophenone)-HCl (mp of 172° C. to 173° C.) is crystallized from methanol-acetone. β-(o-hydroxyanilino-m-nitropropiophenone)-HCl is dissolved in acetic acid at 60° C. Potassium cyanate is added and the reaction mixture cooled to room temperature. Water is added and the crystalline 1-(2-hydroxyphenyl)-4-(3-nitrophenyl)-1,2,3,6-tetrahydropyrimidine-2-one (mp of 228° C. to 230° C.) is recovered by filtration.

Synthesis of acyclic carboxamide compounds of Formula III, as exemplified herein by 2-isopropyl-N,2,3-trimethylbutyramide aka N,2,3-trimethyl-2-isopropyl butamide (WS-23), is disclosed in U.S. Pat. No. 4,153,679, incorporated herein by reference. Briefly, Formula III amides may be prepared by conventional techniques known to those of skill in the art, for example, by reacting an acid chloride of the formula $R_{10}R_{12}R_{13}COCl$ with an amine ($R_{11}$), as indicated above, in the presence of hydrogen chloride acceptor. N,2,3-trimethyl-2-isopropyl butamide may be prepared, for example, by heating 2,3-Dimethyl-2-isopropylbutanic acid under reflux with thionyl chloride for 60 minutes. The excess of thionyl chloride may be removed under reduced pressure and the 2,3-dimethyl-2-isopropylbutanoyl chloride distilled, bp. 73° C.-75° C./15 mm.

The acid chloride in ether may be added dropwise to a stirred solution of methylamine (70% soln. in water) in ether with stirring. The ether layer may then be washed with water, dilute HCl and water. The dried ($MgSO_4$) ether solution was concentrated, and the residue distilled to give N,2,3-trimethyl-2-isopropyl butamide (mp 58° C.-61° C., bp. 83° C.-85° C./0.35 mm.).

Synthesis of exemplary 3-substituted-p-menthane compounds that may be suitably employed as Trp-p8 modulators in the compositions and methods of the present invention is described in U.S. Pat. No. 4,150,052, incorporated herein by reference in its entirety. For example, the corresponding acid chloride (obtained by reacting p-menthane-3-carboxylic acid with thionyl chloride) may be reacted with the appropriate amine. The reaction will usually be carried out at room temperature in solution in the presence of a hydrogen chloride receptor, e.g., sodium hydroxide.

The basic p-menthane structure is a chair-shaped molecule that can exist in cis or trans form. Substitution of the carboxyl or amide group into the 3-position gives rise to four configurational or geometric isomers depending upon whether the substitution is axially or equatorially into the cis or trans isomer, the four isomers are related as menthol is to neomenthol, isomenthol, and neoisomenthol.

In an exemplary reaction protocol, p-Menthane-3-carboxylic acid is heated under reflux with thionyl chloride. Excess thionyl chloride is distilled off in vacuo. The crude p-menth-3-oyl chloride is dissolved in diethyl ether and the ethereal solution added with stirring and cooling to a solution of ethylamine and sodium hydroxide in water. The mixture is stirred and the ethereal layer separated. The aqueous layer is washed with ether and the combined ethereal solution washed with dilute hydrochloric acid and water. The ether solution is dried with $MgSO_4$ and evaporated to give a white crystalline solid. The solid is recrystallised from acetone:water (9:1) by dissolving the crystals at room temperature and then cooling to produce N-ethyl-p-menthane-3-carbozamide as a white crystalline solid, mp. 82.5° C.-84.5° C. Substitution of the amide group in the 3-position of the p-menthane structure gives rise to optical and geometric isomerism.

When either $R^{13}$ or $R^{14}$ is aliphatic, the preferred values are $C_1$-$C_9$ straight or branched chain alkyl, $C_1$-$C_9$ straight or branched chain hydroxyalkyl or aminoalkyl and $C_1$-$C_4$ acylated derivatives thereof, and $-C_nH_{2n}COR^{15}$ or $-C_nH_{2n}COOR^{15}$, where $-C_nH_{2n}$ is a straight or branched chain alkylene in which n is an integer of from 1-6 and $R^{15}$ is H or a $C_1$-$C_8$ alkyl or hydroxyalkyl group, preferably a $C_1$-$C_4$ straight chain alkyl group.

When $R^{13}$ is H and $R^{14}$ is OH or substituted phenyl, e.g., alkylphenyl, hydroxyphenyl, alkoxyphenyl, halophenyl of up to 10 carbon atoms, phenalkyl or substituted phenalkyl, e.g., benzyl, naphthyl, or substituted naphthyl, and compounds where $R^{13}$ and $R^{14}$ are joined to form a cyclic group. When so joined, $R^{13}$ and $R^{14}$ preferably represent an alkylene chain, optionally interrupted by oxygen, which together with the nitrogen atom to which $R^{13}$ and $R^{14}$ are attached forms a 5- or 6-membered heterocyclic ring.

Synthesis of exemplary compounds comprising one or more ketal, including for example menthone glycerine ketals, that may be suitably employed as Trp-p8 modulators in the compositions and methods of the present invention is described in U.S. Pat. No. 5,266,592, incorporated herein by reference in its entirety.

For example, ketals of Formula V may be prepared by an acid-catalysed reaction of a ketone on which the ketal of Formula V is based and not less than the equivalent amount of aliphatic $C_3$-$C_6$-alcohol having not less than 3 and not more than 5, preferably 3, hydroxyl groups. The ketone on which the ketal of Formula V is based and an excess amount of the $C_3$-$C_6$ alcohol having 3 to 5 hydroxyl groups will be employed.

Exemplary acid catalysts that can be used are p-toluenesulphonic acid, phosphoric acid, or potassium hydrogen sulphate in catalytically effective amounts. The reaction will generally be carried out either in an organic solvent that together with water forms an azeotrope, so that the water, which is liberated during formation of the ketal, can be eliminated by azeotropic entrainment or water-consuming co-reagents such as, for example, trialkyl ortho esters are used. Exemplary organic solvents include benzene, toluene, xylene, chloroform, methylene chloride and trichloroethylene. The reaction is complete when water no longer separates out or when the ester/alcohol mixture is no longer separated out. The products may be washed subsequently with dilute alkali and with water, to separate and dry the organic phase, to strip off the solvent and, if appropriate, to purify the residue, for example by distillation.

An exemplary compound comprising a ketal of Formula V is 1-menthone glycerol ketal (Frescolat MGA, aka menthone glycerin acetal; Harris & Ford, LLC), which is synthesized as follows. 2 mol of 1-menthone, 3 mol of glycerol, and 5 g of potassium hydrogen sulphate are mixed in a 2 liter three-neck flask in the presence of toluene. This mixture is refluxed in a water separator. After 7 hours, water separates and the mixture is neutralized and distilled.

Synthesis of the exemplary Formula VI terpene compound L-Carvone (2-cyclohexen-1-one, 2-methyl-5-(1-methylethenyl)-(R); Millenium Chemicals) from D-limonene is described in Ikan, *Natural Products—A Laboratory Guide* pp. 151-155 (Academic Press, 1969), incorporated herein by reference. Briefly, a solution of D-limonene in isopropanol is cooled to below 10° C. Solutions of HCl in isopropanol and concentrated aqueous sodium nitrite are added dropwise to the D-limonene solution to generate limonene nitrosochloride. The limonene nitrosochloride and dimethylformamide is refluxed with isopropanol. After cooling, crystallization is induced and the precipitate filtered and washed with water. The resulting L-carvoxime is refluxed with 0.5 M oxalic acid and the mixture is steam distilled. The distillate is extracted with ether, dried over anhydrous magnesium sulfate, and the excess ether evaporated to leave L-carvone.

Additional synthetic methods for the preparation of Trp-p8 modulators of the present invention are presented herein in Examples 1-5.

Compositions Comprising a Small-Molecule Trp-p8 Modulators

As discussed above, the present invention is directed to small-molecule Trp-p8 modulators, including Trp-p8 agonists and Trp-p8 antagonists that bind to and alter the activity of Trp-p8. Within certain embodiments, Trp-p8 modulators are agonists that are, in certain instances, capable of stimulating cation influx in, and toxicity of, a cell expressing the Trp-p8 channel protein. Within alternative embodiments, Trp-p8 modulators are antagonists of Trp-p8 activity that are capable of reducing the activity of Trp-p8 expressed in a cell. Thus, Trp-p8 modulators of the present invention will find utility in compositions, including pharmaceutical compositions, which are useful in the treatment of diseases associated with Trp-p8 expression. Suitable compositions, according to the present invention, comprise one or more Trp-p8 agonist of Formula I, Formula II, Formula III, Formula IV, Formula V, Formula VI, Formula VII, and/or Formula VIII and/or one or more Trp-p8 antagonist of Formula I, Formula II, Formula III, Formula IV, Formula V, Formula VI, Formula VII, and/or Formula VIII, as described above, in combination with one or more pharmaceutically acceptable carrier or excipient.

In one embodiment, the present invention provides small-molecule Trp-p8 modulators in combination with a pharmaceutically acceptable excipient such as sterile saline or other medium, water, gelatin, oil, etc., to form pharmaceutically acceptable compositions. The compositions and/or agonists may be administered alone or in combination with any convenient carrier, diluent, etc. and such administration may be provided in single or multiple dosages. Useful carriers include, but are not limited to, solid, semi-solid, or liquid medium including water and non-toxic organic solvents.

Pharmaceutical compositions of the present invention may be prepared by mixing one or more Trp-p8 agonist of Formula I, Formula II, Formula III, Formula IV, Formula V, Formula VI, Formula VII, and/or Formula VIII with a pharmaceutically acceptable carrier or agent. Alternatively, pharmaceutical compositions may be prepared by mixing one or more Trp-p8 antagonist of Formula I, Formula II, Formula III, Formula IV, Formula V, Formula VI, Formula VII, and/or Formula VIII with a pharmaceutically acceptable carrier or agent. In addition, pharmaceutical compositions may further include excipients, stabilizers, diluents and the like and may be provided in sustained release or timed release formulations. Acceptable carriers, agents, excipients, stabilizers, diluents and the like for therapeutic use are well known in the pharmaceutical field, and are described, for example, in "Remington's Pharmaceutical Sciences," (Mack Publishing Co., ed. A. R. Gennaro, 1985), incorporated herein by reference. Such materials are nontoxic to the recipients at the dosages and concentrations employed and include buffers such as phosphate, citrate, acetate, and other organic acid salts, antioxidants such as ascorbic acid, low molecular weight peptides such as polyarginine, proteins, such as serum albumin, gelatin, or immunoglobulin, hydrophilic polymers such as serum albumin, gelatin, or immunoglobulin, hydrophilic polymers such as polyvinylpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium and/or nonionic surfactants such as TWEEN, or polyethyleneglycol.

Within still further aspects, the compositions of the present invention comprise a compound of Formula I, Formula II, Formula III, Formula IV, Formula V, Formula VI, Formula VII, and/or Formula VIII formulated together with one or more cancer therapeutic agent. Alternatively, the compositions of the present invention comprise a compound of Formula I, Formula II, Formula III, Formula IV, Formula V, Formula VI, Formula VII, and/or Formula VIII independently formulated with one or more cancer therapeutic agent. That is, the compound of Formula I, Formula II, Formula III, Formula IV, Formula V, Formula VI, Formula VII, and/or Formula VIII and the cancer therapeutic agent are separately formulated.

Suitable cancer therapeutic agents include, but are not limited to, antimitotic agents including, but not limited to, paclitaxel, vincristine, and etoposide; alkylating agents including, but not limited to, mechlorethamine, cyclophosphamide, and carmustine; antimetabolites including, but not limited to, methotrexate, gemcitabine, lometrexol, 5-fluorouracil, and 6-mercaptopurine; cytotoxic antibiotics including, but not limited to, doxorubicin, daunorubicin, bleomycin, mitomycin C, and streptozocin; platinum agents including, but not limited to, cisplatin and carboplatin; hormonal agents including, but not limited to, anti-estrogens such as tamoxifen and diethylstilbestrol as well as anti-androgens such as flutamide; antiangiogenesis agents; and farnesyl transferase inhibitors.

In certain aspects, compounds of Formula I, Formula II, Formula III, Formula IV, Formula V, Formula VI, Formula VII, and/or Formula VIII are administered in combination with a cancer therapeutic agent that is ineffective in stimulating Trp-p8-mediated cation influx.

In other aspects, compounds of Formula I, Formula II, Formula III, Formula IV, Formula V, Formula VI, Formula VII, and/or Formula VIII are administered in combination with one or more additional Trp-p8 modulator including, but not limited to a compound of Formula I, Formula II, Formula III, Formula IV, Formula V, Formula VI, Formula VII, and/or Formula VIII.

Depending upon the particular treatment regimen contemplated, pharmaceutical compositions of the present invention may be administered parenterally, topically, orally, or locally. In certain aspects, the pharmaceutical compositions are administered parenterally, e.g., intravenously, subcutaneously, intradermally, or intramuscularly. In one embodiment, the present invention provides compositions for parenteral administration that comprise a compound of the present invention, dissolved or suspended in a carrier such as an aqueous carrier.

For solid formulations, compounds may be admixed with conventional nontoxic solid carriers such as, for example, pharmaceutical grades of mannitol, lactose, starch, magnesium stearate, sodium saccharin, talcum, cellulose, glucose, sucrose, magnesium carbonate, and the like.

For aerosol administration, compounds of the present invention may be supplied in finely divided form along with a nontoxic surfactant and propellant. Exemplary such agents are the esters or partial esters of fatty acids containing from 6 to 22 carbon atoms, such as caproic, actanoic, lauric, palmitic, stearic, linoleic, olesteric, and oleic acids.

Compositions of the present invention may be administered by injection, i.e. intravenously, intramuscularly, intracutaneously, subcutaneously, introaduodenally, or intraperitoneally. Alternatively, compositions may be administered by inhalation, such as intranasally, and may be administered transdermally, such as through a patch or the like.

It will be understood that the actual preferred formulation of compositions, including pharmaceutical compositions, will vary according to the mode of administration as well as the particular disease being treated. The optimal formulations and modes of administration will be routinely determined on a disease by disease and patient by patient basis by those of skill in the art.

Methods for Identifying and Characterizing the In vitro and In Vivo Efficacy of Small-molecule Modulators of Trp-p8

As discussed above, the present invention is directed to small-molecule Trp-p8 modulators, including agonists and antagonists of Trp-p8 activity. Disclosed herein are Trp-p8 modulators exemplified by the compounds of Formula I, Formula II, Formula III, Formula IV, Formula V, Formula VI, Formula VII, and/or Formula VIII described herein above. The present invention further contemplates that additional Trp-p8 modulators may also be suitably employed in the compositions and methods of the present invention.

Additional or alternative Trp-p8 agonists and antagonists may be identified by the methodology disclosed in the accompanying Examples. For instance, Trp-p8 agonists having efficacy in the treatment of disease(s) associated with Trp-p8 expression include small molecules that result in one or more of the following: (1) inhibit the growth or decrease the viability of a cell expressing Trp-p8; (2) stimulate calcium and/or other cation influx in a cell expressing Trp-p8; (3) induction of apoptosis and/or necrosis in a cell expressing Trp-p8; and/or (4) efficacy in one or more animal model systems of human disease. Trp-p8 antagonists having efficacy in the treatment of disease(s) associated with Trp-p8 expression include small molecules that that result in one or more of the following: (1) protect Trp-p8 expressing cells from toxic effect of agonists in in vitro model system (2) inhibit growth of and/or kill cancer cell line with endogenous Trp-p8 expression (3) are efficacious in one or more animal model systems of human disease.

Thus, within certain embodiments, the present invention provides methods for identifying Trp-p8 agonists comprising the step of contacting a Trp-p8 expressing cell with a candidate Trp-p8 agonist for a time and in an amount sufficient to inhibit the growth and/or decrease the viability of a Trp-p8 expressing cell, wherein the inhibited growth and/or reduced viability indicate that the candidate Trp-p8 agonist is capable of activating Trp-p8 expressed by the cell.

Other embodiments provide methods for identifying Trp-p8 agonists, comprising the step of contacting a Trp-p8 expressing cell with a candidate Trp-p8 agonist for a time and in an amount sufficient to induce influx of calcium and/or other cations into the cell, wherein increased cation influx is correlative of increased cellular toxicity.

Still further embodiments provide methods for identifying Trp-p8 agonists comprising the step of administering a candidate Trp-p8 agonist to an animal having one or more neoplastic cell that expresses Trp-p8 for a time and in an amount sufficient to inhibit the growth of and/or induce apoptosis and/or necrosis in the cell thereby increasing the survival of the animal, wherein any one or more of inhibition of cell growth, induction of apoptosis, induction of necrosis, and/or increased survival of the animal indicate efficacy of the Trp-p8 agonist.

The present invention provides methods for the identification of Trp-p8 antagonists in addition to the Trp-p8 antagonists disclosed herein by the compounds of Formula VII and Formula VIII. Such method include (1) in vitro assay systems for detecting the protection of Trp-p8 expressing cells from toxicity induced by Trp-p8 agonists; (2) in vitro and in vivo assay systems of detecting the inhibition of growth of a cancer cell and/or cancer cell line endogenously expressing Trp-p8; (3) in vivo animal model systems whereby one or more candidate Trp-p8 antagonist is administered to an animal having one or more neoplastic cell that expresses Trp-p8 for a time and in an amount sufficient to inhibit the growth of and/or induce apoptosis and/or necrosis in the cell thereby increasing the survival of the animal.

Methods for Use of Trp-p8 Modulators

Small-molecule Trp-p8 modulators of the present invention may be suitably employed in methods for modifying (i.e.

activating or reducing) Trp-p8-mediated calcium influx in a cell and therapeutic methods for the treatment of one or more diseases associated with expression of Trp-p8. For example, and as noted above, it has been observed that abnormal Trp-p8 expression is associated with a neoplastic phenotype in a variety of cancerous tissues including breast, colon, lung, and prostate tissues. Tsavaler et al., Cancer Research, supra.

Thus, within certain embodiments are provided methods for activating Trp-p8-mediated calcium influx in a cell, such methods comprising the step of contacting the Trp-p8 expressing cell with an amount of a Trp-p8 agonist for a time sufficient to inhibit growth of the cell and/or to induce necrosis and/or apoptosis in the cell. Exemplary methods for activating Trp-p8 are provided within the Examples presented herein.

Other embodiments of the present invention provide therapeutic methods for the treatment of diseases associated with expression of Trp-p8, such methods comprising the step of administering to a mammal, typically a human, a therapeutically effective amount of a composition comprising a Trp-p8 agonist for a time sufficient to inhibit growth of the cell and/or to induce necrosis and/or apoptosis in the cell. As used herein, the phrase "therapeutically effective amount" refers to the amount of a compound that, when administered to a mammal for treating a disease, is sufficient to effect such treatment for the disease. The "therapeutically effective amount" will vary depending upon the compound, the disease, and its severity and the age, weight, etc., of the mammal to be treated.

As used herein, the terms "treat", "treating", and "treatment" include: (1) preventing the disease, i.e. causing the clinical symptoms of the disease not to develop in a mammal that may be predisposed to the disease but does not yet experience any symptoms of the disease; (2) inhibiting the disease, i.e. arresting or reducing the development of the disease or its clinical symptoms; or (3) relieving the disease, i.e. causing regression of the disease or its clinical symptoms.

While the frequency and dosage of treatment regimens will vary depending upon such factors as the disease and patient treated, compositions comprising one or more compound of Formula I, Formula II, Formula III, Formula IV, Formula V, Formula VI, Formula VII, and/or Formula VIII are typically administered in the range of about 0.001 mg compound/kg body mass to about 100 mg/kg. Typically, treatment is initiated with smaller dosages that are less than the optimum dose of the compound. Thereafter, the dosage may be increased until optimal effectiveness is achieved.

In most instances, administration of a composition(s) of the present invention is achieved by any method that ensures systemic exposure to the compound of Formula I, Formula II, Formula III, Formula IV, Formula V, Formula VI, Formula VII, and/or Formula VIII. Thus, compositions may be administered orally, parenterally, intraduodenally, and intranasally. Typically, such compositions comprise one or more such compound in combination with one or more pharmaceutically acceptable carrier or diluent, as described in further detail herein above.

Other embodiments of the present invention provide combination therapies wherein one or more compound of Formula I, Formula II, Formula III, Formula IV, Formula V, Formula VI, Formula VII, and/or Formula VIII is administered in conjunction with one or more cancer therapeutic agent, as described in further detail herein above, such as an antimitotic agent, an alkylating agent, an antimetabolite, a cytotoxic antibiotic, a platinum agent, a hormonal agent, and/or an antiandrogen. Still further embodiments of the present invention provide combination therapies wherein two or more compounds of Formula I, Formula II, Formula III, Formula IV, Formula V, Formula VI, Formula VII, and/or Formula VIII are administered either simultaneously or sequentially to achieve the desired therapeutic outcome.

Thus, as used herein, the term "combination" means that at least two compounds can be delivered in a simultaneous manner, in combination therapy wherein the first compound is administered first, followed by the second compound, as well as wherein the second compound is delivered first, followed by the first compound. The desired result can be either a subjective relief of a symptom(s) or an objectively identifiable improvement in the recipient of the dosages.

The following examples are offered by way of illustration and not by way of limitation.

EXAMPLES

Example 1

Synthesis of Menthane-3-carboxamide Compounds

This example discloses methodology for the synthesis of menthane-3-carboxamide Trp-p8 modulators.

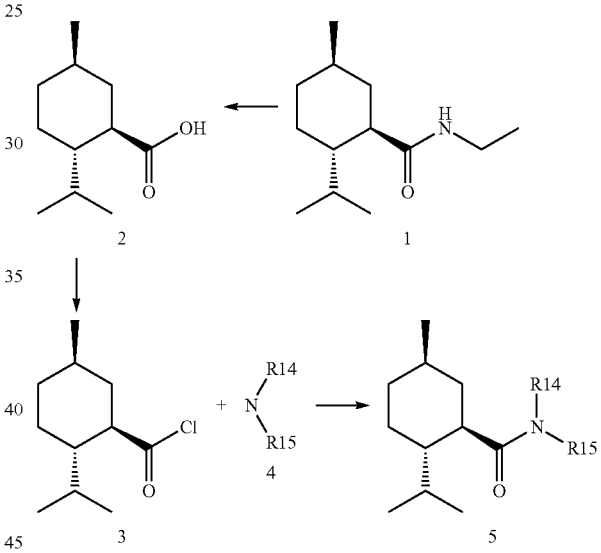

Menthane-3-carboxylic acid (2). Water (300 ml) was placed in a 2-L Erlenmeyer flask with a large stir bar. Sulfuric acid (500 ml) was added carefully with stirring. The solution was allowed to cool to 75° C., and N-ethyl-p-menthane-3-carboxamide (1, 62.5 g) was added. The temperature was maintained at 75° C. with a hot plate, and sodium nitrite (31 g) was added carefully. Two more 31 gram portions of $NaNO_2$ were added at 1-hour intervals, and the mixture was stirred overnight at 75° C.

The mixture was cooled to room temperature, diluted with ~1 L of ice water, and extracted with ~500 ml of ether. The ether layer was separated, washed with water, and extracted with 2×350 ml of 1M NaOH. The aqueous layer was made acidic with concentrated HCl and extracted with ether. The ether layer was dried with $MgSO_4$ and evaporated to give menthane-3-carboxylic acid (33.2 g, 61%) as a crystalline solid, [□]=−50.3 deg (c=1, $CHCl_3$, 25° C.).

Menthane-3-carbonyl chloride (3). Menthane-3-carboxylic acid (54.35 g) was refluxed with 80 ml of thionyl chloride for 3 hours. The $SOCl_2$ was removed by distillation, and the acid chloride was distilled at 114-115° C. (8 Torr). (Lit. b.p. 84-85° C. at 3.5 Torr). Yield: 50 g (84%).

General procedure for preparation of menthane-3-carboxamides (5). To a stirred solution of 0.2 mmol of the amine (4) in 1 ml of acetonitrile or NMP and 0.4 mmol of DIPEA was added 0.022 ml of menthane-3-carbonyl chloride (1). The reaction mixture was shaken for 3 hours. For less reactive amines, the mixture was heated (60° C.) and shaken for 24 hours. The product was purified from the crude reaction mixture by HPLC (40-95% gradient over 10 minutes using 0.05% TFA in CH$_3$CN and 0.05% TFA in H$_2$O) and evaporated to dryness.

Example 2

Synthesis of Menthol Acetamide and Carbamate Compounds

This example discloses methodology for the synthesis of Menthol Acetamide and Carbamate Trp-p8 modulators.

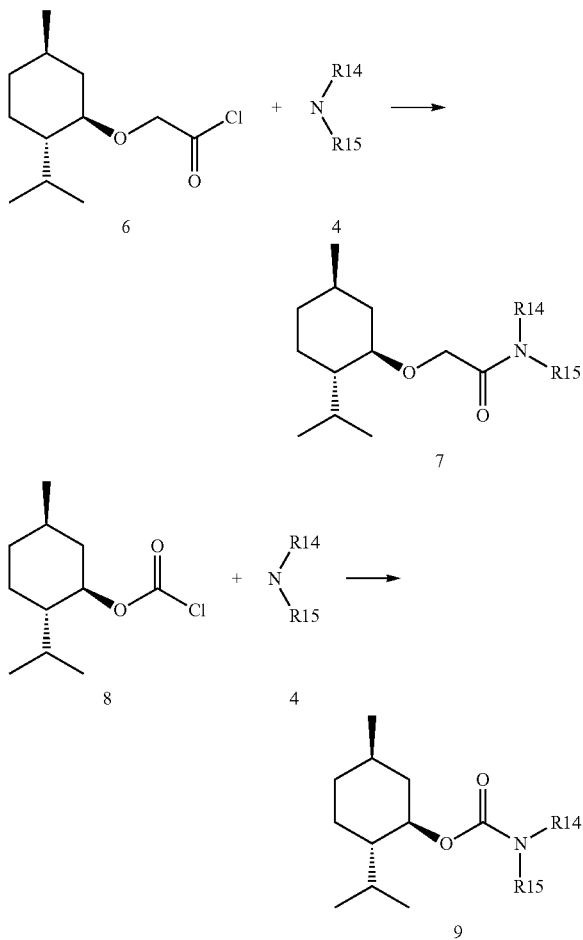

General procedures for the preparation of menthol acetamides (7) and menthol carbamates (9). To a two-phase ether-water system containing 0.07 mmol of amine (4) in 1 ml of ether and 1 ml of 0.1 M aqueous sodium hydroxide was added 0.1 mmol of acid chloride (6) or chloroformate (8). The reaction mixture was shaken for 2-3 hours. The upper layer was removed and evaporated to dryness to afford the product.

Example 3

Synthesis of Menthol-3-urea and Menthyl-3-thiourea Compounds

This example discloses methodology for the synthesis of Menthyl-3-urea and Menthyl-3-thiourea Trp-p8 modulators.

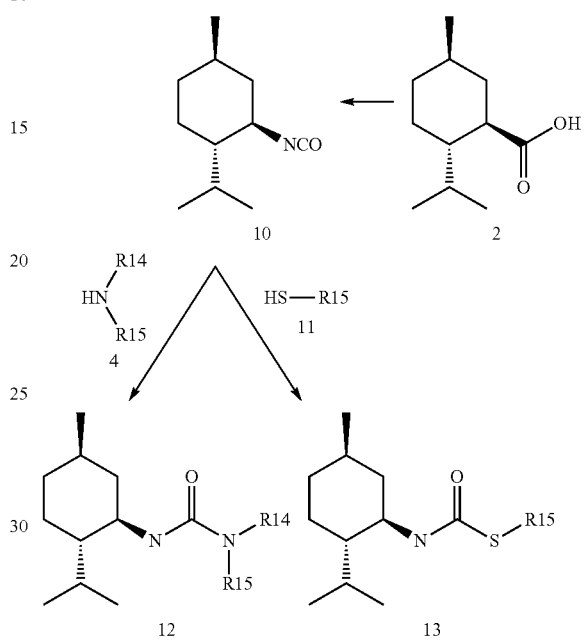

Menthyl-3-isocyanate (10). To an ice-cooled solution of menthane-3-carboxylic acid (4 g, 22 mmol) and triethylamine (3.05 ml, 22 mmol) in dry DMF (45 ml) was added diphenylphosphoryl azide (4.72 ml, 22 mmol). The mixture was stirred at 0° C. for 2 hours and at room temperature for 3 hours, then poured into a mixture of ether and ice water. The ether layer was separated and washed with aqueous sodium bicarbonate, dried with MgSO$_4$, and evaporated. The residue was distilled (85° C., 10 Ton) to give menthyl-3-isocyanate (2.9 g, 73%) as a colorless liquid.

General procedure for the preparation of menthyl-3-ureas (12) and menthyl-3-thioureas (13). To a stirred solution of 0.07 mmol of the amine (4) or thiol (11) in 1 ml of dry ethyl acetate was added a solution of 0.07 mmol of menthyl-3-isocyanate in 0.5 ml of ethyl acetate. The reaction mixture was shaken overnight then evaporated to dryness to afford the product.

Example 4

Synthesis of Menthane-3-amide, Menthane-3-sulfonamide and Menthane-3-carbamate Compounds This example discloses methodology for the synthesis of Menthane-3-amide, Menthane-3-sulfonamide and Menthane-3-carbamate Trp-p8 modulators.

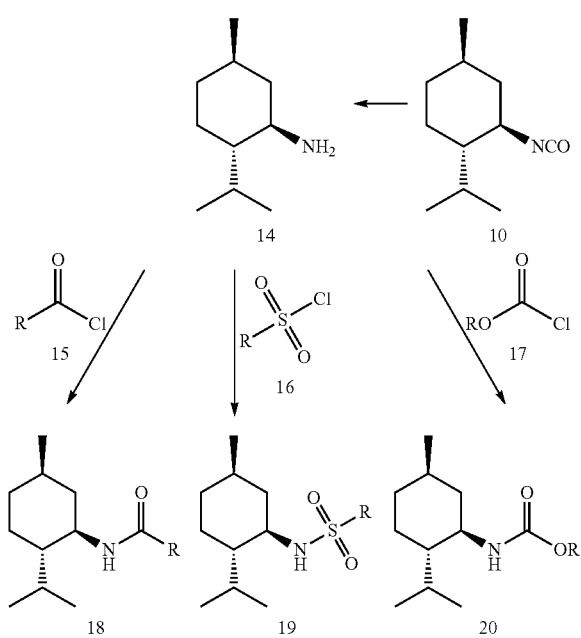

Menthyl-3-amine hydrochloride (14). To a vigorously stirred mixture of diethyl ether (100 ml) and 6N aqueous hydrochloric acid (100 ml) was added menthyl-3-isocyanate (2.0 g, 11 mmol), and the mixture was stirred overnight at room temperature. The aqueous phase was separated, made basic with an excess of aqueous sodium hydroxide, and extracted with ether. The ether phase was dried with $MgSO_4$ and filtered. An excess of anhydrous HCl (3M) in ethanol was added, and a precipitate immediately formed. Filtration gave menthylamine hydrochloride (1.9 g, 90%) as fine white crystals.

General procedure for the preparation of menthane-3-amides (18), menthane-3-sulfonamides (19) and menthane-3-carbamates (20). A solution of menthyl-3-amine hydrochloride (0.078 mmol) in 0.7 ml of water was added to a solution of the acid chloride, sulfonyl chloride, or chloroformate (0.078 mmol) in 1 ml $Et_2O$, followed by the addition 0.3 ml of 0.5 M NaOH. The mixture was shaken at room temperature for 12-18 hours. The $Et_2O$ layer was then separated and the solvent removed under reduced pressure to afford the product.

Example 5

Synthesis of Menthyl-3-amine Compounds

This example discloses methodology for the synthesis of Menthyl-3-amine Trp-p8 modulators.

General Procedures for the Preparation of Menthyl-3-amines (23).

Method 1

A mixture of the amine (22, 0.1 mmol) and 15.4 mg (0.1 mmol) of menthone (21) in 1 ml of 1,2-dichloroethane was treated with sodium triacetoxyborohydride (32 mg, 0.15 mmol). The mixture was stirred for 24 h (periodically monitored by LCMS). The reaction mixture was quenched by adding 1N NaOH (1 ml) and the product was extracted with ether. The extract was washed with brine, dried ($MgSO_4$) and evaporated to dryness to afforf the product.

Method 2

A mixture of menthyl-3-amine (0.1 mmol) and 15.4 mg (0.1 mmol) of aldehyde (24) in 1 ml of 1,2-dichloroethane was treated with sodium triacetoxyborohydride (32 mg, 0.15 mmol). The mixture was stirred for 24 h (periodically monitored by LCMS). The reaction mixture was quenched by adding 1N NaOH (1 ml) and the product was extracted with ether. The extract was washed with brine, dried ($MgSO_4$) and evaporated to dryness.

Example 6

Expression of Trp-p8 in CHO Cells

Human trp-p8 transfected CHO cells (referred to herein as CHO/Trp-p8) were generated for use in experiments of the present invention. Expression of Trp-p8 polypeptide in this transfectant and the absence of any endogenous expression in the non-transfected CHO was confirmed by western blot and immunofluorescence using a Trp-p8 specific antibody (GS2.20; disclosed within copending U.S. patent application Ser. No. 10/_____, incorporated herein by reference in its entirety) as well as the calcium flux assay with Icilin (1-[2-hydroxyphenyl]-4-[3-nitrophenyl]-1,2,3,6-tetrahydro-pyrimidine-2-one) and menthol (2-isopropyl-5-methyl-cy-clohexanol). Non-transfected CHO cells were used to establish the specificity of the effects of the compounds observed with CHO/Trp-p8.

Example 7

Trp-p8-mediated Decrease in Cell Viability Following Exposure of CHO/Trp-p8 Cells with Candidate Trp-P8 Agonist Compounds at 37° C.

This Example discloses an ATP viability assay suitable for screening for effective Trp-p8 agonists. The ATP viability assay described herein employs CHO cells expressing an exogenous Trp-p8 cDNA. This example further establishes that Trp-p8 agonists of the present invention are effective in decreasing the viability of Trp-p8 expressing cells.

The concentration of intracellular ATP declines very rapidly when metabolically active cells undergo necrosis and/or

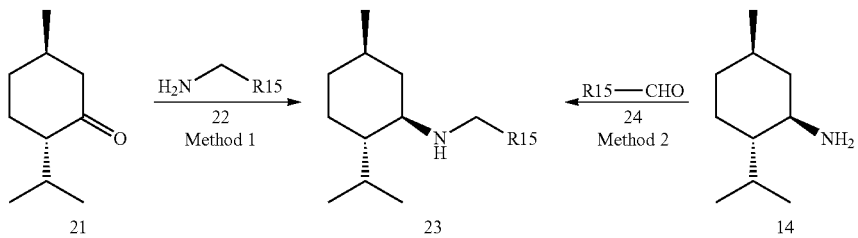

apoptosis. The ATP concentration and consequently the relative cell viability can be measured by established methods using commercially available reagents. In the agonist screening methodology disclosed herein, a compound that specifically decreases the viability of CHO/Trp-p8 cells is referred to as an agonist.

As a primary screen for efficacy and specificity for agonists, both the non-transfected CHO and CHO/Trp-p8 cells were exposed to 10 μM of test compounds in 1% dimethylsulfoxide (DMSO) or 1% DMSO (control) in a 96-well black walled, black-bottomed, cell-culture treated plate. DMSO was the solvent for all of the compounds tested. After 24-26 hours at 37° C., the cells were lysed and ATP concentration determined via a chemiluminescence assay using a commercially available reagent kit—Cell Titer-Glo (Promega; Madison, Wis.). Relative viability (%), expressed as the ATP level in cells treated with compounds expressed as a percentage of ATP levels in cells treated with the DMSO alone, was a measure of the agonist activity of the candidate compound—the lower the % viability, the more potent the Trp-p8 agonist. $EC_{50}$ values were determined for the most active candidate Trp-p8 agonists at 37° C. by measuring viability at 8-10 agonist concentrations. ($EC_{50}$ is defined herein as the agonist concentration at which there is a 50% reduction in cell viability).

Exemplary Trp-p8 Agonists of Formula IV that were efficacious in the ATP viability assay are presented herein in Table 1. Table 1A presents Formula IV Trp-p8 agonists exhibiting an $EC_{50}$ value within the range of 0.05 to 0.20 μM; Table 1B presents Formula IV Trp-p8 agonists exhibiting an $EC_{50}$ value within the range of 0.20 to 0.50 μM; Table 1C presents Formula IV Trp-p8 agonists exhibiting an $EC_{50}$ value within the range of 0.50 to 1.00 μM; and Table 1D presents Formula IV Trp-p8 agonists exhibiting an $EC_{50}$ value within the range of 1.00 to 7.00 μM.

Viability of CHO/Trp-p8 cells following treatment with exemplary Trp-p8 agonists is presented in FIG. 1.

TABLE 1A

Exemplary Trp-p8 Agonists of Formula IV
Exhibiting an $EC_{50}$ Value within the Range of 0.05 to 0.20 μM

| Ref. No.: | Chemical Structure | $R^{14}/R^{15}$ | $R^{15}$ |
|---|---|---|---|
| 2905 | 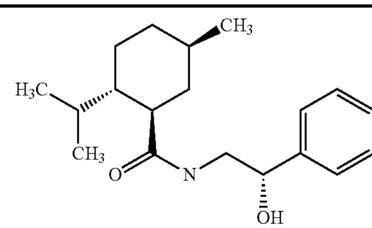 | | 2-hydroxy-2-phenylethyl |
| 3012 | 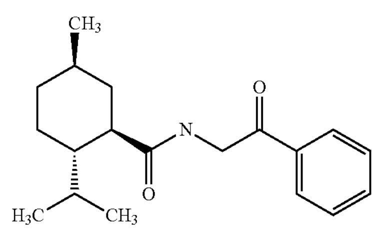 | | 2-oxo-2-phenylethyl |
| 2896 | 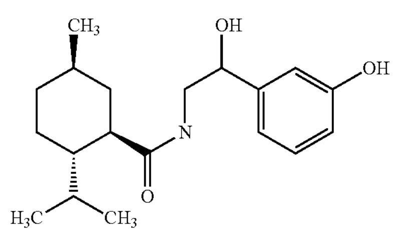 [SMILES: CC(C)[C@@H]1CC[C@@H](C)C[C@H]1C(=O)NCC(O)c1cccc(O)c1] | | 2-hydroxy-2-(3-hydroxyphenyl)ethyl |
| 3006 | 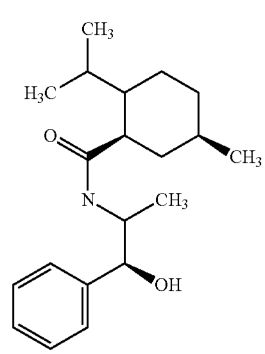 [SMILES: CC(C)C1CC[C@@H](C)C[C@H]1C(=O)NC(C)[C@@H](O)c1ccccc1] | | 1-methyl-2-hydroxy-2-phenylethyl |

TABLE 1A-continued

Exemplary Trp-p8 Agonists of Formula IV
Exhibiting an $EC_{50}$ Value within the Range of 0.05 to 0.20 μM

| Ref. No.: | Chemical Structure | $R^{14}/R^{15}$ | $R^{15}$ |
|---|---|---|---|
| 2926 | 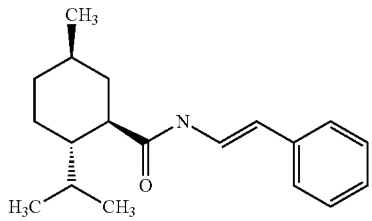 [SMILES: CC(C)[C@@H]1CC[C@@H](C)C[C@H]1C(=O)N/C=C/c1ccccc1] | | 2-phenylethenyl |
| 3014 | 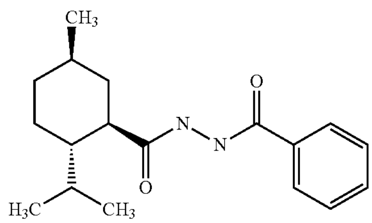 [SMILES: CC(C)[C@@H]1CC[C@@H](C)C[C@H]1C(=O)NNC(=O)c1ccccc1] | | Benzoylamino |
| 2963 | 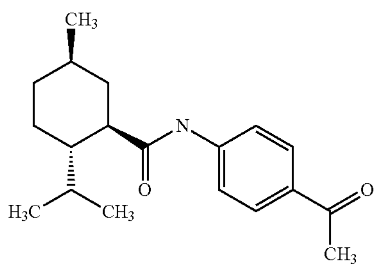 [SMILES: CC(=O)c1ccc(NC(=O)[C@@H]2C[C@H](C)CC[C@H]2C(C)C)cc1] | | 4-acetylphenyl |

TABLE 1B

Exemplary Trp-p8 Agonists of Formula IV
Exhibiting an $EC_{50}$ Value within the Range of 0.20 to 0.50 μM

| Ref. No.: | Chemical Structure | $R^{14}/R^{15}$ | $R^{15}$ |
|---|---|---|---|
| 3024 | 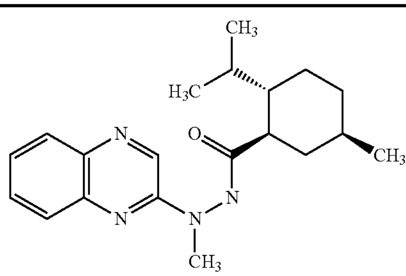 | | N'-quinoxalin-2-yl-amino |
| 2913 | 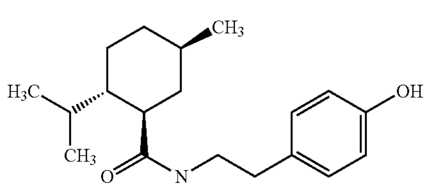 [SMILES: CC(C)[C@@H]1CC[C@@H](C)C[C@H]1C(=O)NCCc1ccc(O)cc1] | | 2-(4-hydroxyphenyl)ethyl |

TABLE 1B-continued

Exemplary Trp-p8 Agonists of Formula IV
Exhibiting an $EC_{50}$ Value within the Range of 0.20 to 0.50 μM

| Ref. No.: | Chemical Structure | $R^{14}/R^{15}$ | $R^{15}$ |
|---|---|---|---|
| 2897 | 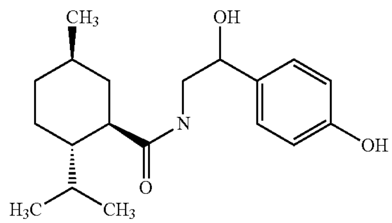 [SMILES: CC(C)[C@@H]1CC[C@@H](C)C[C@H]1C(=O)NCC(O)c1ccc(O)cc1] | | 2-hydroxy-2-(4-hydroxyphenyl)ethyl |
| 2928 | 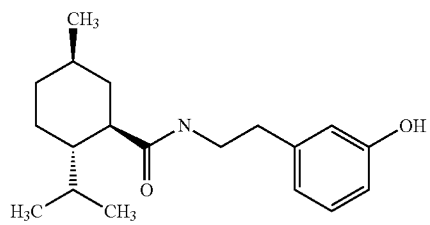 | | 2-(3-hydroxyphenyl)ethyl |
| 2901 | 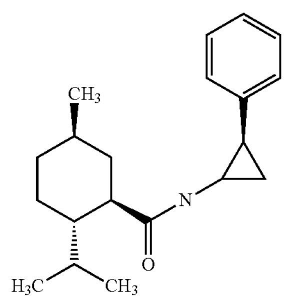 [SMILES: CC(C)[C@@H]1CC[C@@H](C)C[C@H]1C(=O)NC1C[C@@H]1c1ccccc1] | | Phenylcyclopropyl |
| 1906 | 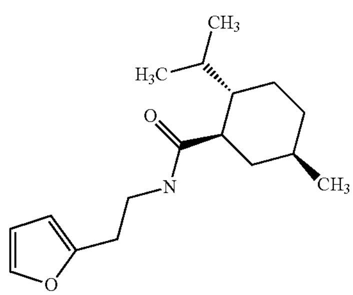 [SMILES: CC(C)[C@@H]1CC[C@@H](C)C[C@H]1C(=O)NCCc1ccco1] | | 2-(2-furyl)ethyl |
| 2920 | 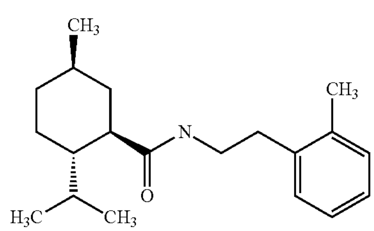 [SMILES: Cc1ccccc1CCNC(=O)[C@@H]1C[C@H](C)CC[C@H]1C(C)C] | | 2-(2-methylphenyl)ethyl |
| 2952 | 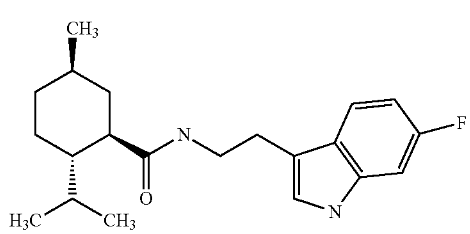 [SMILES: CC(C)[C@@H]1CC[C@@H](C)C[C@H]1C(=O)NCCc1c[nH]c2cc(F)ccc12] | | 2-(6-fluoro-1H-indol-3-yl)-ethyl |

TABLE 1B-continued

Exemplary Trp-p8 Agonists of Formula IV
Exhibiting an $EC_{50}$ Value within the Range of 0.20 to 0.50 μM

| Ref. No.: | Chemical Structure | $R^{14}/R^{15}$ | $R^{15}$ |
|---|---|---|---|
| 3013 | 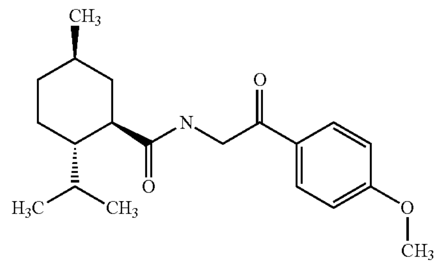 [SMILES: COc1ccc(C(=O)CNC(=O)[C@@H]2C[C@H](C)CC[C@H]2C(C)C)cc1] | | 2-(4-methoxy-phenyl)-2-oxo-ethyl |
| 1603 | 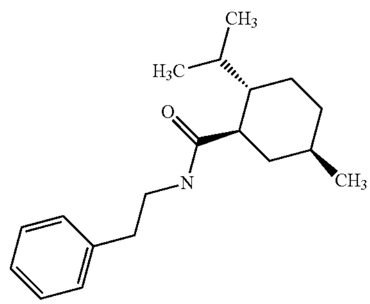 [SMILES: CC(C)[C@@H]1CC[C@@H](C)C[C@H]1C(=O)NCCc1ccccc1] | | 2-phenylethyl |
| 2264 | 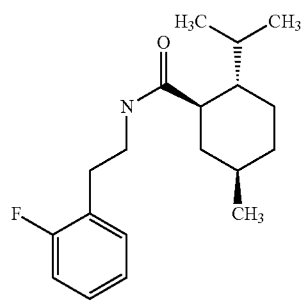 [SMILES: CC(C)[C@@H]1CC[C@@H](C)C[C@H]1C(=O)NCCc1ccccc1F] | | 2-(2-flourophenyl)ethyl |
| 2261 | 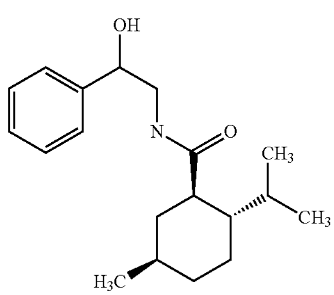 [SMILES: CC(C)[C@@H]1CC[C@@H](C)C[C@H]1C(=O)NCC(O)c1ccccc1] | | 2-hydroxy-2-phenylethyl |
| 2904 | 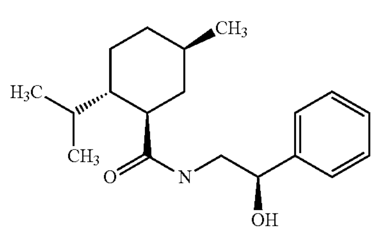 [SMILES: CC(C)[C@@H]1CC[C@@H](C)C[C@H]1C(=O)NC[C@H](O)c1ccccc1] | | 2-hydroxy-2-phenylethyl |

TABLE 1B-continued

Exemplary Trp-p8 Agonists of Formula IV
Exhibiting an $EC_{50}$ Value within the Range of 0.20 to 0.50 μM

| Ref. No.: | Chemical Structure | $R^{14}/R^{15}$ | $R^{15}$ |
|---|---|---|---|
| 2932 | 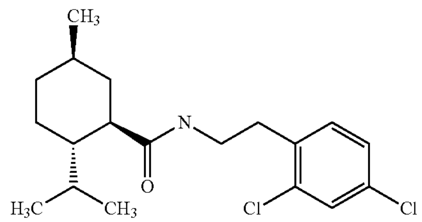 [SMILES: CC(C)[C@@H]1CC[C@@H](C)C[C@H]1C(=O)NCCc1ccc(Cl)cc1Cl] | | 2-(2,4-dichlorophenyl)ethyl |
| 2931 | 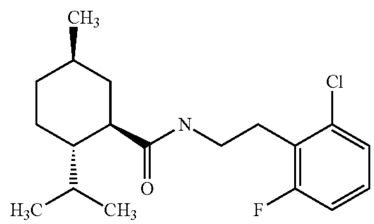 [SMILES: CC(C)[C@@H]1CC[C@@H](C)C[C@H]1C(=O)NCCc1c(F)cccc1Cl] | | 2-(2-chloro-6-flourophenyl)ethyl |
| 2942 | 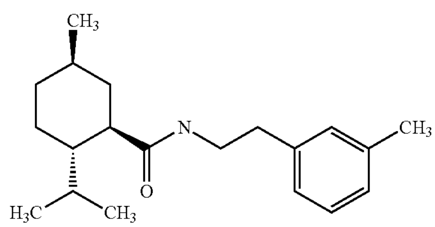 [SMILES: Cc1cccc(CCNC(=O)[C@@H]2C[C@H](C)CC[C@H]2C(C)C)c1] | | 2-(3-methylphenyl)ethyl |
| 2930 | 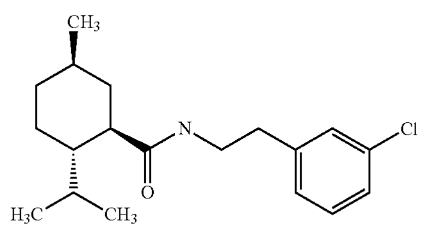 [SMILES: CC(C)[C@@H]1CC[C@@H](C)C[C@H]1C(=O)NCCc1cccc(Cl)c1] | | 2-(3-chlorophenyl)ethyl |
| 1901 | 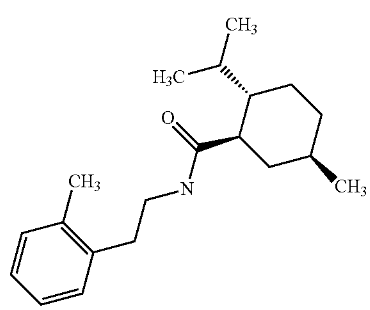 [SMILES: Cc1ccccc1CCNC(=O)[C@@H]1C[C@H](C)CC[C@H]1C(C)C] | | 2-(2-methylphenyl)ethyl |
| 2944 | 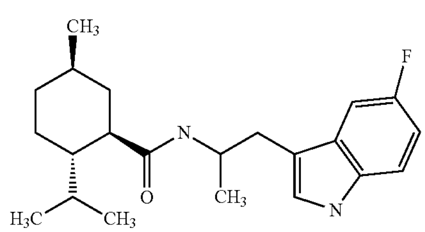 [SMILES: CC(Cc1c[nH]c2ccc(F)cc12)NC(=O)[C@@H]1C[C@H](C)CC[C@H]1C(C)C] | | 1-methyl-2-(5-fluoro-1H-indol-3-yl)-ethyl |

TABLE 1B-continued

Exemplary Trp-p8 Agonists of Formula IV
Exhibiting an $EC_{50}$ Value within the Range of 0.20 to 0.50 μM

| Ref. No.: | Chemical Structure | $R^{14}/R^{15}$ | $R^{15}$ |
|---|---|---|---|
| 3003 | 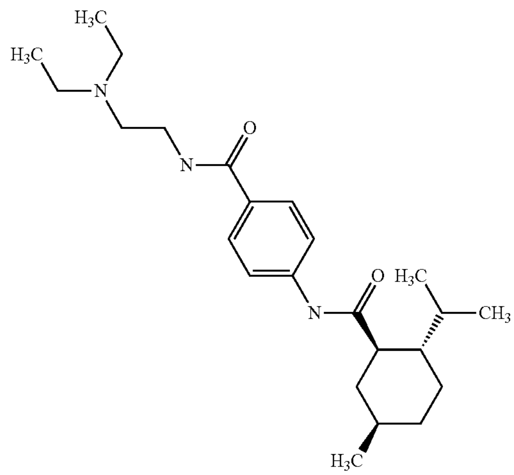 [SMILES: CCN(CC)CCNC(=O)c1ccc(NC(=O)[C@@H]2C[C@H](C)CC[C@H]2C(C)C)cc1] | | N-(2-diethylamino-ethyl)-benzamide-4-yl |
| 2966 | 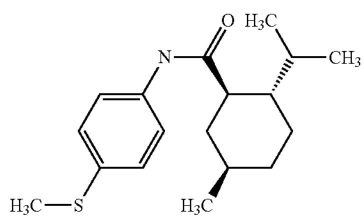 [SMILES: CSc1ccc(NC(=O)[C@@H]2C[C@H](C)CC[C@H]2C(C)C)cc1] | | 4-methylsulfanylphenyl |
| 2973 | 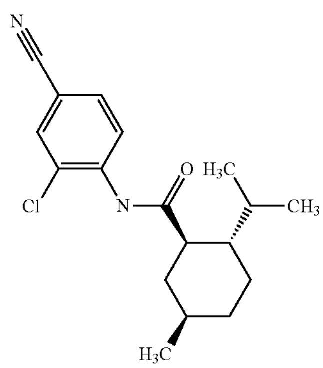 [SMILES: CC(C)[C@@H]1CC[C@@H](C)C[C@H]1C(=O)Nc1ccc(C#N)cc1Cl] | | 2-chloro-4-cyanophenyl |
| 2869 | 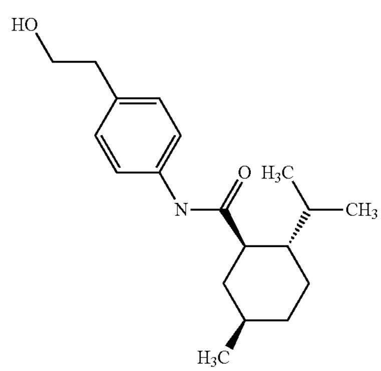 [SMILES: CC(C)[C@@H]1CC[C@@H](C)C[C@H]1C(=O)Nc1ccc(CCO)cc1] | | 4-(2-hydroxyethyl)phenyl |

TABLE 1B-continued

Exemplary Trp-p8 Agonists of Formula IV
Exhibiting an EC$_{50}$ Value within the Range of 0.20 to 0.50 μM

| Ref. No.: | Chemical Structure | R$^{14}$/R$^{15}$ | R$^{15}$ |
|---|---|---|---|
| 2984 | 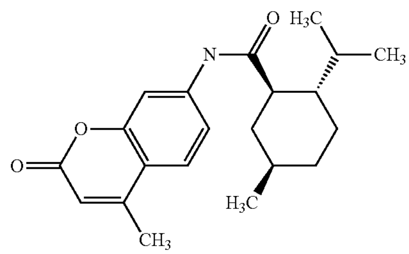 [SMILES: Cc1cc(=O)oc2cc(NC(=O)[C@@H]3C[C@H](C)CC[C@H]3C(C)C)ccc12] | | 4-methyl-2-oxo-2H-chromen-7-yl |
| 2832 | 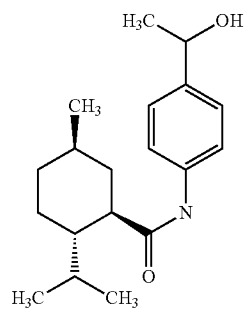 [SMILES: CC(O)c1ccc(NC(=O)[C@@H]2C[C@H](C)CC[C@H]2C(C)C)cc1] | | 4-(1-hydroxyethyl)phenyl |
| 2836 | 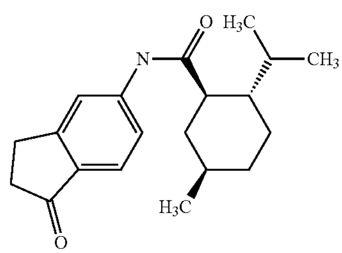 [SMILES: CC(C)[C@@H]1CC[C@@H](C)C[C@H]1C(=O)Nc1ccc2c(c1)CCC2=O] | | 3-oxo-indan-5-yl |
| 2887 | 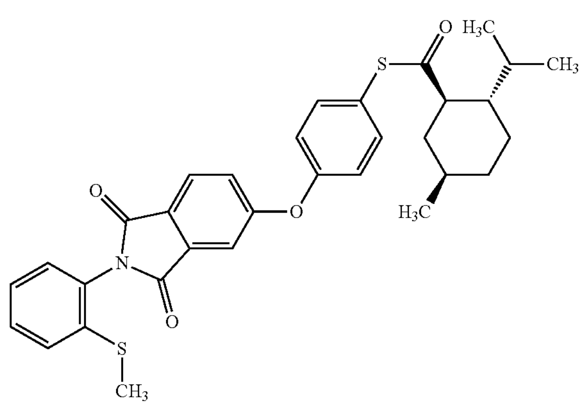 [SMILES: CSc1ccccc1N1C(=O)c2ccc(Oc3ccc(SC(=O)[C@@H]4C[C@H](C)CC[C@H]4C(C)C)cc3)cc2C1=O] | | 4-[2-(2-methoxy-phenyl)-1,3-dioxo-2,3-dihydro-1H-isoindol-5-yloxyl]phenyl |

TABLE 1B-continued
Exemplary Trp-p8 Agonists of Formula IV
Exhibiting an EC$_{50}$ Value within the Range of 0.20 to 0.50 μM
| Ref. No.: | Chemical Structure | R$^{14}$/R$^{15}$ | R$^{15}$ |
|---|---|---|---|
| 2892 | 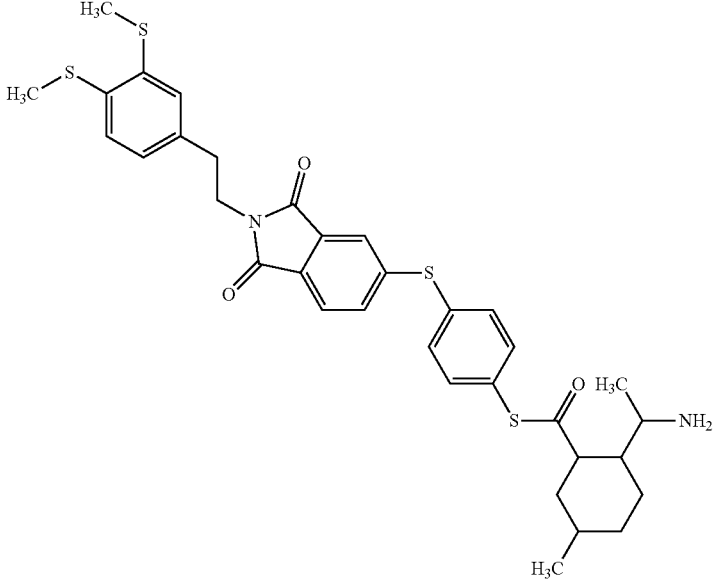 [SMILES: CSc1ccc(CCN2C(=O)c3ccc(Sc4ccc(SC(=O)C5CC(C)CCC5C(C)N)cc4)cc3C2=O)cc1SC] | | 4-{2-[2-(3,4-dimethoxy-phenyl)-ethyl]-1,3-dioxo-2,3-dihydro-1H-isoindol-5-yloxy}-phenyl |
| 2858 | 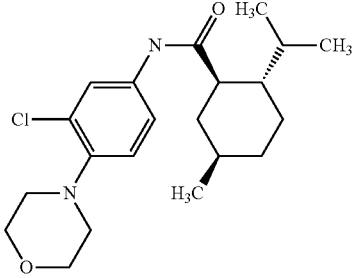 [SMILES: CC(C)[C@@H]1CC[C@@H](C)C[C@H]1C(=O)Nc1ccc(N2CCOCC2)c(Cl)c1] | | 3-chloro-4-morpholin-4-yl-phenyl |
| 2958 | 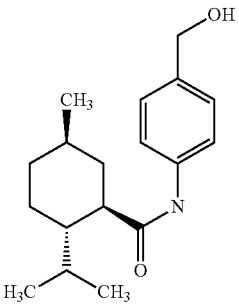 [SMILES: CC(C)[C@@H]1CC[C@@H](C)C[C@H]1C(=O)Nc1ccc(CO)cc1] | | 4-hydroxymethylphenyl |
| 2864 | 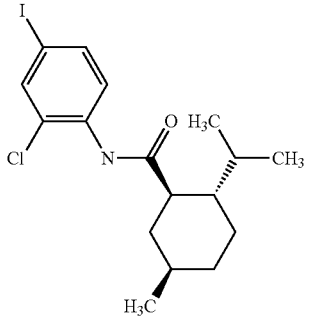 [SMILES: CC(C)[C@@H]1CC[C@@H](C)C[C@H]1C(=O)Nc1ccc(I)cc1Cl] | | 2-chloro-4-iodophenyl |

TABLE 1B-continued

Exemplary Trp-p8 Agonists of Formula IV
Exhibiting an $EC_{50}$ Value within the Range of 0.20 to 0.50 µM

| Ref. No.: | Chemical Structure | $R^{14}/R^{15}$ | $R^{15}$ |
|---|---|---|---|
| 2831 | 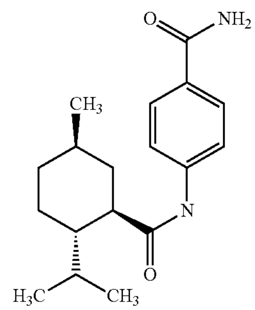 [SMILES: CC(C)[C@@H]1CC[C@@H](C)C[C@H]1C(=O)Nc1ccc(C(N)=O)cc1] | | 4-carboxamidophenyl |
| 2983 | 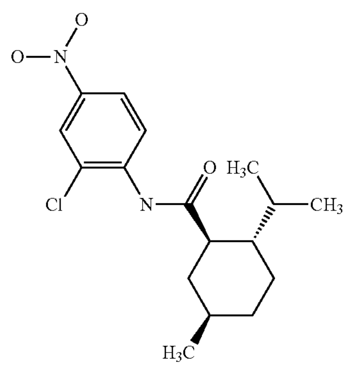 [SMILES: CC(C)[C@@H]1CC[C@@H](C)C[C@H]1C(=O)Nc1ccc(N(O)O)cc1Cl] | | 2-chloro-4-nitrophenyl |
| 2961 | 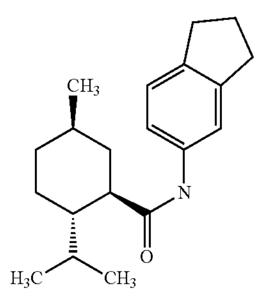 [SMILES: CC(C)[C@@H]1CC[C@@H](C)C[C@H]1C(=O)Nc1ccc2c(c1)CCC2] | | 3,4-cyclopentanephenyl |
| 2828 | 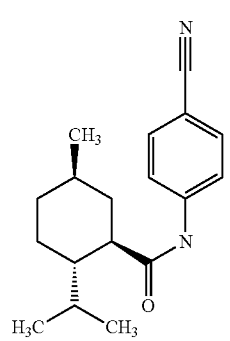 [SMILES: CC(C)[C@@H]1CC[C@@H](C)C[C@H]1C(=O)Nc1ccc(C#N)cc1] | | 4-cyanophenyl |

TABLE 1B-continued

Exemplary Trp-p8 Agonists of Formula IV
Exhibiting an EC$_{50}$ Value within the Range of 0.20 to 0.50 μM

| Ref. No.: | Chemical Structure | $R^{14}/R^{15}$ | $R^{15}$ |
|---|---|---|---|
| 2964 | 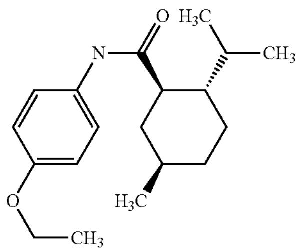 [SMILES: CCOc1ccc(NC(=O)[C@@H]2C[C@H](C)CC[C@H]2C(C)C)cc1] | | 4-ethoxyphenyl |

TABLE 1C

Exemplary Trp-p8 Agonists of Formula IV
Exhibiting an EC$_{50}$ Value within the Range of 0.50 to 1.00 μM

| Ref. No.: | Chemical Structure | $R^{14}/R^{15}$ | $R^{15}$ |
|---|---|---|---|
| 3040 | 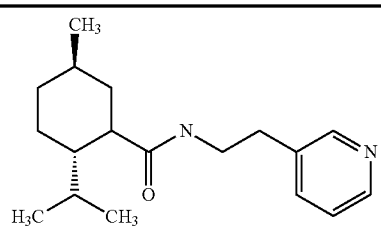 | | 2-(pyridin-3-yl)-ethyl |
| 2903 | 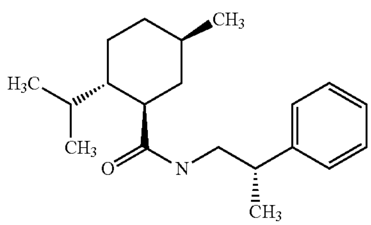 [SMILES: CC(C)[C@@H]1CC[C@@H](C)C[C@H]1C(=O)NC[C@@H](C)c1ccccc1] | | 2-methyl-2-phenylethyl |
| 1903 | 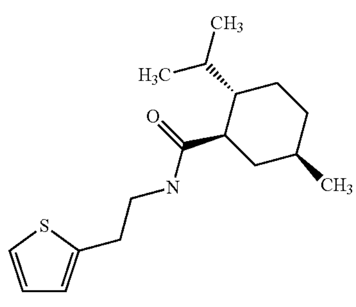 [SMILES: CC(C)[C@@H]1CC[C@@H](C)C[C@H]1C(=O)NCCc1cccs1] | | 2-thiophen-2-yl-ethyl) |
| 2679 | 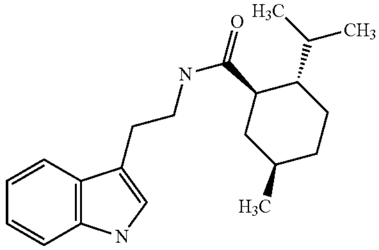 [SMILES: CC(C)[C@@H]1CC[C@@H](C)C[C@H]1C(=O)NCCc1c[nH]c2ccccc12] | | 2-(1H-indol-3-yl)ethyl |

TABLE 1C-continued

Exemplary Trp-p8 Agonists of Formula IV
Exhibiting an $EC_{50}$ Value within the Range of 0.50 to 1.00 μM

| Ref. No.: | Chemical Structure | $R^{14}/R^{15}$ | $R^{15}$ |
|---|---|---|---|
| 2918 | 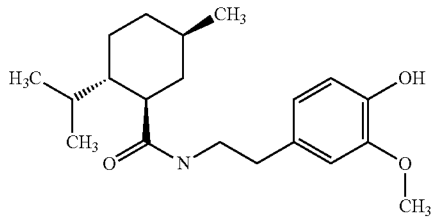 [SMILES: COc1cc(CCNC(=O)[C@@H]2C[C@H](C)CC[C@H]2C(C)C)ccc1O] | | 2-(3-methoxy-4-hydroxyphenyl)ethyl |
| 2263 | 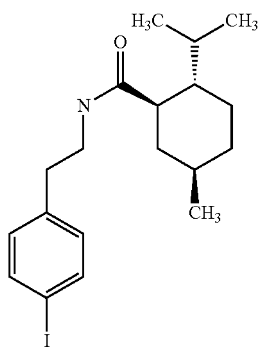 [SMILES: CC(C)[C@@H]1CC[C@@H](C)C[C@H]1C(=O)NCCc1ccc(I)cc1] | | 2-(4-flourophenyl)ethyl |
| 3041 | 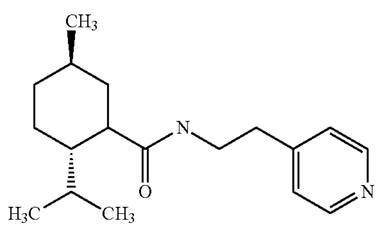 [SMILES: CC(C)[C@@H]1CC[C@@H](C)CC1C(=O)NCCc1ccncc1] | | 2-(pyridin-4-yl)-ethyl |
| 3039 | 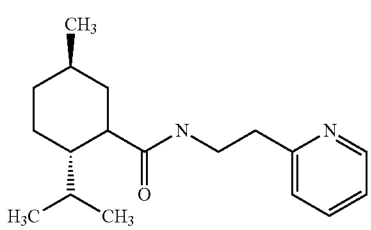 [SMILES: CC(C)[C@@H]1CC[C@@H](C)CC1C(=O)NCCc1ccccn1] | | 2-(pyridin-2-yl)-ethyl |
| 1619 | 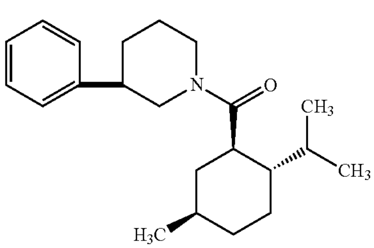 [SMILES: CC(C)[C@@H]1CC[C@@H](C)C[C@H]1C(=O)N1CCC[C@H](c2ccccc2)C1] | | 3-phenyl-piperidin-1-yl |

TABLE 1C-continued

Exemplary Trp-p8 Agonists of Formula IV
Exhibiting an EC$_{50}$ Value within the Range of 0.50 to 1.00 µM

| Ref. No.: | Chemical Structure | R$^{14}$/R$^{15}$ | R$^{15}$ |
|---|---|---|---|
| 2262 | 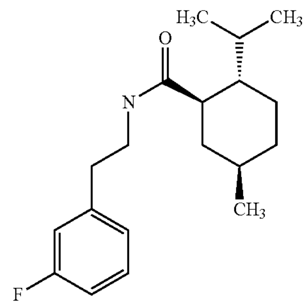 [SMILES: CC(C)[C@@H]1CC[C@@H](C)C[C@H]1C(=O)NCCc1cccc(F)c1] | | 2-(3-flourophenyl)ethyl |
| 2940 | 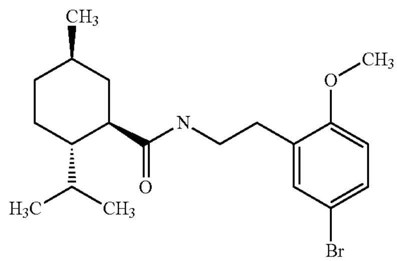 [SMILES: COc1ccc(Br)cc1CCNC(=O)[C@@H]1C[C@H](C)CC[C@H]1C(C)C] | | 2-(2-methoxy-5-bromophenyl)ethyl |
| 2270 | 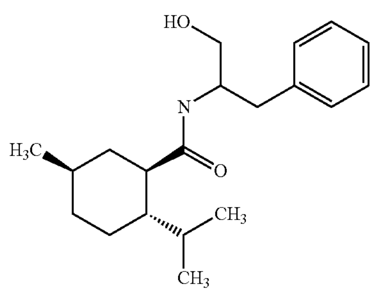 [SMILES: CC(C)[C@@H]1CC[C@@H](C)C[C@H]1C(=O)NC(CO)Cc1ccccc1] | | 1-hydroxymethyl-2-phenyl ethyl |
| 3009 | 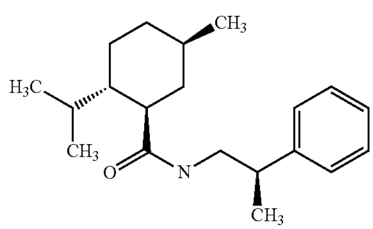 [SMILES: CC(C)[C@@H]1CC[C@@H](C)C[C@H]1C(=O)NC[C@H](C)c1ccccc1] | | 2-methyl-2-phenylethyl |
| 2939 | 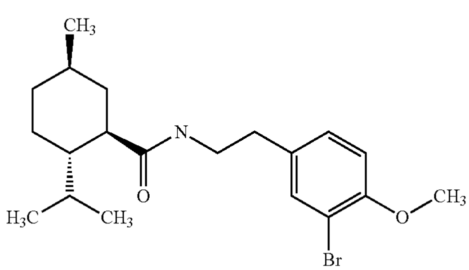 [SMILES: COc1ccc(CCNC(=O)[C@@H]2C[C@H](C)CC[C@H]2C(C)C)cc1Br] | | 2-(3-bromo-4-methoxyphenyl) ethyl |
| 2914 | 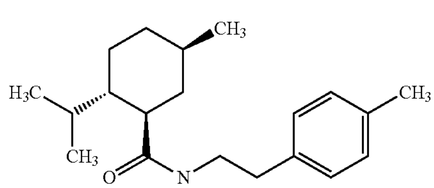 [SMILES: Cc1ccc(CCNC(=O)[C@@H]2C[C@H](C)CC[C@H]2C(C)C)cc1] | | 2-(4-methylphenyl) ethyl |

TABLE 1C-continued

Exemplary Trp-p8 Agonists of Formula IV
Exhibiting an $EC_{50}$ Value within the Range of 0.50 to 1.00 μM

| Ref. No.: | Chemical Structure | $R^{14}/R^{15}$ | $R^{15}$ |
|---|---|---|---|
| 3010 | 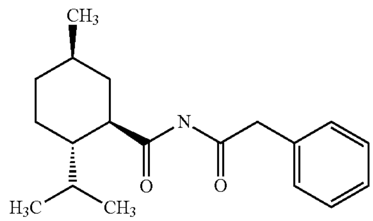 [SMILES: CC(C)[C@@H]1CC[C@@H](C)C[C@H]1C(=O)NC(=O)Cc1ccccc1] | | 1-oxo-2-phenylethyl |
| 2912 | 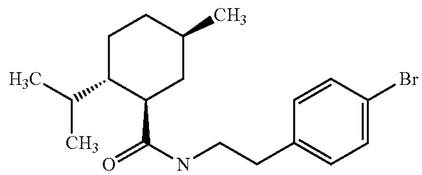 [SMILES: CC(C)[C@@H]1CC[C@@H](C)C[C@H]1C(=O)NCCc1ccc(Br)cc1] | | 2-(4-bromophenyl)-ethyl |
| 2922 | 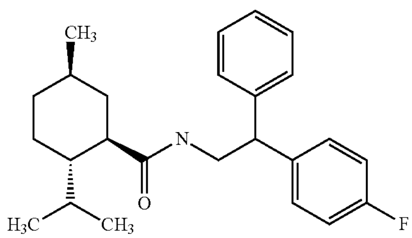 [SMILES: CC(C)[C@@H]1CC[C@@H](C)C[C@H]1C(=O)NCC(c1ccccc1)c1ccc(F)cc1] | | 2-phenyl-2-(4-flourophenyl)-ethyl |
| 2950 | 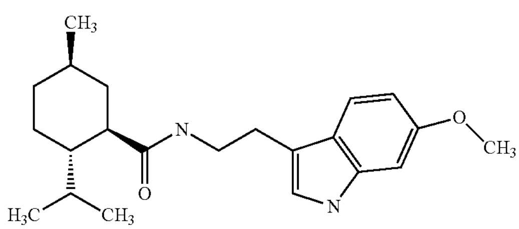 [SMILES: COc1ccc2c(CCNC(=O)[C@@H]3C[C@H](C)CC[C@H]3C(C)C)c[nH]c2c1] | | 2-(6-methoxy-1H-indol-3-yl)-ethyl |
| 2868 | 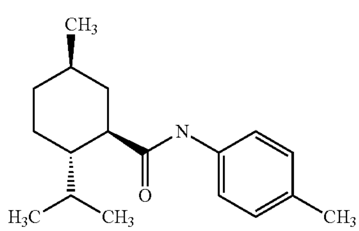 [SMILES: Cc1ccc(NC(=O)[C@@H]2C[C@H](C)CC[C@H]2C(C)C)cc1] | | 4-methylphenyl |
| 2891 | 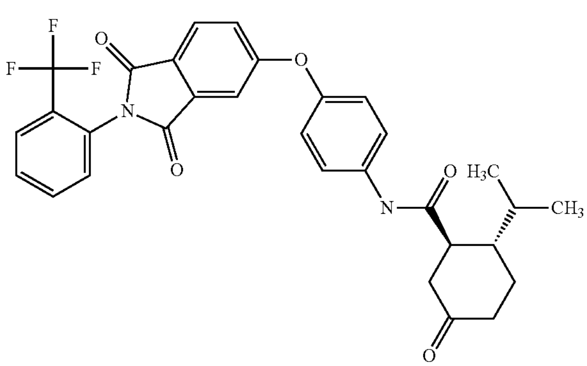 [SMILES: CC(C)[C@@H]1CCC(=O)C[C@H]1C(=O)Nc1ccc(Oc2ccc3c(c2)C(=O)N(c2ccccc2C(F)(F)F)C3=O)cc1] | | 4-[1,3-dioxo-2-(2-trifluoromethyl-phenyl)-2,3-dihydro-1H-isoindol-5-yloxy]-phenyl |

TABLE 1C-continued

Exemplary Trp-p8 Agonists of Formula IV
Exhibiting an $EC_{50}$ Value within the Range of 0.50 to 1.00 μM

| Ref. No.: | Chemical Structure | $R^{14}/R^{15}$ | $R^{15}$ |
|---|---|---|---|
| 2998 | 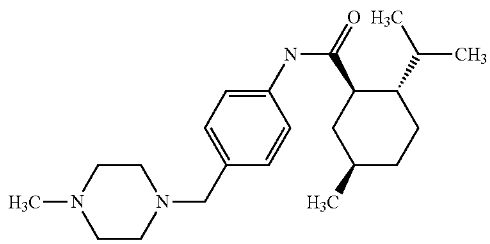 [SMILES: CC(C)[C@@H]1CC[C@@H](C)C[C@H]1C(=O)Nc1ccc(CN2CCN(C)CC2)cc1] | | 4-(4-methyl-piperazin-1-ylmethyl)-phenyl |
| 2960 | 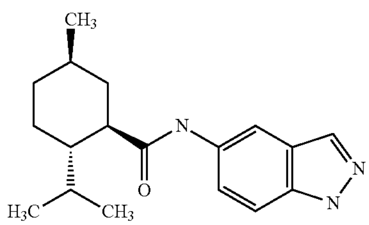 [SMILES: CC(C)[C@@H]1CC[C@@H](C)C[C@H]1C(=O)Nc1ccc2[nH]ncc2c1] | | C-1H-Indazol-5-yl |
| 2970 | 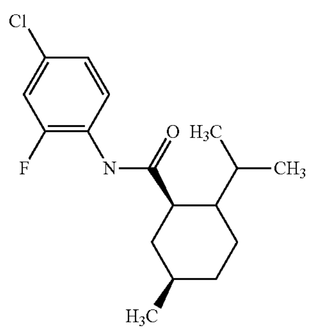 [SMILES: CC(C)C1CC[C@@H](C)C[C@H]1C(=O)Nc1ccc(Cl)cc1F] | | 2-flouro-4-chlorophenyl |
| 2979 | 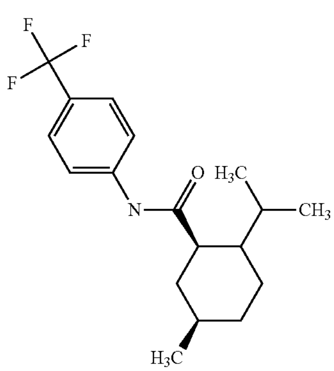 [SMILES: CC(C)C1CC[C@@H](C)C[C@H]1C(=O)Nc1ccc(C(F)(F)F)cc1] | | 4-triflouromethylphenyl |
| 2993 | 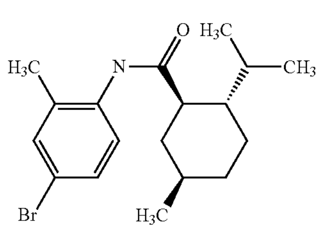 [SMILES: Cc1cc(Br)ccc1NC(=O)[C@@H]1C[C@H](C)CC[C@H]1C(C)C] | | 2-methyl-4-broophenyl |

TABLE 1C-continued

Exemplary Trp-p8 Agonists of Formula IV
Exhibiting an $EC_{50}$ Value within the Range of 0.50 to 1.00 μM

| Ref. No.: | Chemical Structure | $R^{14}/R^{15}$ | $R^{15}$ |
|---|---|---|---|
| 2987 | 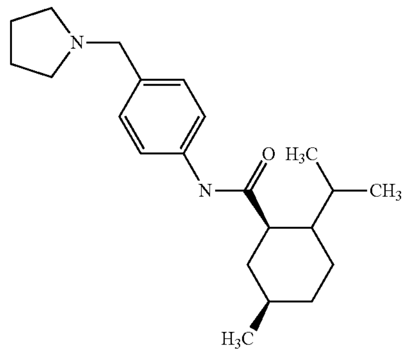 [SMILES: CC(C)C1CC[C@@H](C)C[C@H]1C(=O)Nc1ccc(CN2CCCC2)cc1] | | 4-Pyrrolidin-1-ylmethyl-phenyl |
| 2853 | 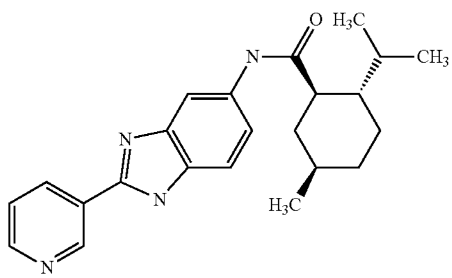 [SMILES: CC(C)[C@@H]1CC[C@@H](C)C[C@H]1C(=O)Nc1ccc2[nH]c(-c3cccnc3)nc2c1] | | 2-phenyl-1H-benzoimidazol-5-yl |
| 2875 | 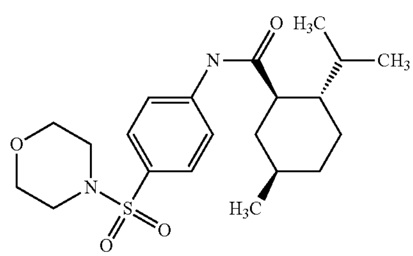 [SMILES: CC(C)[C@@H]1CC[C@@H](C)C[C@H]1C(=O)Nc1ccc(S(=O)(=O)N2CCOCC2)cc1] | | 4-(morpholine-4-sulfonyl)-phenyl |
| 2956 | 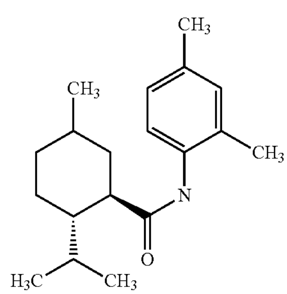 [SMILES: Cc1ccc(NC(=O)[C@@H]2CC(C)CC[C@H]2C(C)C)c(C)c1] | | 2,4-dimethylphenyl |
| 2978 | 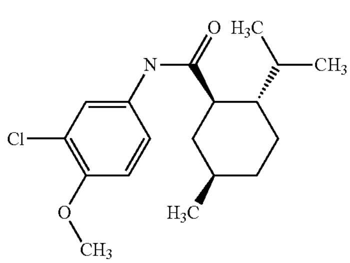 [SMILES: COc1ccc(NC(=O)[C@@H]2C[C@H](C)CC[C@H]2C(C)C)cc1Cl] | | 3-chloro-4-methoxyphenyl |

TABLE 1C-continued

Exemplary Trp-p8 Agonists of Formula IV
Exhibiting an EC$_{50}$ Value within the Range of 0.50 to 1.00 μM

| Ref. No.: | Chemical Structure | R$^{14}$/R$^{15}$ | R$^{15}$ |
|---|---|---|---|
| 2856 | 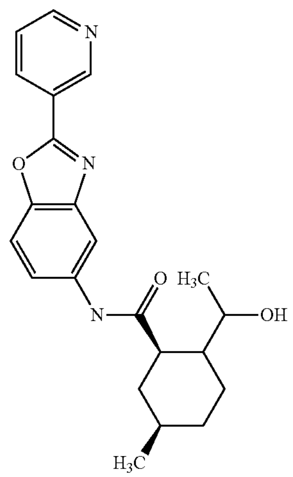 [SMILES: CC(O)C1CC[C@@H](C)C[C@H]1C(=O)Nc1ccc2oc(-c3cccnc3)nc2c1] | | 2-pyridin-3-yl-1H-benzoimidazol-5-yl |

TABLE 1D

Exemplary Trp-p8 Agonists of Formula IV
Exhibiting an EC$_{50}$ Value within the Range of 1.00 to 7.00 μM

| Ref. No.: | Chemical Structure | R$^{14}$/R$^{15}$ | R$^{15}$ |
|---|---|---|---|
| 2943 | 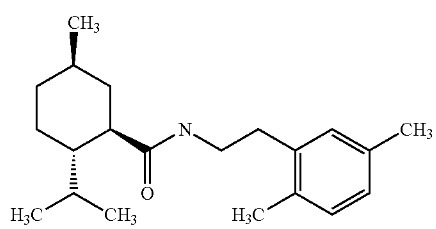 [SMILES: Cc1ccc(C)c(CCNC(=O)[C@@H]2C[C@H](C)CC[C@H]2C(C)C)c1] | | 2-(2,5-dimethylphenyl)-ethyl |
| 2917 | 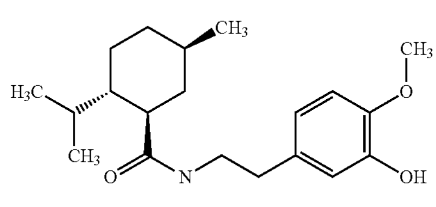 [SMILES: COc1ccc(CCNC(=O)[C@@H]2C[C@H](C)CC[C@H]2C(C)C)cc1O] | | 2-(3-hydroxy-4-methoxyphenyl)-ethyl |
| 2269 | 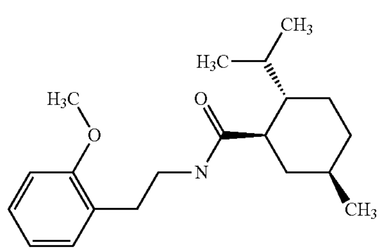 [SMILES: COc1ccccc1CCNC(=O)[C@@H]1C[C@H](C)CC[C@H]1C(C)C] | | 2-(2-methoxyphenyl)-ethyl |

TABLE 1D-continued
Exemplary Trp-p8 Agonists of Formula IV
Exhibiting an $EC_{50}$ Value within the Range of 1.00 to 7.00 μM
| Ref. No.: | Chemical Structure | $R^{14}/R^{15}$ | $R^{15}$ |
|---|---|---|---|
| 3007 | 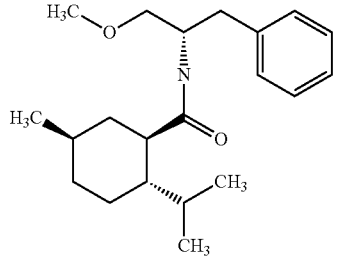 [SMILES: COC[C@H](Cc1ccccc1)NC(=O)[C@@H]1C[C@H](C)CC[C@H]1C(C)C] | | 1-methoxymethyl-2-phenylethyl |
| 2898 | 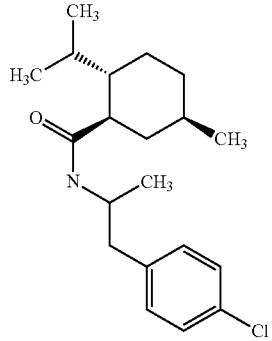 [SMILES: CC(Cc1ccc(Cl)cc1)NC(=O)[C@@H]1C[C@H](C)CC[C@H]1C(C)C] | | 1-methyl-2-(4-chlorophenyl)-ethyl |
| 1627 | 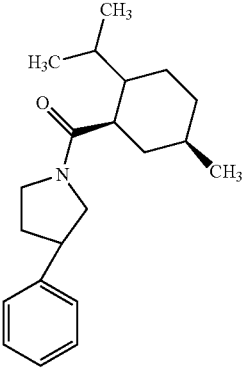 [SMILES: CC(C)C1CC[C@@H](C)C[C@H]1C(=O)N1CCC(c2ccccc2)C1] | 3-phenyl-pyrrolidin-1-yl | |
| 2271 | 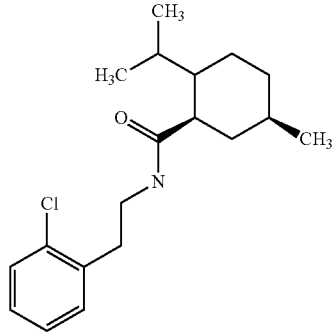 [SMILES: CC(C)C1CC[C@@H](C)C[C@H]1C(=O)NCCc1ccccc1Cl] | | 2-(2-chlorophenyl)ethyl |

TABLE 1D-continued

Exemplary Trp-p8 Agonists of Formula IV
Exhibiting an $EC_{50}$ Value within the Range of 1.00 to 7.00 µM

| Ref. No.: | Chemical Structure | $R^{14}/R^{15}$ | $R^{15}$ |
|---|---|---|---|
| 2933 | 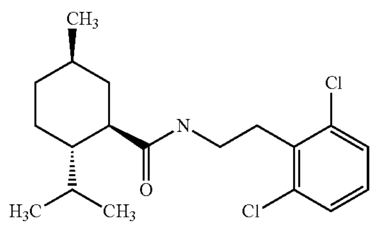 | | 2-(2,6-dimethylphenyl)ethyl |
| 2936 | 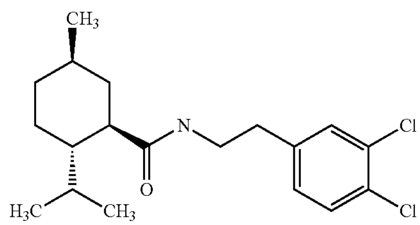 [SMILES: CC(C)[C@@H]1CC[C@@H](C)C[C@H]1C(=O)NCCc1ccc(Cl)c(Cl)c1] | | 2-(3,4-dichlorophenyl)ethyl |
| 2923 | 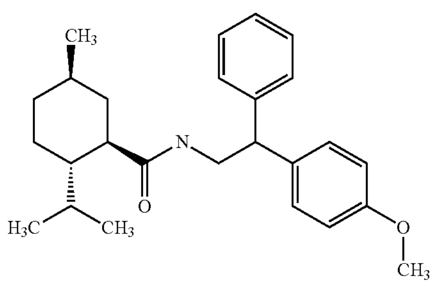 [SMILES: COc1ccc(C(CNC(=O)[C@@H]2C[C@H](C)CC[C@H]2C(C)C)c2ccccc2)cc1] | | 2-phenyl-2-(4-methoxyphenyl)ethyl |
| 2919 | 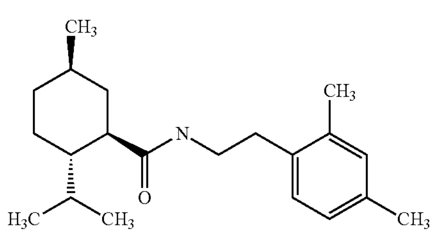 [SMILES: Cc1ccc(CCNC(=O)[C@@H]2C[C@H](C)CC[C@H]2C(C)C)c(C)c1] | | 2-(2,4-dimethylphenyl)ethyl |
| 2266 | 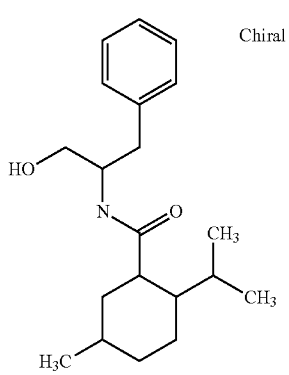 [SMILES: CC1CCC(C(C)C)C(C(=O)NC(CO)Cc2ccccc2)C1] | Chiral | 1-hydroxymethyl-2-phenyl ethyl |

TABLE 1D-continued

Exemplary Trp-p8 Agonists of Formula IV
Exhibiting an $EC_{50}$ Value within the Range of 1.00 to 7.00 μM

| Ref. No.: | Chemical Structure | $R^{14}/R^{15}$ | $R^{15}$ |
|---|---|---|---|
| 2929 | 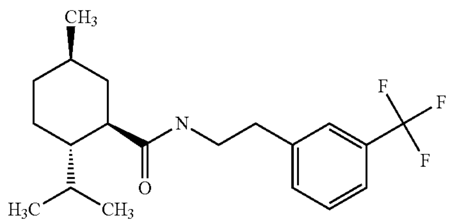 [SMILES: CC(C)[C@@H]1CC[C@@H](C)C[C@H]1C(=O)NCCc1cccc(C(F)(F)F)c1] | | 2-(3-triflouromethylphenyl)ethyl |
| 2935 | 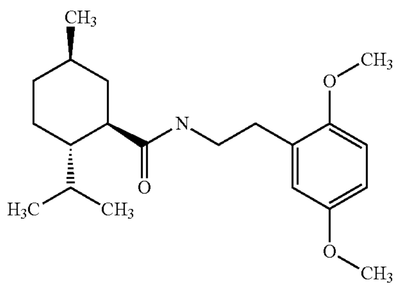 [SMILES: COc1ccc(OC)c(CCNC(=O)[C@@H]2C[C@H](C)CC[C@H]2C(C)C)c1] | | 2-(2,5-dimethoxyphenyl)ethyl |
| 1591 | 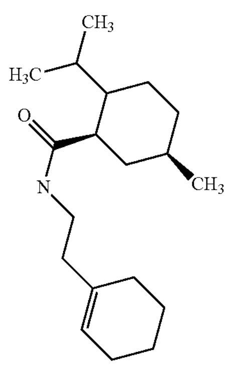 [SMILES: CC(C)C1CC[C@@H](C)C[C@H]1C(=O)NCCC1=CCCCC1] | | 2-cyclohex-1-enyl-ethyl |
| 3035 | 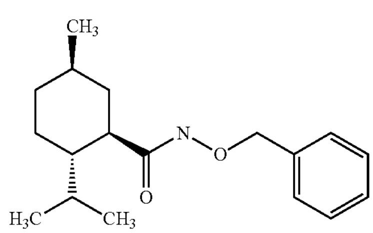 [SMILES: CC(C)[C@@H]1CC[C@@H](C)C[C@H]1C(=O)NOCc1ccccc1] | | benzyloxy |
| 1568 | 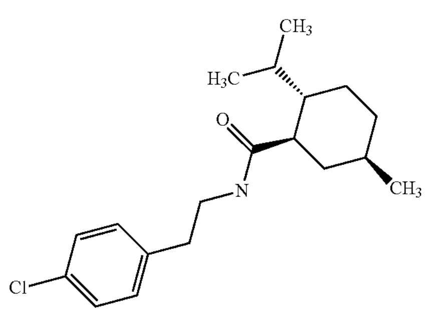 [SMILES: CC(C)[C@@H]1CC[C@@H](C)C[C@H]1C(=O)NCCc1ccc(Cl)cc1] | | 2-(4-chlorophenyl)ethyl |

TABLE 1D-continued

Exemplary Trp-p8 Agonists of Formula IV
Exhibiting an $EC_{50}$ Value within the Range of 1.00 to 7.00 μM

| Ref. No.: | Chemical Structure | $R^{14}/R^{15}$ | $R^{15}$ |
|---|---|---|---|
| 2894 | 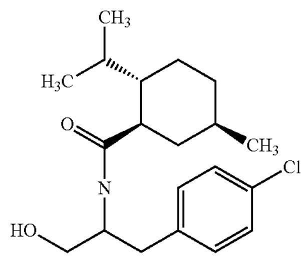 [SMILES: CC(C)[C@@H]1CC[C@@H](C)C[C@H]1C(=O)NC(CO)Cc1ccc(Cl)cc1] | | 1-hydroxymethyl-2-(4-chlorophenyl)ethyl |
| 2265 | 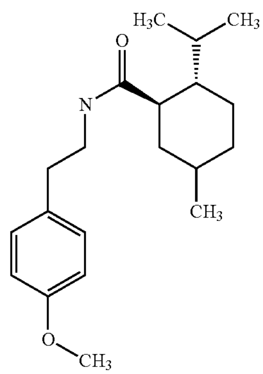 [SMILES: COc1ccc(CCNC(=O)[C@@H]2CC(C)CC[C@H]2C(C)C)cc1] | | 2-(4-methoxyphenyl)ethyl |
| 2924 | 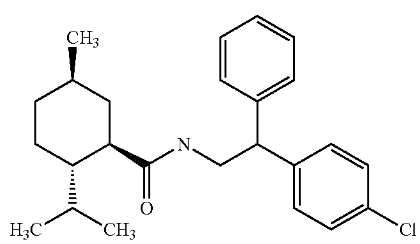 [SMILES: CC(C)[C@@H]1CC[C@@H](C)C[C@H]1C(=O)NCC(c1ccccc1)c1ccc(Cl)cc1] | | 2-phenyl-2-(4-chlorophenyl)ethyl |
| 2677 | 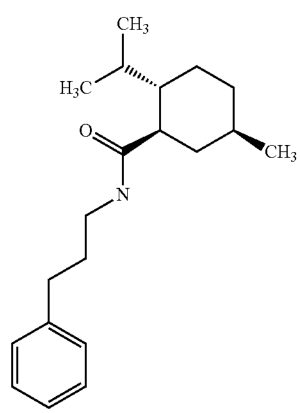 [SMILES: CC(C)[C@@H]1CC[C@@H](C)C[C@H]1C(=O)NCCCc1ccccc1] | | 3-phenylpropyl |

TABLE 1D-continued

Exemplary Trp-p8 Agonists of Formula IV
Exhibiting an EC$_{50}$ Value within the Range of 1.00 to 7.00 µM

| Ref. No.: | Chemical Structure | R$^{14}$/R$^{15}$ | R$^{15}$ |
|---|---|---|---|
| 1910 | 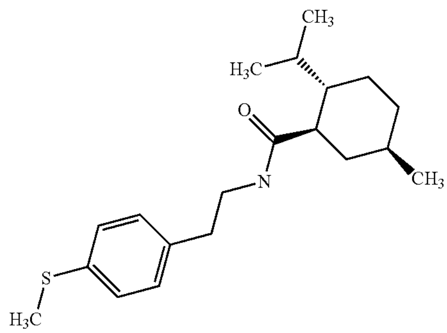 | | 2-(4-methylsulfanylphenyl)ethyl |
| 2273 | 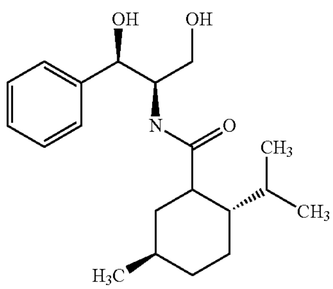 [SMILES: CC(C)[C@@H]1CC[C@@H](C)CC1C(=O)N[C@H](CO)[C@H](O)c1ccccc1] | | 1-hydroxymethyl-2-hydroxy-2-phenylethyl |
| 2937 | 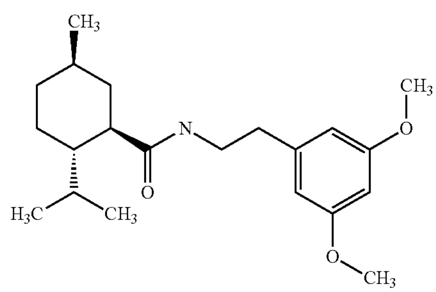 [SMILES: COc1cc(CCNC(=O)[C@@H]2C[C@H](C)CC[C@H]2C(C)C)cc(OC)c1] | | 2-(3,5-dimethoxyphenyl)ethyl |
| 2949 | 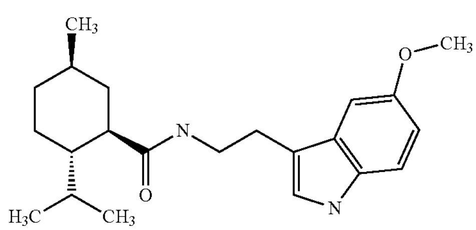 [SMILES: COc1ccc2[nH]cc(CCNC(=O)[C@@H]3C[C@H](C)CC[C@H]3C(C)C)c2c1] | | 2-(5-methoxy-1H-indol-3-yl)-ethyl |
| 2941 | 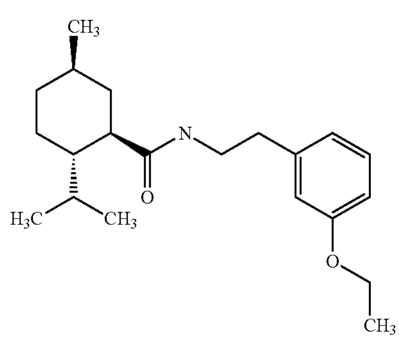 [SMILES: CCOc1cccc(CCNC(=O)[C@@H]2C[C@H](C)CC[C@H]2C(C)C)c1] | | 2-(3-ethoxyphenyl)ethyl |

TABLE 1D-continued

Exemplary Trp-p8 Agonists of Formula IV
Exhibiting an EC$_{50}$ Value within the Range of 1.00 to 7.00 μM

| Ref. No.: | Chemical Structure | R$^{14}$/R$^{15}$ | R$^{15}$ |
|---|---|---|---|
| 2953 | 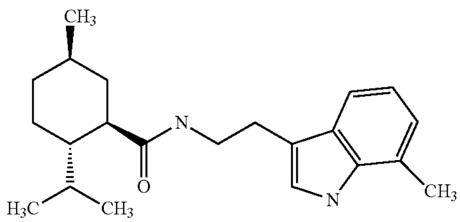 [SMILES: Cc1cccc2c(CCNC(=O)[C@@H]3C[C@H](C)CC[C@H]3C(C)C)c[nH]c12] | | 2-(7-methyl-1H-indol-3-yl)-ethyl |
| 2938 | 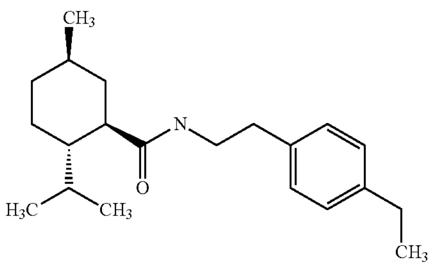 [SMILES: CCc1ccc(CCNC(=O)[C@@H]2C[C@H](C)CC[C@H]2C(C)C)cc1] | | 2-(4-ethylphenyl)ethyl |
| 2934 | 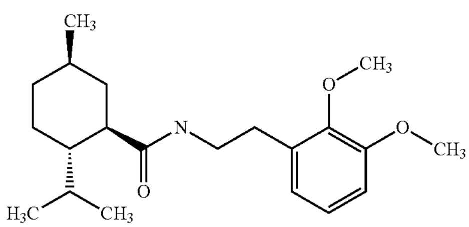 [SMILES: COc1cccc(CCNC(=O)[C@@H]2C[C@H](C)CC[C@H]2C(C)C)c1OC] | | 2-(2,3-dimethoxyphenyl)ethyl |
| 2268 | 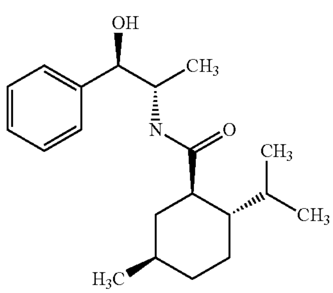 [SMILES: CC(C)[C@@H]1CC[C@@H](C)C[C@H]1C(=O)N[C@@H](C)[C@H](O)c1ccccc1] | | 1-methyl-2-hydroxy-2-phenylethyl |
| 2647 | 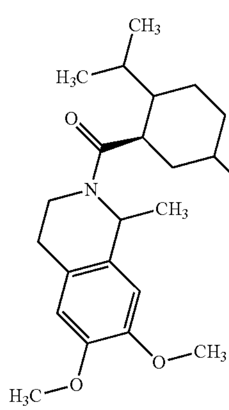 | | 6,7-dimethoxy-1-methyl-3,4-dihydro-1H-isoquinolin-2-yl |

TABLE 1D-continued

Exemplary Trp-p8 Agonists of Formula IV
Exhibiting an EC$_{50}$ Value within the Range of 1.00 to 7.00 μM

| Ref. No.: | Chemical Structure | R$^{14}$/R$^{15}$ | R$^{15}$ |
|---|---|---|---|
| 2915 | 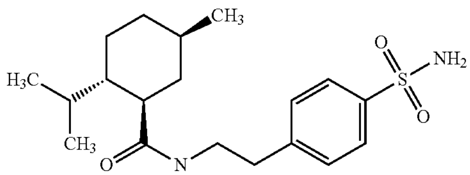 [SMILES: CC(C)[C@@H]1CC[C@@H](C)C[C@H]1C(=O)NCCc1ccc(S(N)(=O)=O)cc1] | | 2-(4-sulfamoyl-phenyl)-ethyl |
| 1912 | 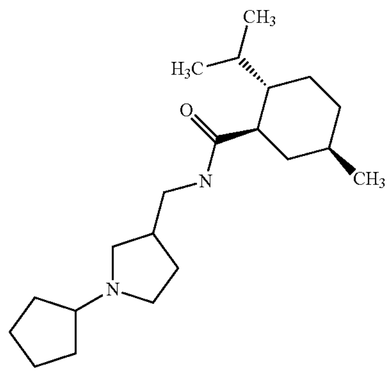 [SMILES: CC(C)[C@@H]1CC[C@@H](C)C[C@H]1C(=O)NCC1CCN(C2CCCC2)C1] | | 2-(1-cyclopentyl-pyrrolidin-3-yl)-ethyl |
| 3032 | 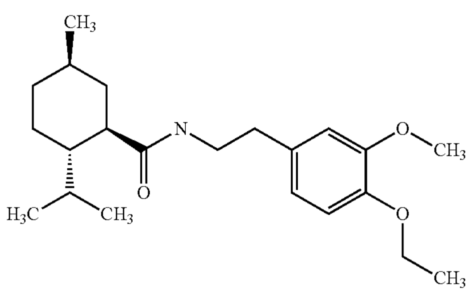 [SMILES: CCOc1ccc(CCNC(=O)[C@@H]2C[C@H](C)CC[C@H]2C(C)C)cc1OC] | | 2-(3-methoxy-4-ethoxyphenyl)ethyl |
| 2947 | 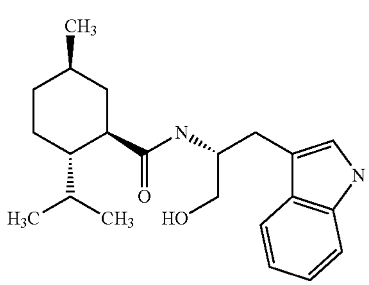 [SMILES: CC(C)[C@@H]1CC[C@@H](C)C[C@H]1C(=O)N[C@@H](CO)Cc1c[nH]c2ccccc12] | | 1-hydroxymethyl-2-(1H-indol-3-yl)ethyl |
| 2945 | 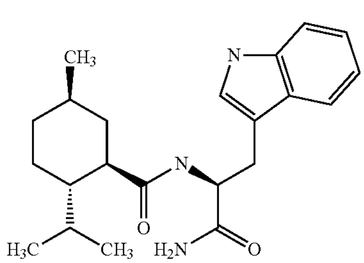 [SMILES: CC(C)[C@@H]1CC[C@@H](C)C[C@H]1C(=O)N[C@@H](Cc1c[nH]c2ccccc12)C(N)=O] | | [1-carbamoyl-2-(1H-indol-3-yl)-ethyl |

TABLE 1D-continued

Exemplary Trp-p8 Agonists of Formula IV
Exhibiting an $EC_{50}$ Value within the Range of 1.00 to 7.00 μM

| Ref. No.: | Chemical Structure | $R^{14}/R^{15}$ | $R^{15}$ |
|---|---|---|---|
| 1599 | 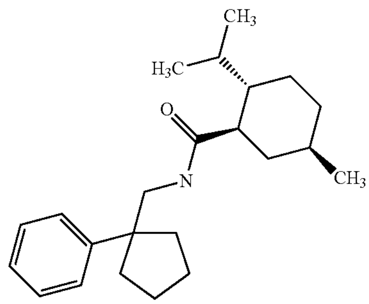 [SMILES: CC(C)[C@@H]1CC[C@@H](C)C[C@H]1C(=O)NCC1(c2ccccc2)CCCC1] | | 1-phenyl-cyclopentylmethyl |
| 3008 | 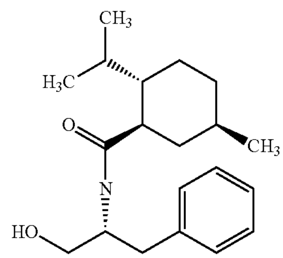 [SMILES: CC(C)[C@@H]1CC[C@@H](C)C[C@H]1C(=O)N[C@@H](CO)Cc1ccccc1] | | 1-hydroxymethyl-2-phenyl ethyl |
| 2909 | 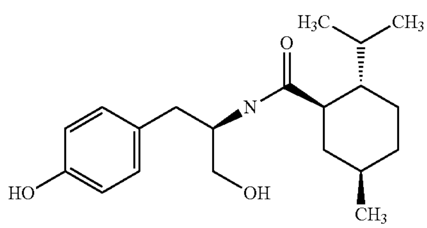 [SMILES: CC(C)[C@@H]1CC[C@@H](C)C[C@H]1C(=O)N[C@@H](CO)Cc1ccc(O)cc1] | | 1-hydroxymethyl-2-(4-hydroxyphenyl)ethyl |
| 2598 | 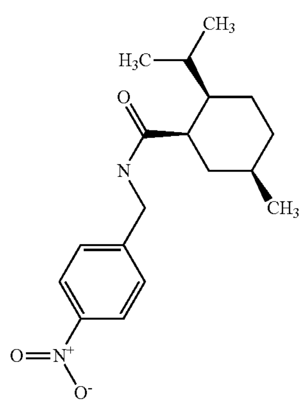 [SMILES: CC(C)[C@H]1CC[C@@H](C)C[C@H]1C(=O)NCc1ccc([N+](=O)[O-])cc1] | | 4-nitrobenzyl |
| 2593 | 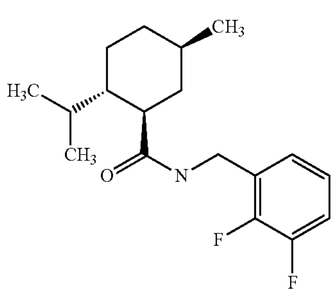 [SMILES: CC(C)[C@@H]1CC[C@@H](C)C[C@H]1C(=O)NCc1cccc(F)c1F] | | 2,3-diflourobenzyl |

TABLE 1D-continued

Exemplary Trp-p8 Agonists of Formula IV
Exhibiting an $EC_{50}$ Value within the Range of 1.00 to 7.00 μM

| Ref. No.: | Chemical Structure | $R^{14}/R^{15}$ | $R^{15}$ |
|---|---|---|---|
| 2899 | 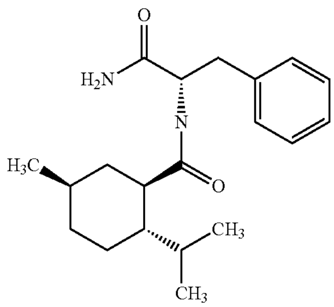 [SMILES: CC(C)[C@@H]1CC[C@@H](C)C[C@H]1C(=O)N[C@@H](Cc1ccccc1)C(N)=O] | | 1-carbamoyl-2-phenylethyl |
| 2279 | 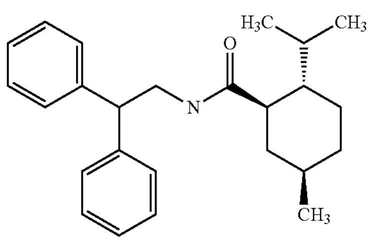 [SMILES: CC(C)[C@@H]1CC[C@@H](C)C[C@H]1C(=O)NCC(c1ccccc1)c1ccccc1] | | 2,2-diphenylethyl |
| 2267 | 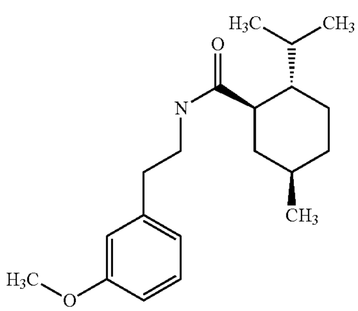 [SMILES: COc1cccc(CCNC(=O)[C@@H]2C[C@H](C)CC[C@H]2C(C)C)c1] | | 2-(3-methoxyphenyl)ethyl |
| 1611 | 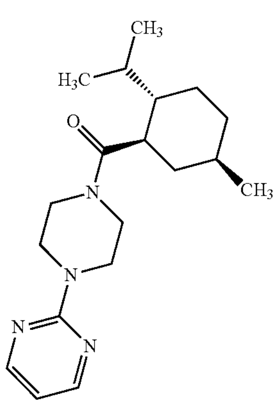 [SMILES: CC(C)[C@@H]1CC[C@@H](C)C[C@H]1C(=O)N1CCN(c2ncccn2)CC1] | | 4-pyrimidin-2-yl-piperazin-1-yl |

TABLE 1D-continued

Exemplary Trp-p8 Agonists of Formula IV
Exhibiting an $EC_{50}$ Value within the Range of 1.00 to 7.00 μM

| Ref. No.: | Chemical Structure | $R^{14}/R^{15}$ | $R^{15}$ |
|---|---|---|---|
| 2277 | 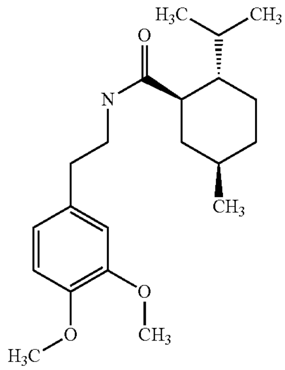 [SMILES: COc1ccc(CCNC(=O)[C@@H]2C[C@H](C)CC[C@H]2C(C)C)cc1OC] | | 2-(3,4-dimethoxyphenyl)ethyl |
| 1566 | 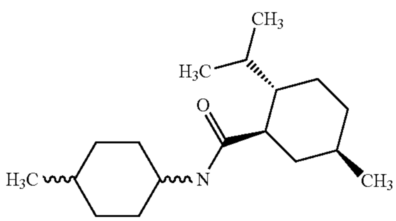 | | 4-methylcyclohexyl |
| 2260 | 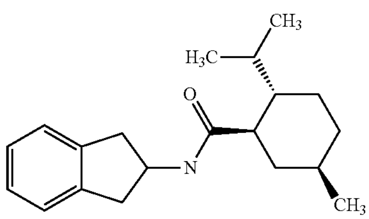 [SMILES: CC(C)[C@@H]1CC[C@@H](C)C[C@H]1C(=O)NC1Cc2ccccc2C1] | | indan-2-yl |
| 2900 | 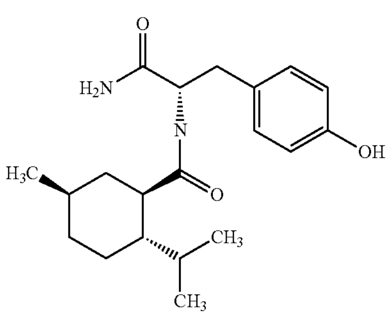 [SMILES: CC(C)[C@@H]1CC[C@@H](C)C[C@H]1C(=O)N[C@@H](Cc1ccc(O)cc1)C(N)=O] | | 1-carbamoyl-2-(4-hydroxyphenyl)ethyl |
| 1637 | 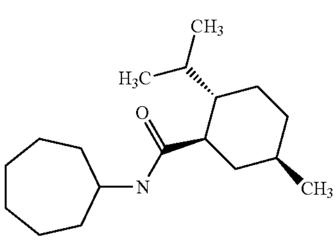 [SMILES: CC(C)[C@@H]1CC[C@@H](C)C[C@H]1C(=O)NC1CCCCCC1] | | cycloheptyl |

TABLE 1D-continued

Exemplary Trp-p8 Agonists of Formula IV
Exhibiting an EC$_{50}$ Value within the Range of 1.00 to 7.00 μM

| Ref. No.: | Chemical Structure | R$^{14}$/R$^{15}$ | R$^{15}$ |
|---|---|---|---|
| 1629 | 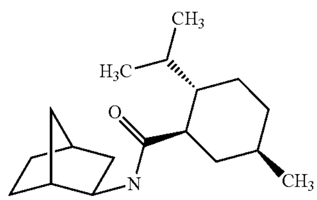 [SMILES: CC(C)[C@@H]1CC[C@@H](C)C[C@H]1C(=O)NC1CC2CCC1C2] | | bicyclo[2.2.1]hept-2-yl |
| 1614 | 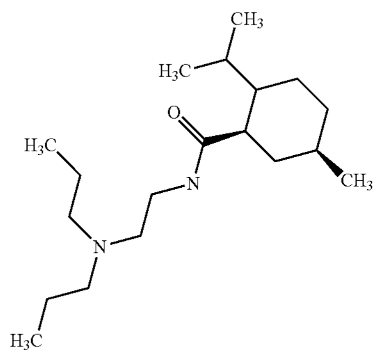 [SMILES: CCCN(CCC)CCNC(=O)[C@@H]1C[C@H](C)CCC1C(C)C] | | 2-(N,N-dipropylamino)ethyl |
| 2272 | 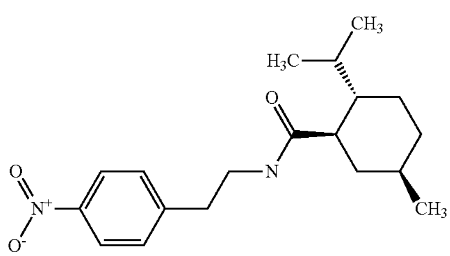 [SMILES: CC(C)[C@@H]1CC[C@@H](C)C[C@H]1C(=O)NCCc1ccc([N+](=O)[O-])cc1] | | 2-(4-nitrophenyl)ethyl |
| 2981 | 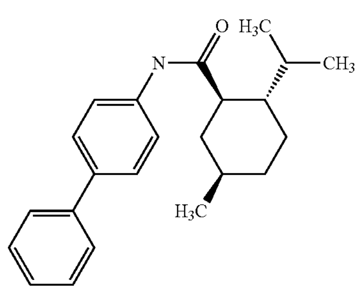 [SMILES: CC(C)[C@@H]1CC[C@@H](C)C[C@H]1C(=O)Nc1ccc(-c2ccccc2)cc1] | | 4-Biphenyl |
| 1617 | 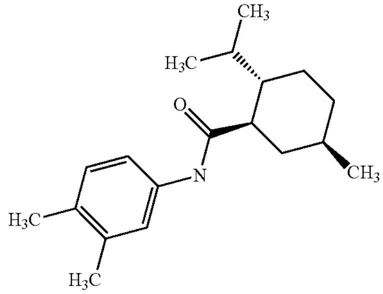 | | 3,4-dimethylphenyl |

TABLE 1D-continued

Exemplary Trp-p8 Agonists of Formula IV
Exhibiting an $EC_{50}$ Value within the Range of 1.00 to 7.00 μM

| Ref. No.: | Chemical Structure | $R^{14}/R^{15}$ | $R^{15}$ |
|---|---|---|---|
| 2862 | 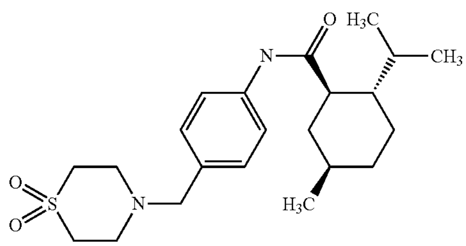 [SMILES: CC(C)[C@@H]1CC[C@@H](C)C[C@H]1C(=O)Nc1ccc(CN2CCS(=O)(=O)CC2)cc1] | | 4-(1,1-dioxo-1l6-thiomorpholin-4-ylmethyl)-phenyl |
| 2844 | 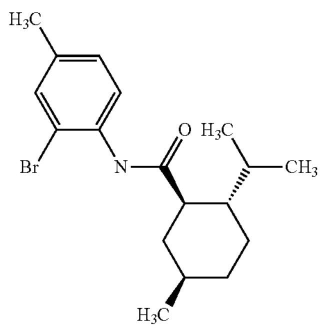 [SMILES: Cc1ccc(NC(=O)[C@@H]2C[C@H](C)CC[C@H]2C(C)C)c(Br)c1] | | 2-bromo-4-methylphenyl |
| 2870 | 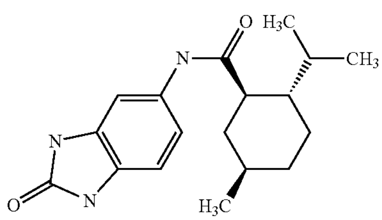 [SMILES: CC(C)[C@@H]1CC[C@@H](C)C[C@H]1C(=O)Nc1ccc2[nH]c(=O)[nH]c2c1] | | 2-oxo-2,3-dihydro-1H-benzoimidazol-5-yl |
| 3030 | 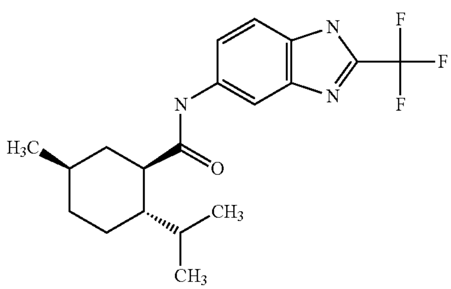 [SMILES: CC(C)[C@@H]1CC[C@@H](C)C[C@H]1C(=O)Nc1ccc2[nH]c(C(F)(F)F)nc2c1] | | 2-trilfouromethyl-1H-benzoimidazol-5-yl |
| 2974 | 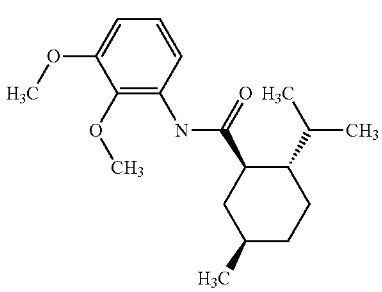 [SMILES: COc1cccc(NC(=O)[C@@H]2C[C@H](C)CC[C@H]2C(C)C)c1OC] | | 2,3-dimethoxyphenyl |

TABLE 1D-continued

Exemplary Trp-p8 Agonists of Formula IV
Exhibiting an EC$_{50}$ Value within the Range of 1.00 to 7.00 μM

| Ref. No.: | Chemical Structure | R$^{14}$/R$^{15}$ | R$^{15}$ |
|---|---|---|---|
| 2849 | 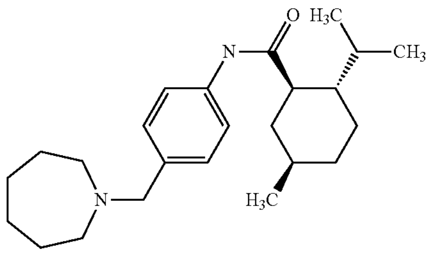 [SMILES: CC(C)[C@@H]1CC[C@@H](C)C[C@H]1C(=O)Nc1ccc(CN2CCCCCC2)cc1] | | 4-Azepan-1-ylmethyl-phenyl |
| 2850 | 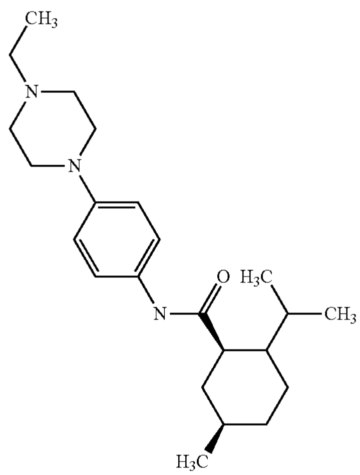 [SMILES: CCN1CCN(c2ccc(NC(=O)[C@@H]3C[C@H](C)CCC3C(C)C)cc2)CC1] | | 4-(4-ethyl-piperazin-1-yl)-phenyl |
| 1631 | 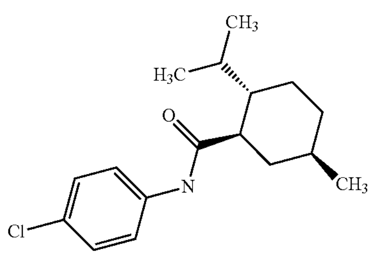 [SMILES: CC(C)[C@@H]1CC[C@@H](C)C[C@H]1C(=O)Nc1ccc(Cl)cc1] | | 4-chlorophenyl |
| 2841 | 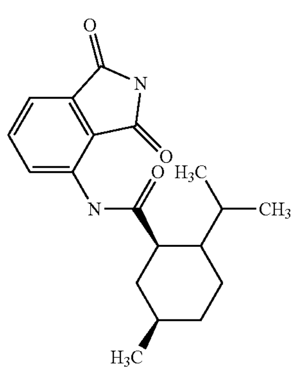 [SMILES: CC(C)C1CC[C@@H](C)C[C@H]1C(=O)Nc1cccc2c1C(=O)NC2=O] | | 1,3-dioxo-2,3-dihydro-1H-isoindol-4-yl |

TABLE 1D-continued

Exemplary Trp-p8 Agonists of Formula IV
Exhibiting an $EC_{50}$ Value within the Range of 1.00 to 7.00 μM

| Ref. No.: | Chemical Structure | $R^{14}/R^{15}$ | $R^{15}$ |
|---|---|---|---|
| 2843 | 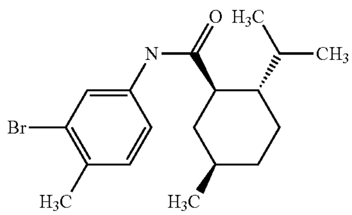 [SMILES: Cc1ccc(NC(=O)[C@@H]2C[C@H](C)CC[C@H]2C(C)C)cc1Br] | | 3-bromo-4-methylphenyl |
| 1607 | 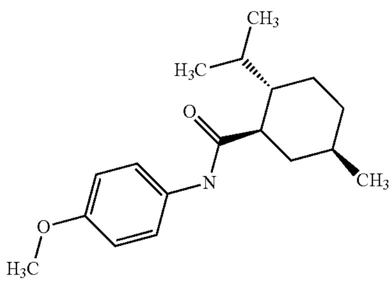 | | 4-methoxyphenyl |
| 2840 | 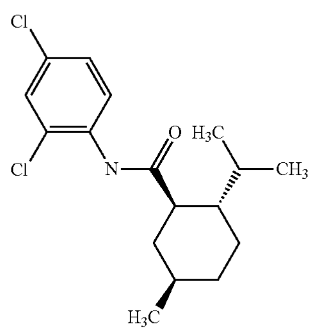 [SMILES: CC(C)[C@@H]1CC[C@@H](C)C[C@H]1C(=O)Nc1ccc(Cl)cc1Cl] | | 2,4-dichlorophenyl |
| 2962 | 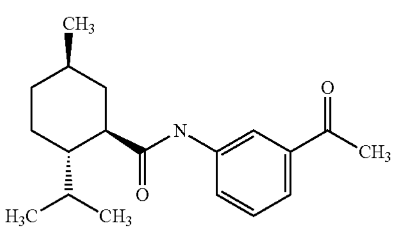 [SMILES: CC(=O)c1cccc(NC(=O)[C@@H]2C[C@H](C)CC[C@H]2C(C)C)c1] | | 3-yl-acetophenone |
| 2872 | 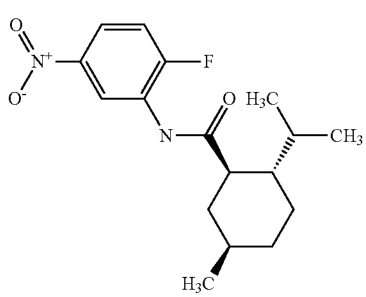 [SMILES: CC(C)[C@@H]1CC[C@@H](C)C[C@H]1C(=O)Nc1cc([N+](=O)[O-])ccc1F] | | 2-flouro-5-nitrophenyl |

TABLE 1D-continued

Exemplary Trp-p8 Agonists of Formula IV
Exhibiting an $EC_{50}$ Value within the Range of 1.00 to 7.00 μM

| Ref. No.: | Chemical Structure | $R^{14}/R^{15}$ | $R^{15}$ |
|---|---|---|---|
| 2985 | 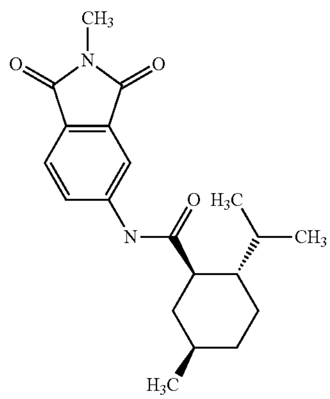 [SMILES: CC(C)[C@@H]1CC[C@@H](C)C[C@H]1C(=O)Nc1ccc2c(c1)C(=O)N(C)C2=O] | | 2-methyl-1,3-dioxo-2,3-dihydro-1H-isoindol-5-yl |
| 1586 | 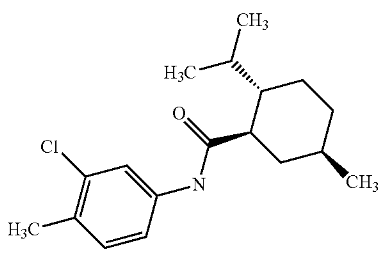 | | 3-chloro-4-methylphenyl |
| 2833 | 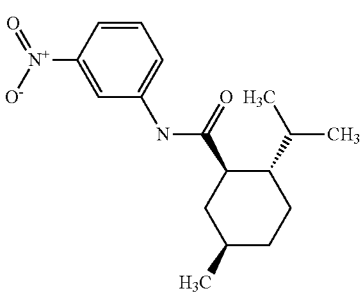 [SMILES: CC(C)[C@@H]1CC[C@@H](C)C[C@H]1C(=O)Nc1cccc([N+](=O)[O-])c1] | | 3-nitrophenyl |
| 2957 | 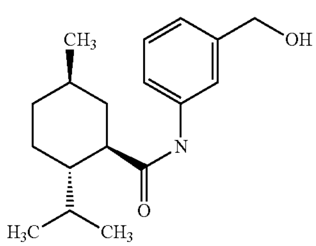 | | 3-hydroxymethylphenyl |
| 1639 | 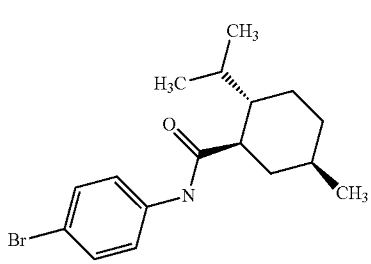 | | 4-bromophenyl |

TABLE 1D-continued

Exemplary Trp-p8 Agonists of Formula IV
Exhibiting an $EC_{50}$ Value within the Range of 1.00 to 7.00 μM

| Ref. No.: | Chemical Structure | $R^{14}/R^{15}$ | $R^{15}$ |
|---|---|---|---|
| 2835 | 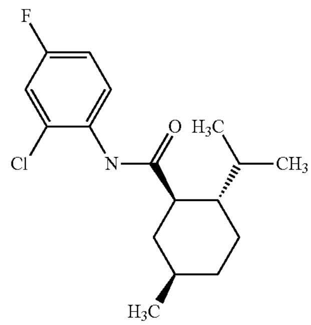 [SMILES: CC(C)[C@@H]1CC[C@@H](C)C[C@H]1C(=O)Nc1ccc(F)cc1Cl] | | 2-chloro-4-flourophenyl |
| 2982 | 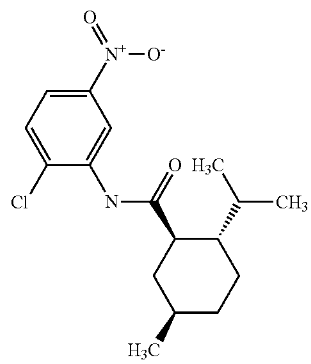 [SMILES: CC(C)[C@@H]1CC[C@@H](C)C[C@H]1C(=O)Nc1cc([N+](=O)[O-])ccc1Cl] | | 2-chloro-5-nitrophenyl |
| 2954 | 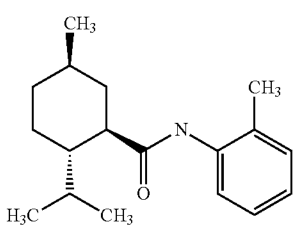 [SMILES: Cc1ccccc1NC(=O)[C@@H]1C[C@H](C)CC[C@H]1C(C)C] | | 2-methylphenyl |
| 2871 | 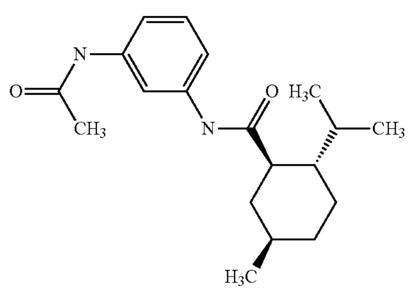 [SMILES: CC(=O)Nc1cccc(NC(=O)[C@@H]2C[C@H](C)CC[C@H]2C(C)C)c1] | | 3-acetamidophenyl |
| 1575 | 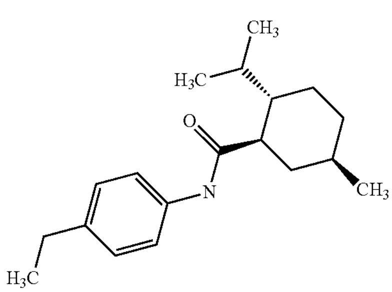 [SMILES: CCc1ccc(NC(=O)[C@@H]2C[C@H](C)CC[C@H]2C(C)C)cc1] | | 4-ethylphenyl |

TABLE 1D-continued

Exemplary Trp-p8 Agonists of Formula IV
Exhibiting an $EC_{50}$ Value within the Range of 1.00 to 7.00 μM

| Ref. No.: | Chemical Structure | $R^{14}/R^{15}$ | $R^{15}$ |
|---|---|---|---|
| 2980 | 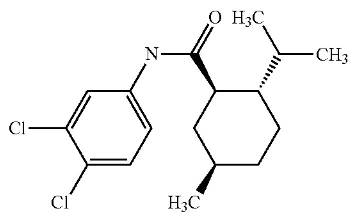 [SMILES: CC(C)[C@@H]1CC[C@@H](C)C[C@H]1C(=O)Nc1ccc(Cl)c(Cl)c1] | | 3,4-dichlorophenyl |
| 1642 | 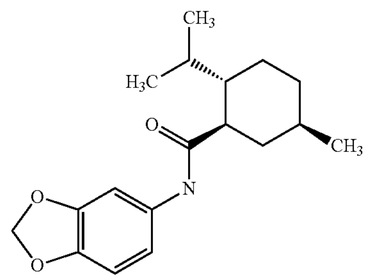 [SMILES: CC(C)[C@@H]1CC[C@@H](C)C[C@H]1C(=O)Nc1ccc2c(c1)OCO2] | | benzo[1,3]dioxol-5-yl |
| 2873 | 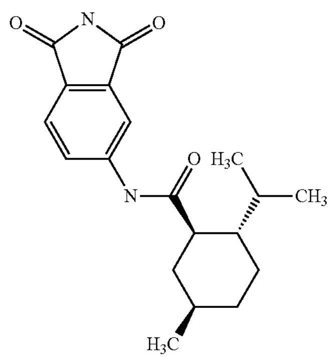 [SMILES: CC(C)[C@@H]1CC[C@@H](C)C[C@H]1C(=O)Nc1ccc2c(c1)C(=O)NC2=O] | | 1,3-dioxo-2,3-dihydro-1H-isoindol-5-yl |
| 2965 | 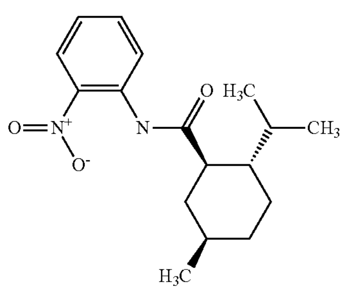 [SMILES: CC(C)[C@@H]1CC[C@@H](C)C[C@H]1C(=O)Nc1ccccc1[N+](=O)[O-]] | | 2-nitrophenyl |
| 2976 | 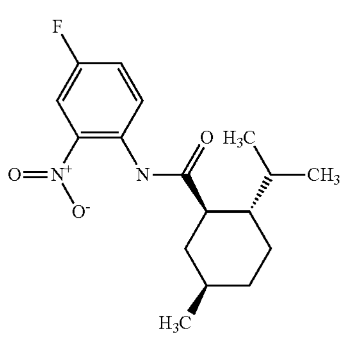 [SMILES: CC(C)[C@@H]1CC[C@@H](C)C[C@H]1C(=O)Nc1ccc(F)cc1[N+](=O)[O-]] | | 2-nitro-4-flourophenyl |

TABLE 1D-continued

Exemplary Trp-p8 Agonists of Formula IV
Exhibiting an $EC_{50}$ Value within the Range of 1.00 to 7.00 μM

| Ref. No.: | Chemical Structure | $R^{14}/R^{15}$ | $R^{15}$ |
|---|---|---|---|
| 1545 | 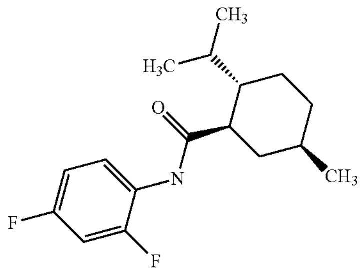 [SMILES: CC(C)[C@@H]1CC[C@@H](C)C[C@H]1C(=O)Nc1ccc(F)cc1F] | | 2,4-diflourophenyl |
| 2990 | 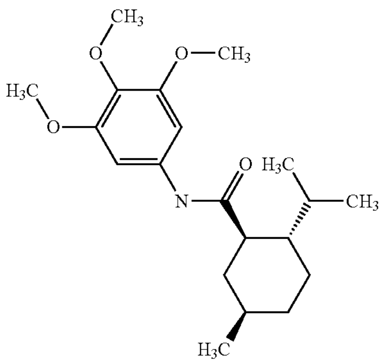 [SMILES: COc1cc(NC(=O)[C@@H]2C[C@H](C)CC[C@H]2C(C)C)cc(OC)c1OC] | | 3,4,5-trimethoxyphenyl |
| 2829 | 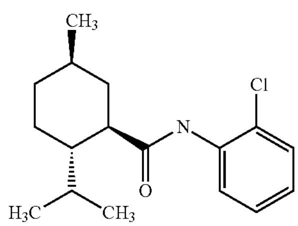 [SMILES: CC(C)[C@@H]1CC[C@@H](C)C[C@H]1C(=O)Nc1ccccc1Cl] | | 2-chlorophenyl |
| 2837 | 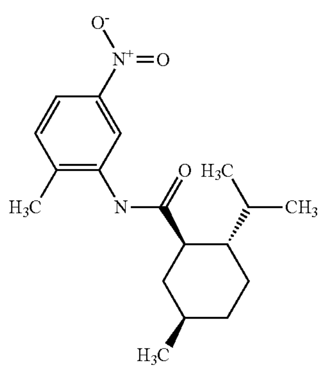 [SMILES: Cc1ccc([N+](=O)[O-])cc1NC(=O)[C@@H]1C[C@H](C)CC[C@H]1C(C)C] | | 2-methyl-5-nitrophenyl |
| 2859 | 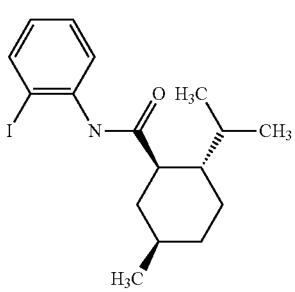 [SMILES: CC(C)[C@@H]1CC[C@@H](C)C[C@H]1C(=O)Nc1ccccc1I] | | 2-iodophenyl |

TABLE 1D-continued

Exemplary Trp-p8 Agonists of Formula IV
Exhibiting an EC$_{50}$ Value within the Range of 1.00 to 7.00 μM

| Ref. No.: | Chemical Structure | R$^{14}$/R$^{15}$ | R$^{15}$ |
|---|---|---|---|
| 2972 | 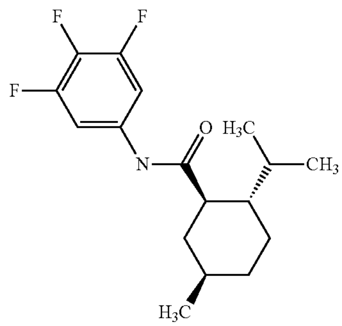 [SMILES: CC(C)[C@@H]1CC[C@@H](C)C[C@H]1C(=O)Nc1cc(F)c(F)c(F)c1] | | 3,4,5-triflourophenyl |
| 3002 | 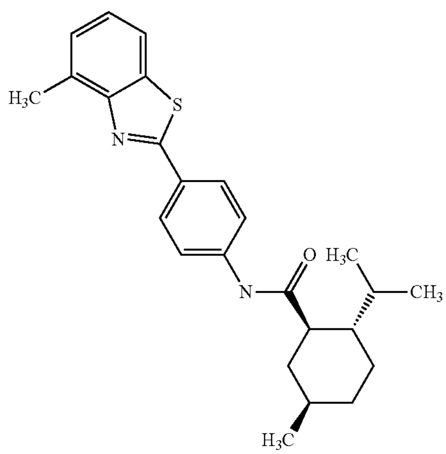 [SMILES: Cc1cccc2sc(-c3ccc(NC(=O)[C@@H]4C[C@H](C)CC[C@H]4C(C)C)cc3)nc12] | | 4-(4-methyl-1H-benzoimidazol-2-yl)-phenyl |
| 2851 | 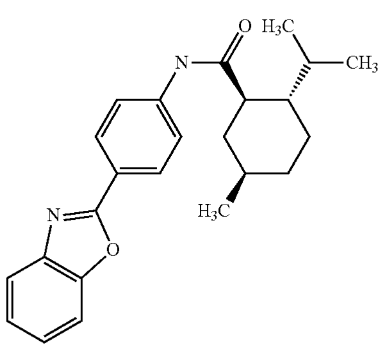 [SMILES: CC(C)[C@@H]1CC[C@@H](C)C[C@H]1C(=O)Nc1ccc(-c2nc3ccccc3o2)cc1] | | 4-benzooxazol-2-yl-phenyl |
| 1616 | 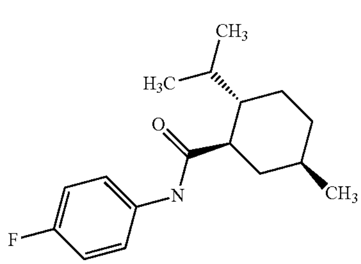 [SMILES: CC(C)[C@@H]1CC[C@@H](C)C[C@H]1C(=O)Nc1ccc(F)cc1] | | 4-flourophenyl |

TABLE 1D-continued

Exemplary Trp-p8 Agonists of Formula IV
Exhibiting an EC$_{50}$ Value within the Range of 1.00 to 7.00 μM

| Ref. No.: | Chemical Structure | R$^{14}$/R$^{15}$ | R$^{15}$ |
|---|---|---|---|
| 2855 | 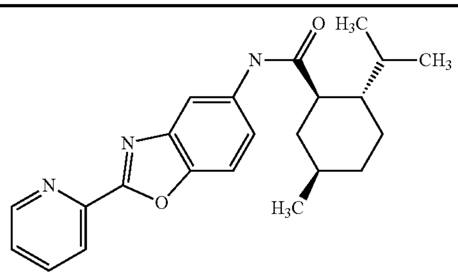 | | 2-pyridin-2-yl-benzooxazol-5-yl |
| 2830 | 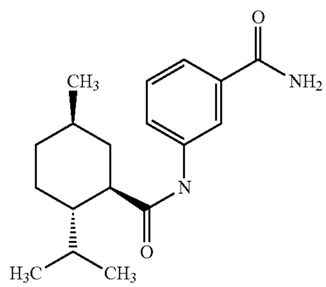 [SMILES: CC(C)[C@@H]1CC[C@@H](C)C[C@H]1C(=O)Nc1cccc(C(N)=O)c1] | | 3-carboxamidophenyl |
| 1577 | 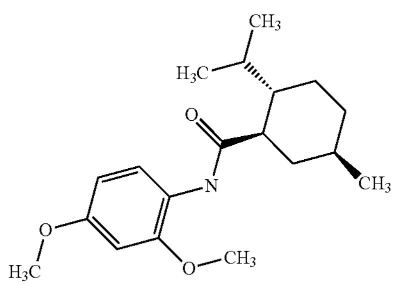 | | 2,4-dimethoxyphenyl |
| 1585 | 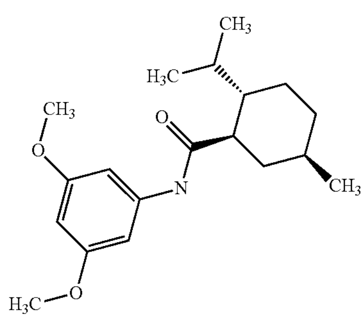 | | 3,5-dimethoxyphenyl |

Example 8

Screen and Characterization of Trp-p8 Agonist Compounds by Measuring Calcium Influx in CHO/Trp-p8 cells at 37° C.

This example discloses a CHO/Trp-p8-based calcium influx assay used to further assess the activity of candidate Trp-p8 agonists of the present invention.

Calcium influx was measured using a Flexstation Microplate Fluorescence Plate Reader (Molecular Devices; Sunnyvale, Calif.). A typical assay for calcium flux was performed as follows. Cells in DMEM/Ham's F-12 based medium, typically at a density of 30,000 cells/well/100 were plated in a 96-well black-walled, clear bottomed tissue culture plate (Greiner Bio-one) and incubated for 16-20 hours at 37° C. Cells in each well were incubated for one hour at 37° C. with a Fura2-AM Fluorescent Dye/Pluronic F-27 mixture (Molecular Probes; Eugene, Oreg.) and dissolved in the medium containing Probenecid. Typical final concentrations were: 5-8 μM of Fura2-AM, 0.01% Pluronic F-27, and 2.5 mM Probenecid (an anion exchange inhibitor that reduces transport of the hydrolyzed dye from inside the cell thereby minimizing loss of dye during the experiment). After one hour, cells were washed in a buffered solution (20 mM HEPES and Hanks Balanced Salt Solution with 1.26 mM CaCl$_2$), pH 7.4 containing Probenecid at a final concentration of 2.5 mM and pre-incubated for at least 30 minutes at the assay temperature of 37° C.

Typically, the above described HEPES/HBSS-based buffer containing either no additional calcium or with calcium to increase the concentration to 2 mM and various concentrations of compounds (at 5-times the final concentrations) were added to each well using the robotic multi-channel pipettor. The compounds were preincubated at 37° C. for at least 30 minutes before performing the assay (at 37° C.). Signals were read with dual excitation wavelengths of 340 and 380 nm and emission wavelength of 510 nm with a cut-off filter at 495 nm. The signal was reported as the ratio of emission when excited at 340 nm to the emission when excited at 380 nm [Relative Fluorescence Units (RFU)]. Ionomycin was routinely used as a positive control.

Figure 2A:
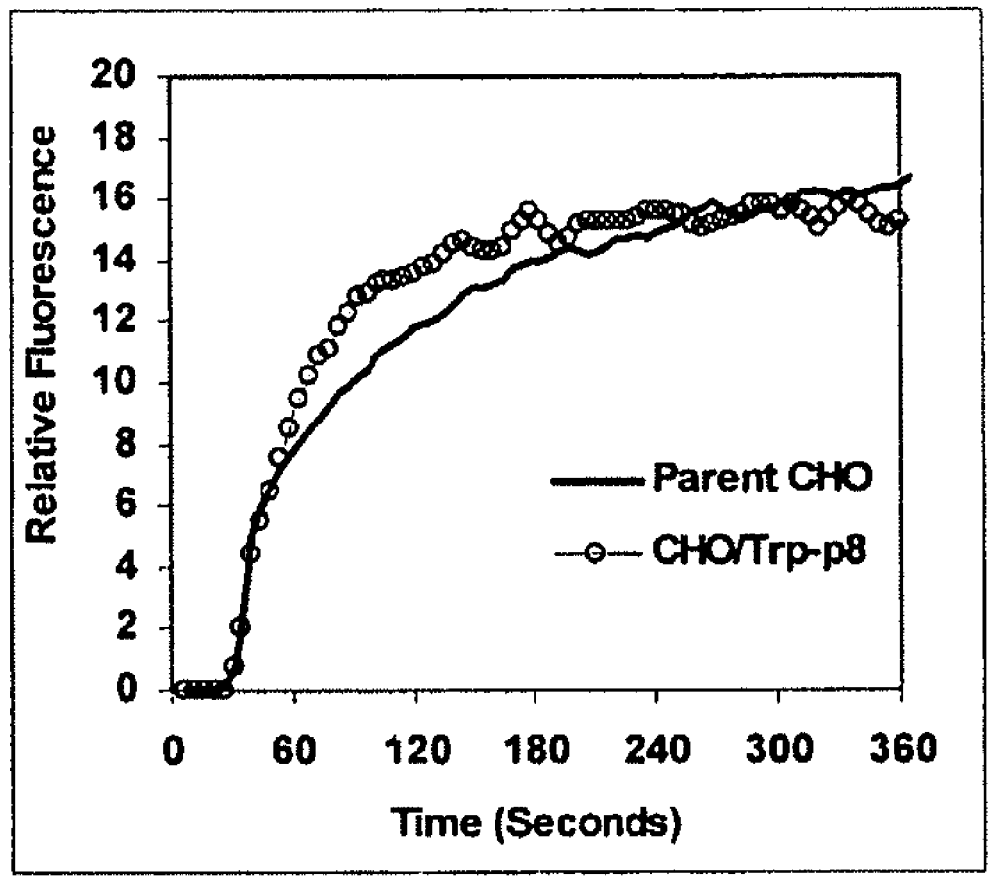
FIGS. 2A-2C are graphs depicting Trp-p8 agonist-induced increases in intracellular calcium as determined by a calcium flux assay performed at 37° C.
Figure 2B:
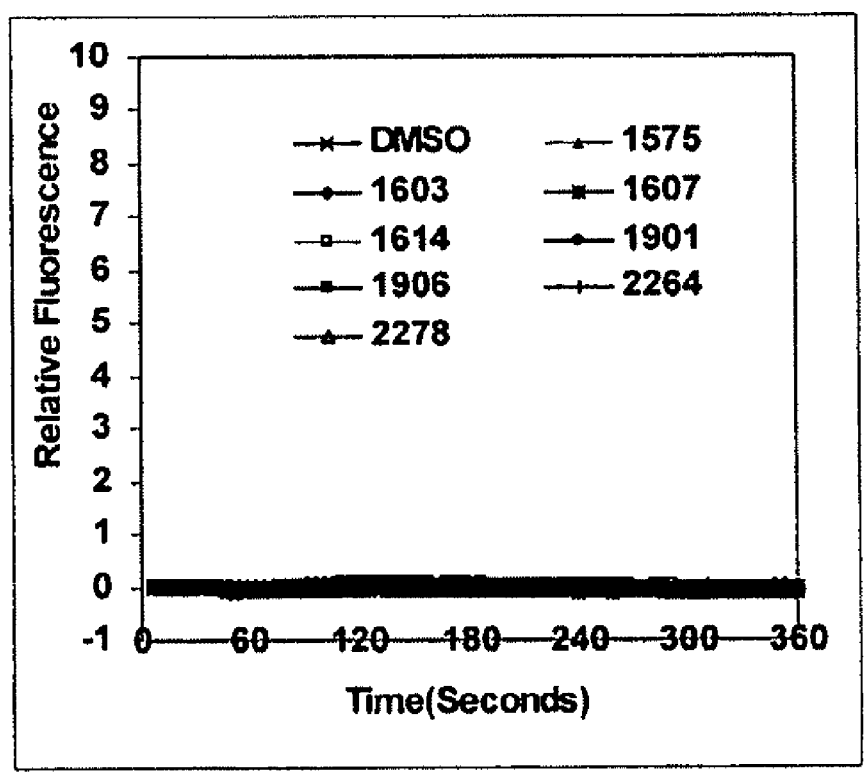
Figure 2C:
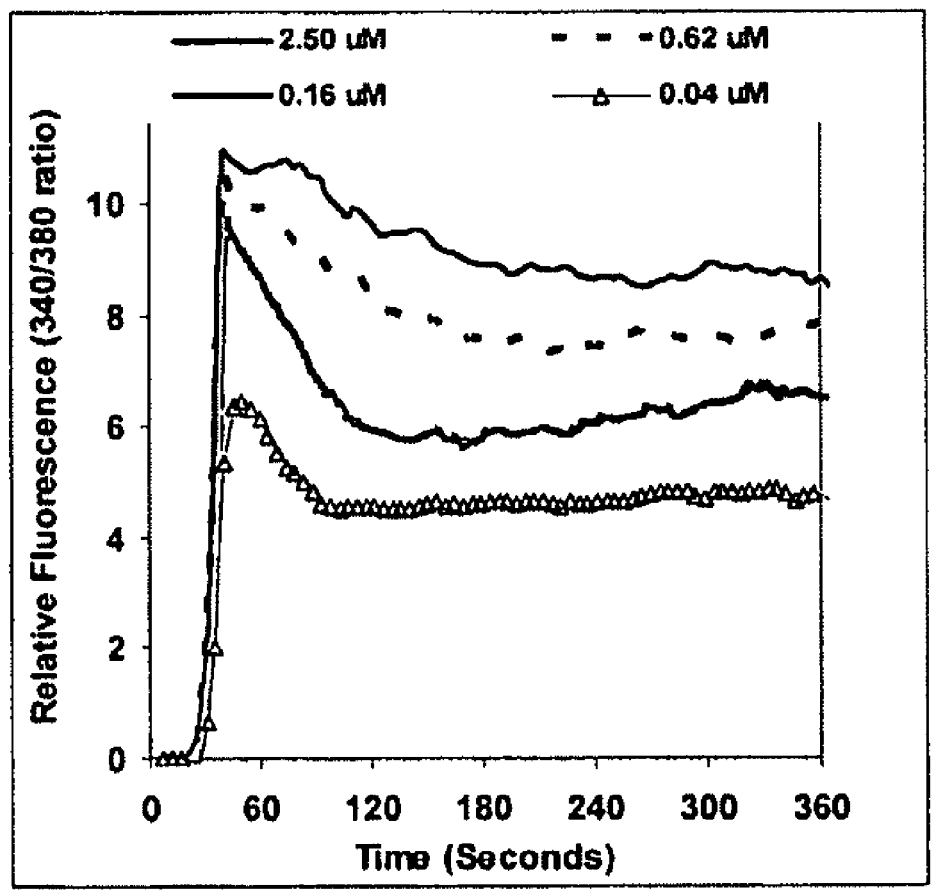

In the case of the agonist assay, the compounds at different concentrations were added to the dye-loaded cells (as described above). The increase in RFU was a measure of potency of the compound as an agonist. Exemplary results are presented in FIG. 2.

Example 9

Increase in Apoptosis following Exposure of CHO/Trp-p8 Cells with Trp-P8 Agonist Compounds at 37° C.

This example discloses the effectiveness of Trp-p8 agonist compounds in inducing apoptosis in Trp-p8 expressing cells.

An Annexin V/Propidium Iodide (PI) flow cytometry assay was used to provide additional insights into the mechanism of cell death induced by Trp-p8 agonist compounds. Annexin V staining detects translocation of Phosphatidylserine to the outer layer of plasma membrane, an event characteristic of apoptosis, while PI staining indicates dead cells with compromised membranes.

Figure 3:
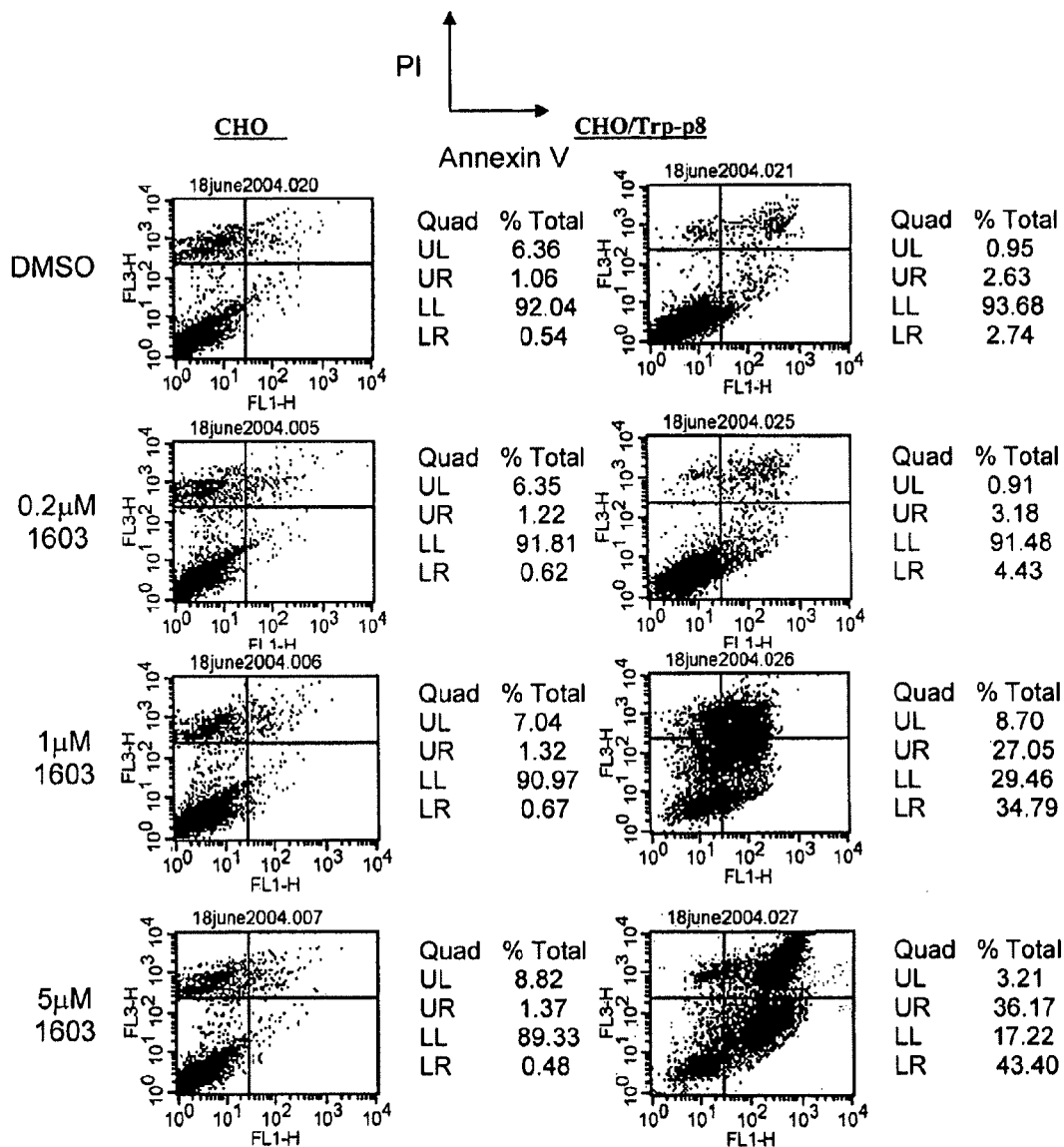
FIG. 3 are plots of flow cytometry data demonstrating that a Trp-p8 agonist is capable of specifically inducing apoptosis in Trp-p8 expressing CHO cells at 37° C.

Cells were treated with compounds in 1% DMSO or with a 1% DMSO (control) for 24-26 hours at 37° C. The cells were briefly trypsinized under controlled conditions and stained with an Annexin V/PI reagent kit following the methodology provided by the supplier (e.g., Southern Biotech; Birmingham, Ala.). Exemplary results are presented in FIG. 3.

Example 10

In Vitro Screen using a Cell Viability Assay for Trp-p8 Antagonist Compounds Based upon Protection of Trp-p8-expressing Cells from Toxic Agonist Compounds This example discloses an assay system for identifying and characterizing candidate Trp-p8 antagonist compounds.

Figure 4:
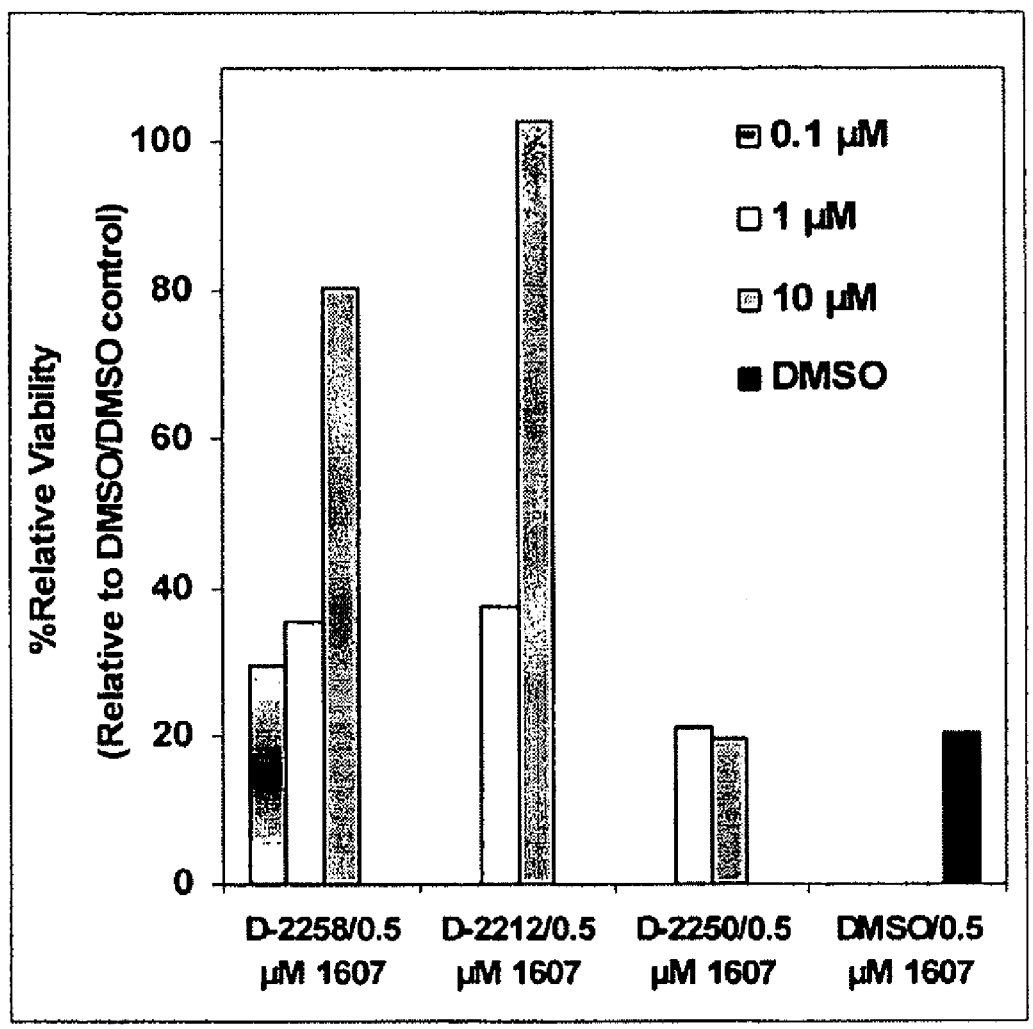
FIG. 4 is a graph depicting exemplary results from a primary screen for Trp-p8 antagonists using the ATP viability assay, described herein, with CHO/Trp-p8 cells at 37° C. CHO/Trp-p8 cells were exposed to compounds, at different concentrations, in 1% DMSO or 1% DMSO in combination with a toxic concentration of the Trp-p8 agonist 1607. The viability of cells was measured after 24-26 hours at 37° C. using the ATP assay. The compounds D-2258 and D-2212 protected the cells from the toxic effect of the Trp-p8 agonist D-1607 and, consequently, are classified as Trp-p8 antagonists. D-2250 had no protective effect and is shown here for the purpose of illustration of the assay.

Trp-p8 antagonists were identified by employing a cell viability assay with CHO/Trp-p8 cells at 37° C. (see Example 7) with the following modification. Within the context of the present invention, compounds that protect CHO/Trp-p8 cells from the toxic effect of a control agonist thereby maintaining the viability of the CHO/Trp-p8 cell exposed to a Trp-p8 agonist is defined as antagonist. As a primary screen for antagonists, CHO/Trp-p8 cells were exposed to 10 µM of test compounds in 1% dimethylsulfoxide (DMSO) or 1% DMSO plus a toxic concentration of a control agonist, D-1607. The relative viability at 10 µM, determined as described in Example 7, was a measure of the potential of the compound as a Trp-p8 antagonist—the higher the viability, the more potent the antagonist. Exemplary results are presented in FIG. 4.

TABLE 2

Exemplary Formula VIII Trp-p8 Antagonists of Formula IV Agonist Compounds

| Ref. No.: | Chemical Structure | $R^{23}/R^{24}$ | $R^{24}$ | Relative Viability (%) at 10 µM |
|---|---|---|---|---|
| 1457 | 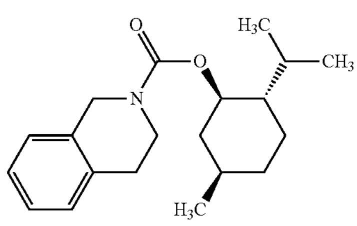 [SMILES: CC(C)[C@@H]1CC[C@@H](C)C[C@H]1OC(=O)N1CCc2ccccc2C1] | Tetrahydro isoquinolinyl | | 112 |
| 1465 | 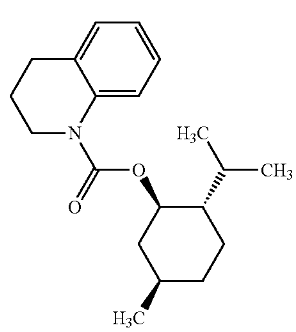 [SMILES: CC(C)[C@@H]1CC[C@@H](C)C[C@H]1OC(=O)N1CCCc2ccccc21] | Tetrahydro quinolinyl | | 90 |

TABLE 2-continued

Exemplary Formula VIII Trp-p8 Antagonists of Formula IV Agonist Compounds

| Ref. No.: | Chemical Structure | $R^{23}/R^{24}$ | $R^{24}$ | Relative Viability (%) at 10 µM |
|---|---|---|---|---|
| 1475 | 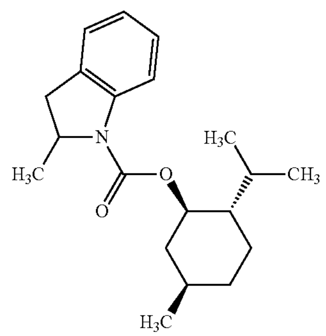 [SMILES: CC(C)[C@@H]1CC[C@@H](C)C[C@H]1OC(=O)N1c2ccccc2CC1C] | | 3-methyl indolinyl | 100 |
| 1504 | 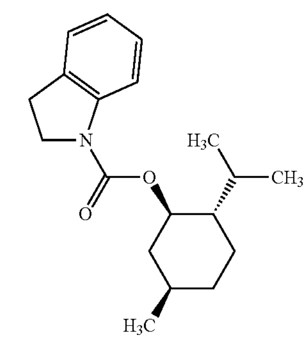 [SMILES: CC(C)[C@@H]1CC[C@@H](C)C[C@H]1OC(=O)N1CCc2ccccc21] | | indolinyl | 90 |
| 1582 | 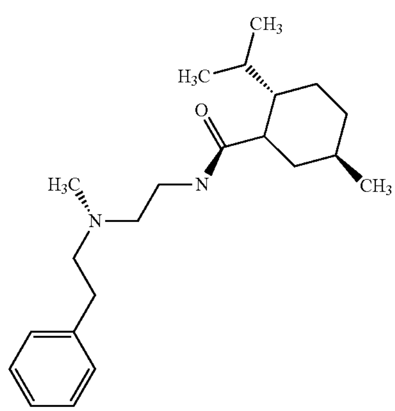 | | 2-(N-methyl, N-Phenylethyl) amino ethyl | 103 |
| 1588 | 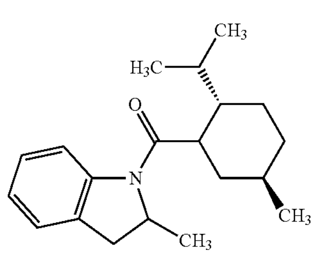 [SMILES: CC(C)[C@@H]1CC[C@@H](C)CC1C(=O)N1c2ccccc2CC1C] | | 3-methyl indolinyl | 88 |

TABLE 2-continued

Exemplary Formula VIII Trp-p8 Antagonists of Formula IV Agonist Compounds

| Ref. No.: | Chemical Structure | $R^{23}/R^{24}$ | $R^{24}$ | Relative Viability (%) at 10 μM |
|---|---|---|---|---|
| 1664 | 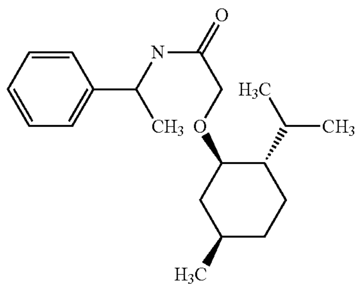 [SMILES: CC(NC(=O)CO[C@@H]1C[C@H](C)CC[C@H]1C(C)C)c1ccccc1] | | 1-phenyl ethyl | 107 |
| 1669 | 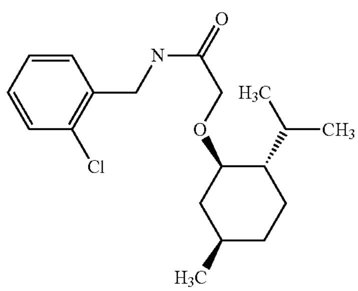 [SMILES: CC(C)[C@@H]1CC[C@@H](C)C[C@H]1OCC(=O)NCc1ccccc1Cl] | | 2-chloro benzyl | 86 |
| 1673 | 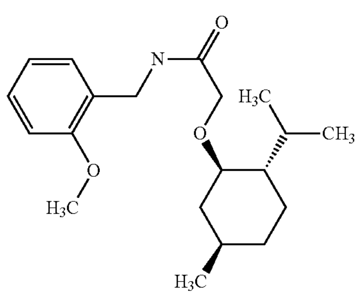 [SMILES: COc1ccccc1CNC(=O)CO[C@@H]1C[C@H](C)CC[C@H]1C(C)C] | | 2-methoxybenzyl | 112 |
| 1688 | 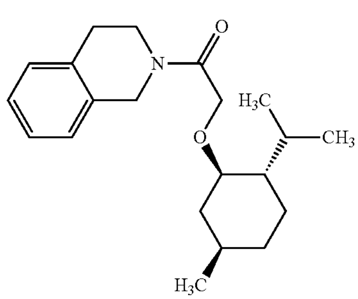 [SMILES: CC(C)[C@@H]1CC[C@@H](C)C[C@H]1OCC(=O)N1CCc2ccccc2C1] | | Tetrahydro isoquinolinyl | 91 |

TABLE 2-continued

Exemplary Formula VIII Trp-p8 Antagonists of Formula IV Agonist Compounds

| Ref. No.: | Chemical Structure | $R^{23}/R^{24}$ | $R^{24}$ | Relative Viability (%) at 10 μM |
|---|---|---|---|---|
| 1691 | 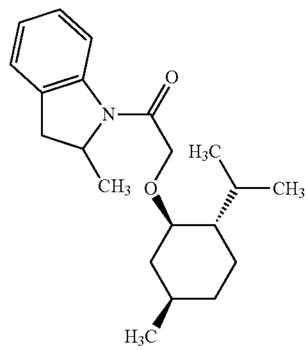 [SMILES: CC(C)[C@@H]1CC[C@@H](C)C[C@H]1OCC(=O)N1c2ccccc2CC1C] | | 3-methyl indolinyl | 92 |
| 1696 | 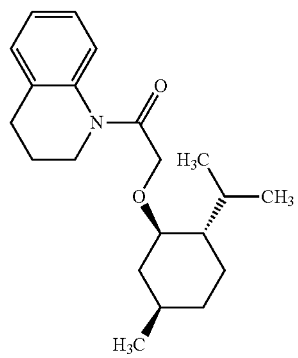 [SMILES: CC(C)[C@@H]1CC[C@@H](C)C[C@H]1OCC(=O)N1CCCc2ccccc21] | | Tetrahydro quinolinyl | 82 |
| 1709 | 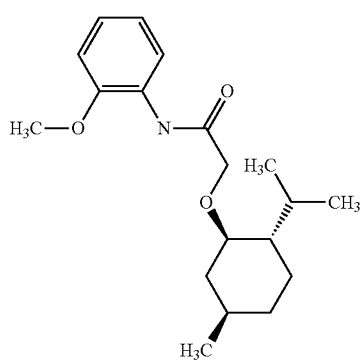 [SMILES: COc1ccccc1NC(=O)CO[C@@H]1C[C@H](C)CC[C@H]1C(C)C] | | 2-methoxyphenyl | 95 |
| 1743 | 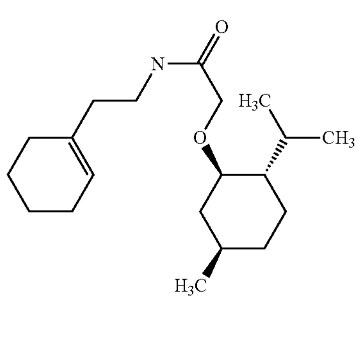 [SMILES: CC(C)[C@@H]1CC[C@@H](C)C[C@H]1OCC(=O)NCCC1=CCCCC1] | | 2-cyclohex-1-enyl ethyl | 97 |

TABLE 2-continued

Exemplary Formula VIII Trp-p8 Antagonists of Formula IV Agonist Compounds

| Ref. No.: | Chemical Structure | $R^{23}/R^{24}$ | $R^{24}$ | Relative Viability (%) at 10 μM |
|---|---|---|---|---|
| 1745 | 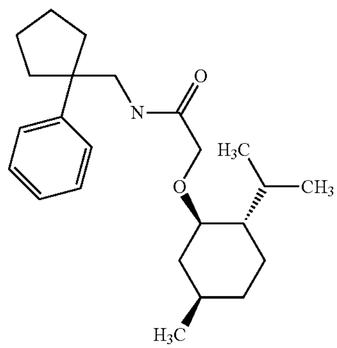 [SMILES: CC(C)[C@@H]1CC[C@@H](C)C[C@H]1OCC(=O)NCC1(c2ccccc2)CCCC1] | | (1-Phenyl-cyclopentyl)-methyl | 88 |
| 1781 | 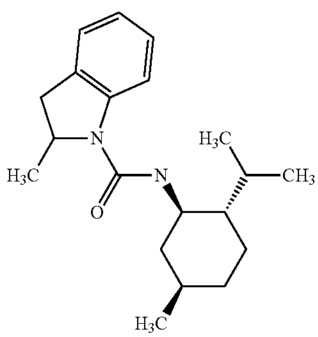 [SMILES: CC(C)[C@@H]1CC[C@@H](C)C[C@H]1NC(=O)N1c2ccccc2CC1C] | | 3-methyl indolinyl | 91 |
| 1815 | 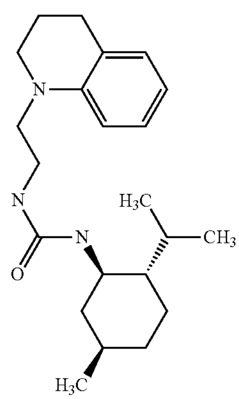 [SMILES: CC(C)[C@@H]1CC[C@@H](C)C[C@H]1NC(=O)NCCN1CCCc2ccccc21] | | 2-(tetrahydroquinolinyl)-ethyl | 87 |
| 1819 | 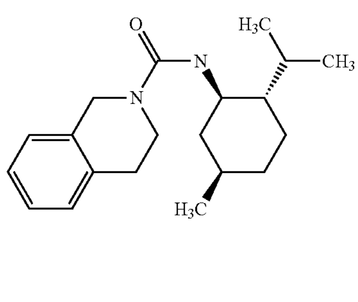 | | Tetrahydro isoquinolinyl | 86 |

TABLE 2-continued

Exemplary Formula VIII Trp-p8 Antagonists of Formula IV Agonist Compounds

| Ref. No.: | Chemical Structure | $R^{23}/R^{24}$ | $R^{24}$ | Relative Viability (%) at 10 μM |
|---|---|---|---|---|
| 1838 | 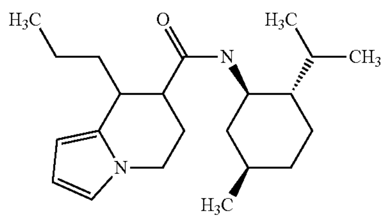 [SMILES: CCCC1c2cccn2CCC1C(=O)N[C@@H]1C[C@H](C)CC[C@H]1C(C)C] | 1-Propyl-1,2,3,4-tetrahydro-pyrrolo[1,2-a]pyrazine | | 88 |
| 1876 | 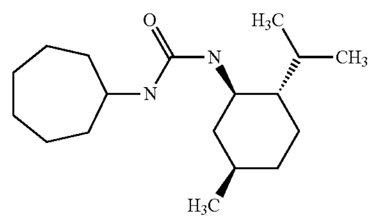 [SMILES: CC(C)[C@@H]1CC[C@@H](C)C[C@H]1NC(=O)NC1CCCCCC1] | | cyclohepttyl | 86 |
| 1882 | 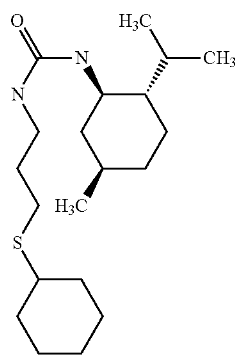 [SMILES: CC(C)[C@@H]1CC[C@@H](C)C[C@H]1NC(=O)NCCCSC1CCCCC1] | | 3-Cyclohexylsulfanylpropyl | 85 |
| 1883 | 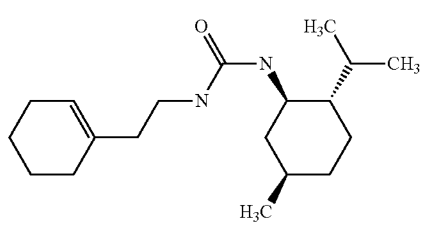 [SMILES: CC(C)[C@@H]1CC[C@@H](C)C[C@H]1NC(=O)NCCC1=CCCCC1] | | 2-cyclohex-1-enyl ethyl | 84 |
| 1885 | 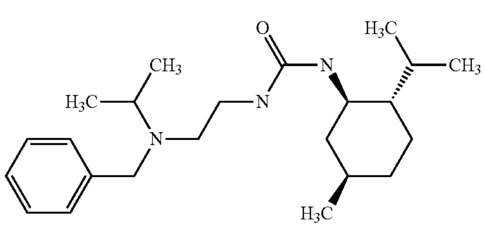 [SMILES: CC(C)[C@@H]1CC[C@@H](C)C[C@H]1NC(=O)NCCN(Cc1ccccc1)C(C)C] | | 2-(N-isopropyl, N-Phenylethyl) amino ethyl | 97 |

TABLE 2-continued

Exemplary Formula VIII Trp-p8 Antagonists of Formula IV Agonist Compounds

| Ref. No.: | Chemical Structure | $R^{23}/R^{24}$ | $R^{24}$ | Relative Viability (%) at 10 μM |
|---|---|---|---|---|
| 1918 | 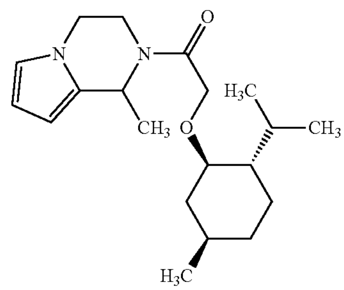 [SMILES: CC(C)[C@@H]1CC[C@@H](C)C[C@H]1OCC(=O)N1CCn2cccc2C1C] | 1-methyl-1,2,3,4-tetrahydro-pyrrolo[1,2-a]pyrazine | | 94 |
| 1920 | 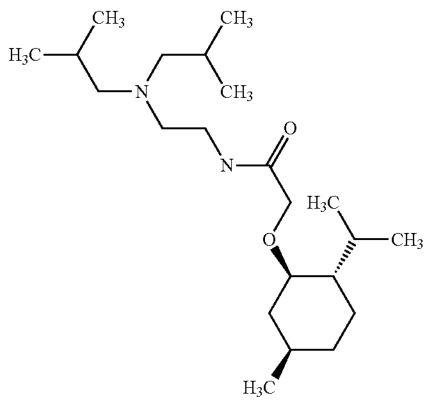 [SMILES: CC(C)CN(CCNC(=O)CO[C@@H]1C[C@H](C)CC[C@H]1C(C)C)CC(C)C] | | | 81 |
| 1923 | 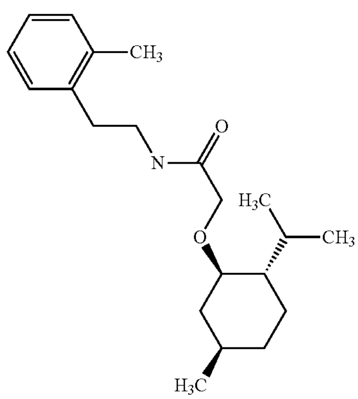 [SMILES: Cc1ccccc1CCNC(=O)CO[C@@H]1C[C@H](C)CC[C@H]1C(C)C] | | | 116 |
| 1925 | 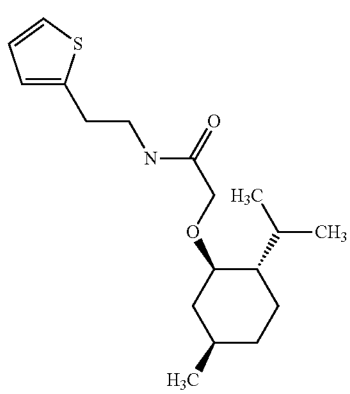 [SMILES: CC(C)[C@@H]1CC[C@@H](C)C[C@H]1OCC(=O)NCCc1cccs1] | | | 94 |

TABLE 2-continued

Exemplary Formula VIII Trp-p8 Antagonists of Formula IV Agonist Compounds

| Ref. No.: | Chemical Structure | $R^{23}/R^{24}$ | $R^{24}$ | Relative Viability (%) at 10 μM |
|---|---|---|---|---|
| 1937 | 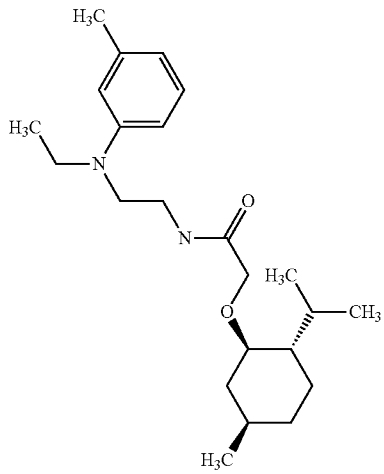 [SMILES: CCN(CCNC(=O)CO[C@@H]1C[C@H](C)CC[C@H]1C(C)C)c1cccc(C)c1] | | | 101 |
| 1940 | 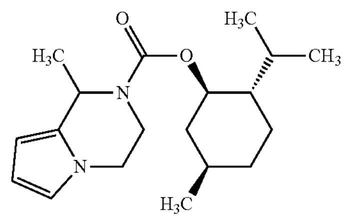 [SMILES: CC(C)[C@@H]1CC[C@@H](C)C[C@H]1OC(=O)N1CCn2cccc2C1C] | 1-methyl-1,2,3,4-tetrahydro-pyrrolo[1,2-a]pyrazine | | 110 |
| 1941 | 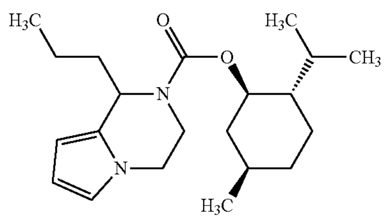 [SMILES: CCCC1c2cccn2CCN1C(=O)O[C@@H]1C[C@H](C)CC[C@H]1C(C)C] | 1-Propyl-1,2,3,4-tetrahydro-pyrrolo[1,2-a]pyrazine | | 98 |
| 1996 | 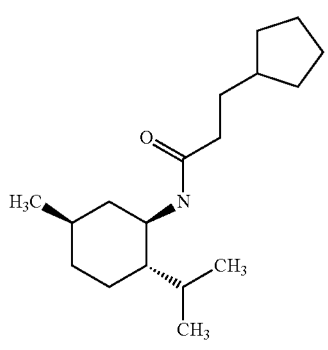 [SMILES: CC(C)[C@@H]1CC[C@@H](C)C[C@H]1NC(=O)CCC1CCCC1] | | 2-cyclopentylethyl | 89 |
| 2013 | 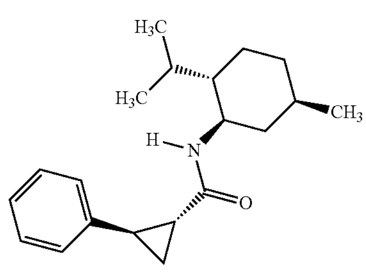 [SMILES: CC(C)[C@@H]1CC[C@@H](C)C[C@H]1NC(=O)[C@@H]1C[C@H]1c1ccccc1] | | 2-Phenylcyclopropyl | 95 |

TABLE 2-continued

Exemplary Formula VIII Trp-p8 Antagonists of Formula IV Agonist Compounds

| Ref. No.: | Chemical Structure | $R^{23}/R^{24}$ | $R^{24}$ | Relative Viability (%) at 10 µM |
|---|---|---|---|---|
| 2018 | 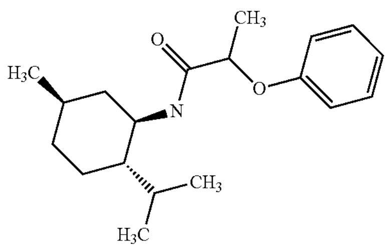 [SMILES: CC(Oc1ccccc1)C(=O)N[C@@H]1C[C@H](C)CC[C@H]1C(C)C] | | 1-phenoxyethyl | 103 |
| 2044 | 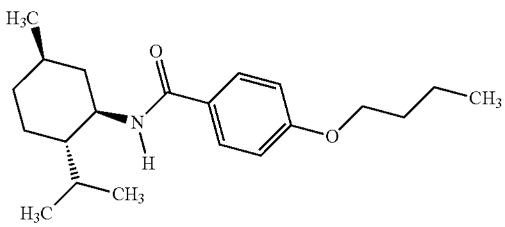 [SMILES: CCCCOc1ccc(C(=O)N[C@@H]2C[C@H](C)CC[C@H]2C(C)C)cc1] | | 4-butyloxyphenyl | 94 |
| 2045 | 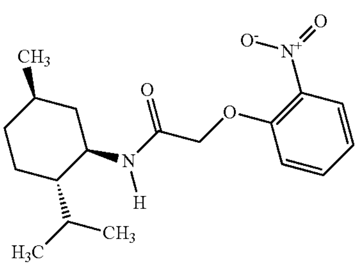 [SMILES: CC(C)[C@@H]1CC[C@@H](C)C[C@H]1NC(=O)COc1ccccc1[N+](=O)[O-]] | | (2-nitrophenoxy)methyl | 191 |
| 2046 | 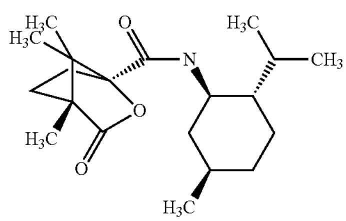 [SMILES: CC(C)[C@@H]1CC[C@@H](C)C[C@H]1NC(=O)[C@@]12CC[C@@](C)(C(=O)O1)C2(C)C] | | 4,7,7-trimethyl-2-oxa-bicyclo[2.2.1]heptan-3-one | 89 |
| 2067 | 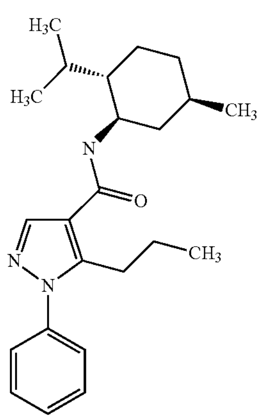 [SMILES: CCCc1c(C(=O)N[C@@H]2C[C@H](C)CC[C@H]2C(C)C)cnn1-c1ccccc1] | | C-(1-Phenyl-5-propyl-1H-pyrazol-4-yl)-methyl | 105 |

TABLE 2-continued

Exemplary Formula VIII Trp-p8 Antagonists of Formula IV Agonist Compounds

| Ref. No.: | Chemical Structure | $R^{23}/R^{24}$ | $R^{24}$ | Relative Viability (%) at 10 μM |
|---|---|---|---|---|
| 2291 | 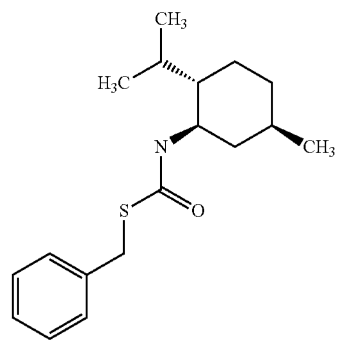 [SMILES: CC(C)[C@@H]1CC[C@@H](C)C[C@H]1NC(=O)SCc1ccccc1] | | Benzyl | 87 |
| 2306 | 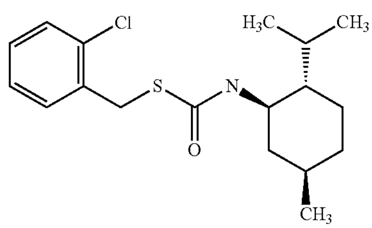 [SMILES: CC(C)[C@@H]1CC[C@@H](C)C[C@H]1NC(=O)SCc1ccccc1Cl] | | 2-chlorobenzyl | 92 |
| 2639 | 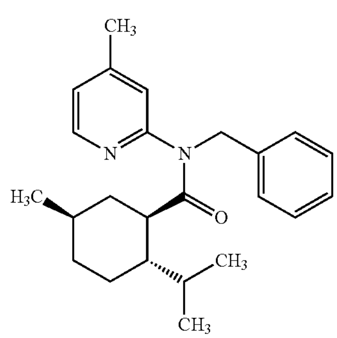 [SMILES: Cc1ccnc(N(Cc2ccccc2)C(=O)[C@@H]2C[C@H](C)CC[C@H]2C(C)C)c1] | | benzyl; R2 = 2-(4-methyl)pyridyl | 102 |
| 2676 | 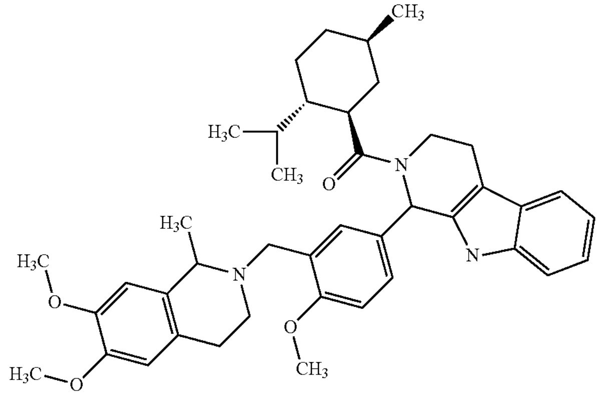 [SMILES: COc1ccc(C2c3[nH]c4ccccc4c3CCN2C(=O)[C@@H]2C[C@H](C)CC[C@H]2C(C)C)cc1CN1CCc2cc(OC)c(OC)cc2C1C] | | 1-[3-(6,7-Dimethoxy-1-methyl-3,4-dihydro-1H-isoquinolin-2-ylmethyl)-4-methoxy-phenyl]-2,3,4,9-tetra-hydro-1H-b-carboline | 83 |

TABLE 2-continued

Exemplary Formula VIII Trp-p8 Antagonists of Formula IV Agonist Compounds

| Ref. No.: | Chemical Structure | $R^{23}/R^{24}$ | $R^{24}$ | Relative Viability (%) at 10 μM |
|---|---|---|---|---|
| 2777 | 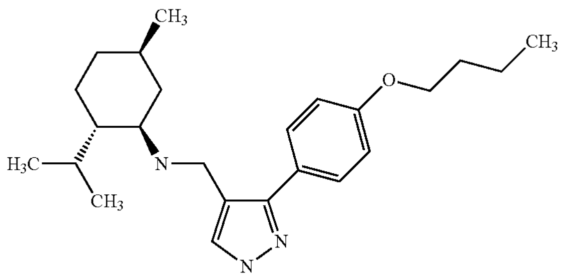 [SMILES: CCCCOc1ccc(-c2n[nH]cc2CN[C@@H]2C[C@H](C)CC[C@H]2C(C)C)cc1] | | C-[3-(4-Butoxy-phenyl)-1H-pyrazol-4-yl]-methyl | 83 |
| 2865 | 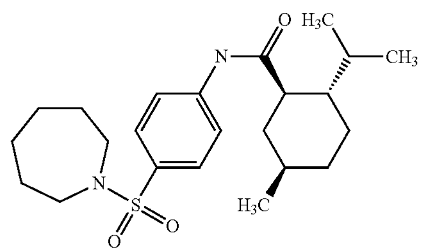 [SMILES: CC(C)[C@@H]1CC[C@@H](C)C[C@H]1C(=O)Nc1ccc(S(=O)(=O)N2CCCCCC2)cc1] | | 4-(Azepane-1-sulfonyl)-phenyl | 91 |
| 3026 | 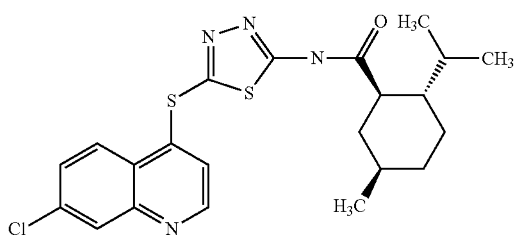 [SMILES: CC(C)[C@@H]1CC[C@@H](C)C[C@H]1C(=O)Nc1nnc(Sc2ccnc3cc(Cl)ccc23)s1] | | 5-(7-Chloro-quinolin-4-ylsulfanyl)-[1,3,4]thiadiazol-2-yl | 86 |
| 2131 | 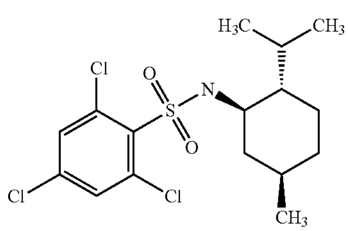 [SMILES: CC(C)[C@@H]1CC[C@@H](C)C[C@H]1NS(=O)(=O)c1c(Cl)cc(Cl)cc1Cl] | | 2,4,6-trichlorophenyl | 59 |
| 2134 | 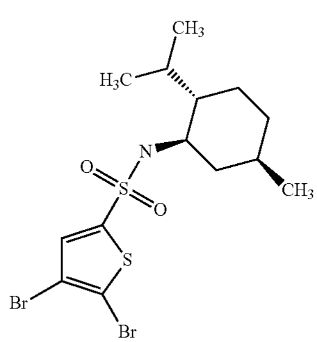 [SMILES: CC(C)[C@@H]1CC[C@@H](C)C[C@H]1NS(=O)(=O)c1cc(Br)c(Br)s1] | | 4,5-dibromothiophen-2-yl | 63 |

TABLE 2-continued

Exemplary Formula VIII Trp-p8 Antagonists of Formula IV Agonist Compounds

| Ref. No.: | Chemical Structure | $R^{23}/R^{24}$ | $R^{24}$ | Relative Viability (%) at 10 μM |
|---|---|---|---|---|
| 2710 | 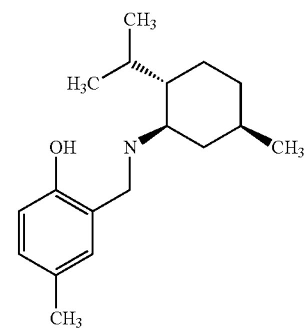 [SMILES: Cc1ccc(O)c(CN[C@@H]2C[C@H](C)CC[C@H]2C(C)C)c1] | | 2-hydroxy-5-methylphenyl | 70 |
| 2745 | 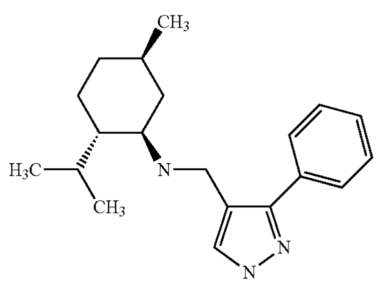 [SMILES: CC(C)[C@@H]1CC[C@@H](C)C[C@H]1NCc1c[nH]nc1-c1ccccc1] | | 3-phenyl-1H-pyrazol-4-yl | 62 |
| 2752 | 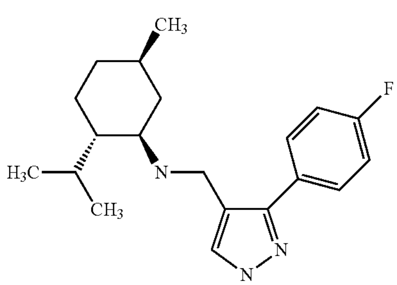 [SMILES: CC(C)[C@@H]1CC[C@@H](C)C[C@H]1NCc1c[nH]nc1-c1ccc(F)cc1] | | 3-(4-fluorophenyl)-1H-pyrazol-4-yl | 65 |
| 2754 | 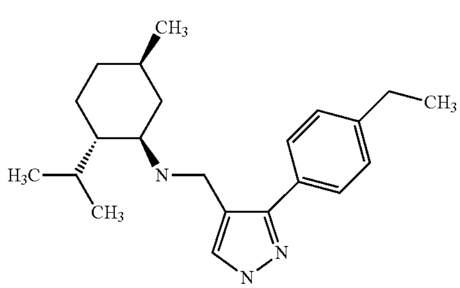 [SMILES: CCc1ccc(-c2n[nH]cc2CN[C@@H]2C[C@H](C)CC[C@H]2C(C)C)cc1] | | 3-(4-ethylphenyl)-1H-pyrazol-4-yl | 74 |

TABLE 3

Exemplary Formula VII Trp-p8 Antagonists of Formula II Agonist Compounds

| Ref. No. | Chemical Structure | R¹⁷ | R¹⁸ | R¹⁹/R²⁰ | R²¹ | Rel. Viab. (%) at 10 μM |
|---|---|---|---|---|---|---|
| 13 | 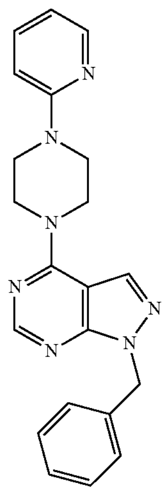 [SMILES: c1ccc(Cn2ncc3c(N4CCN(c5ccccn5)CC4)ncnc32)cc1] | 2-Pyridyl | 1-Benzyl-1H-pyrazolo[3,4-d]pyrimidin-4-yl | | H | 91 |
| 27 | 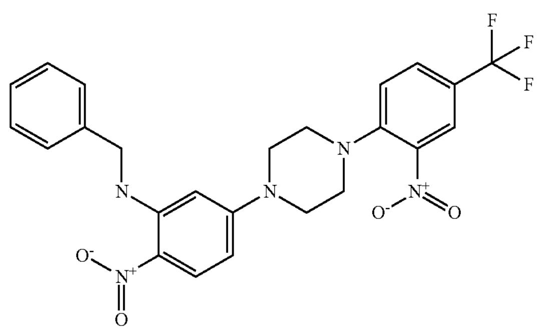 [SMILES: O=[N+]([O-])c1ccc(N2CCN(c3ccc(C(F)(F)F)cc3[N+](=O)[O-])CC2)cc1NCc1ccccc1] | 2-Nitro-4-trifluoromethylphenyl | 3-benzyl-amino-2-nitrophenyl | | H | 87 |
| 34 | 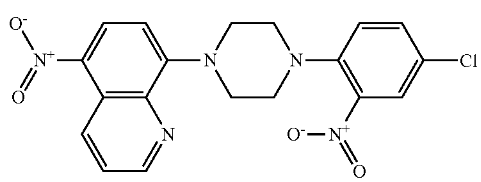 [SMILES: O=[N+]([O-])c1cc(Cl)ccc1N1CCN(c2ccc([N+](=O)[O-])c3cccnc23)CC1] | 2-nitro-4-chlorophenyl | 5-Nitroquinolin-8-yl | | H | 82 |
| 36 | 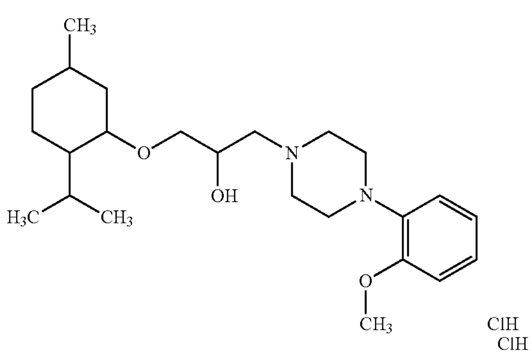 [SMILES: COc1ccccc1N1CCN(CC(O)COC2CC(C)CCC2C(C)C)CC1 ; Cl ; Cl] | 2-methoxyphenyl | 1-yl-3-(2-isopropyl-5-methylcyclohexyloxy)-propan-2-ol | | H | 87 |

TABLE 3-continued

Exemplary Formula VII Trp-p8 Antagonists of Formula II Agonist Compounds

| Ref. No. | Chemical Structure | $R^{17}$ | $R^{18}$ | $R^{19}/R^{20}$ | $R^{21}$ | Rel. Viab. (%) at 10 μM |
|---|---|---|---|---|---|---|
| 51 | 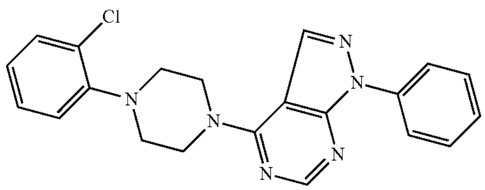 [SMILES: Clc1ccccc1N1CCN(c2ncnc3c2cnn3-c2ccccc2)CC1] | 2-chloro-phenyl | 1-Phenyl-1H-pyrazolo[3,4-d]pyrimidin-4-yl | H | | 100 |
| 67 | 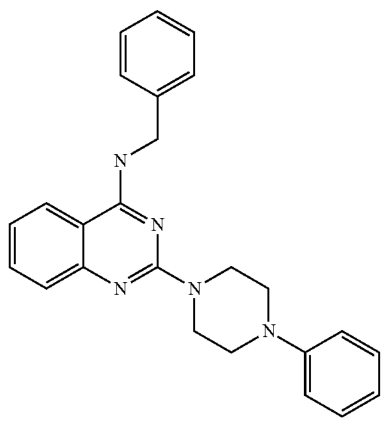 [SMILES: c1ccc(CNc2nc(N3CCN(c4ccccc4)CC3)nc3ccccc23)cc1] | phenyl | Benzyl-2-methyl-quinazolin-4-yl | H | | 102 |
| 69 | 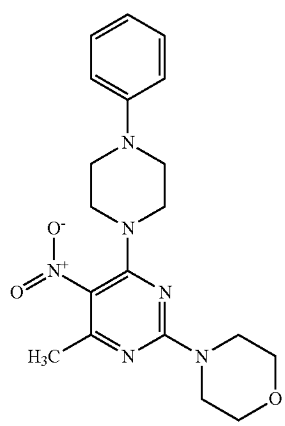 [SMILES: Cc1nc(N2CCOCC2)nc(N2CCN(c3ccccc3)CC2)c1[N+](=O)[O-]] | phenyl | 3-Methyl-5-morpholin-4-yl-2-nitro-phenyl | H | | 106 |
| 74 | 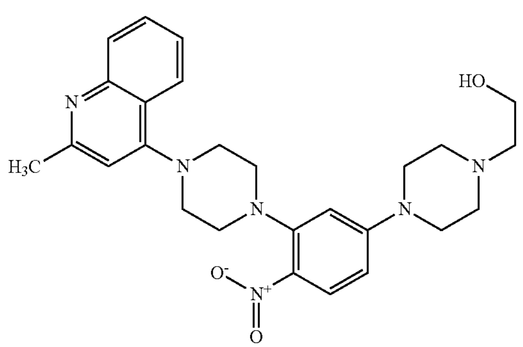 [SMILES: Cc1cc(N2CCN(c3cc(N4CCN(CCO)CC4)ccc3[N+](=O)[O-])CC2)c2ccccc2n1] | 2-methyl-quinolin-3-yl | 2-nitro-5-piperazin-1-yl-ethanol | H | | 81 |

TABLE 3-continued

Exemplary Formula VII Trp-p8 Antagonists of Formula II Agonist Compounds

| Ref. No. | Chemical Structure | $R^{17}$ | $R^{18}$ | $R^{19}/R^{20}$ | $R^{21}$ | Rel. Viab. (%) at 10 μM |
|---|---|---|---|---|---|---|
| 93 | 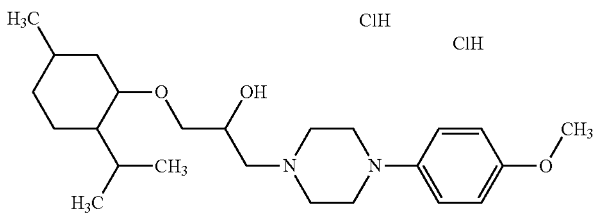 [SMILES: COc1ccc(N2CCN(CC(O)COC3CC(C)CCC3C(C)C)CC2)cc1 ; Cl ; Cl] | 4-methoxy-phenyl | 1-yl-3-(2-iso-propyl-5-methyl-cyclohexyl-oxy)-propan-2-ol | H | | 111 |
| 103 | 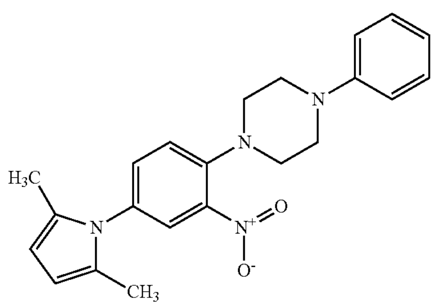 [SMILES: Cc1ccc(C)n1-c1ccc(N2CCN(c3ccccc3)CC2)c([N+](=O)[O-])c1] | phenyl | 4-(2,5-Di-methyl-pyrrol-1-yl)-2-nitro-phenyl | H | | 99 |
| 107 | 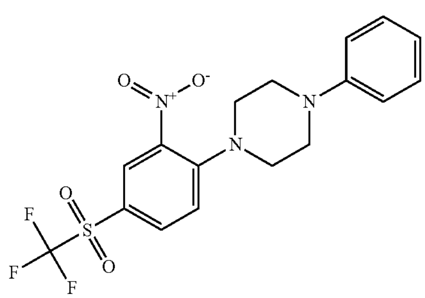 [SMILES: O=[N+]([O-])c1cc(S(=O)(=O)C(F)(F)F)ccc1N1CCN(c2ccccc2)CC1] | phenyl | 2-nitro-3-tri-fluoro-methane-sulfonyl-phenyl | H | | 98 |
| 159 | 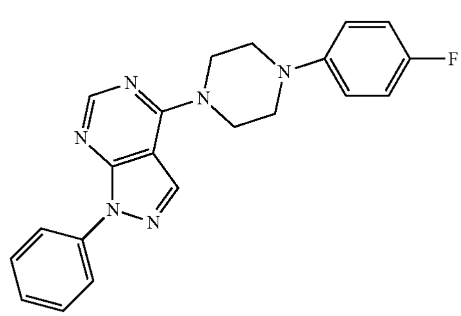 [SMILES: Fc1ccc(N2CCN(c3ncnc4c3cnn4-c3ccccc3)CC2)cc1] | 4-fluorophenyl | 1-Phenyl-1H-pyra-zolo[3,4-d]pyrim-idin-4-yl | H | | 95 |
| 711 | 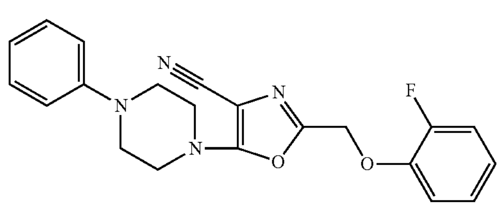 [SMILES: N#Cc1nc(COc2ccccc2F)oc1N1CCN(c2ccccc2)CC1] | phenyl | 2-(2-Fluoro-phenoxy-methyl)-2-cyano oxazolyl | H | | 94 |

TABLE 3-continued

Exemplary Formula VII Trp-p8 Antagonists of Formula II Agonist Compounds

| Ref. No. | Chemical Structure | R17 | R18 | R19/ R20 | R21 | Rel. Viab. (%) at 10 μM |
|---|---|---|---|---|---|---|
| 809 | 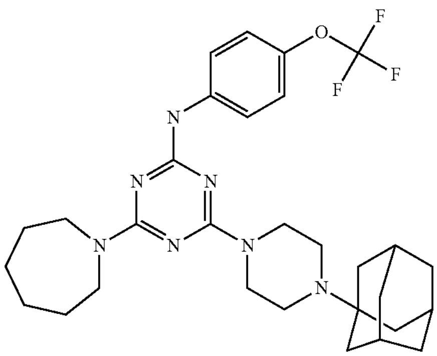 [SMILES: FC(F)(F)Oc1ccc(Nc2nc(N3CCCCCC3)nc(N3CCN(C45CC6CC(CC(C6)C4)C5)CC3)n2)cc1] | 3-azepan1-yl-5-(4-trifluoro-methoxy)phenyl-amino[1,3,5]triazyl | adamantyl | H | | 89 |
| 812 | 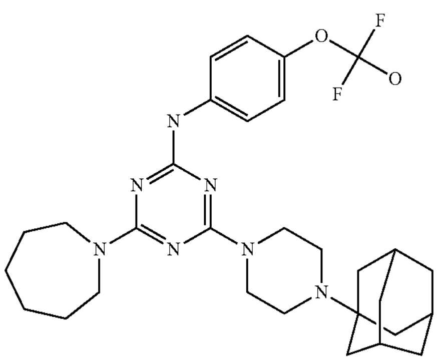 [SMILES: OC(F)(F)Oc1ccc(Nc2nc(N3CCCCCC3)nc(N3CCN(C45CC6CC(CC(C6)C4)C5)CC3)n2)cc1] | 3-azepan1-yl-5-(4-trifluoro-methoxy)phenyl-amino[1,3,5]triazyl | adamantyl | H | | 99 |
| 881 | 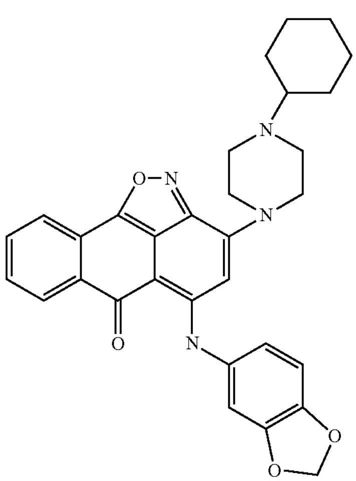 [SMILES: O=C1c2ccccc2-c2onc3c(N4CCN(C5CCCCC5)CC4)cc(Nc4ccc5c(c4)OCO5)c1c23] | cyclohexyl | 5-(Benzo[1,3]dioxol-5-ylamino)-10b,10c-dihydro-anthra[1,9-cd]isoxazol-6-one-yl | H | | 82 |

TABLE 3-continued

Exemplary Formula VII Trp-p8 Antagonists of Formula II Agonist Compounds

| Ref. No. | Chemical Structure | R$^{17}$ | R$^{18}$ | R$^{19}$/ R$^{20}$ | R$^{21}$ | Rel. Viab. (%) at 10 µM |
|---|---|---|---|---|---|---|
| 882 | 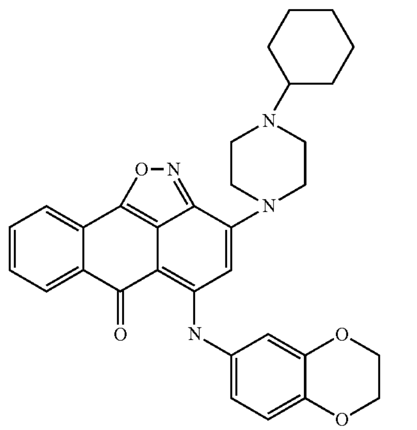 [SMILES: O=C1c2ccccc2-c2onc3c(N4CCN(C5CCCCC5)CC4)cc(Nc4ccc5c(c4)OCCO5)c1c23] | cyclohexyl | 5-(Benzo[1,3]dioxol-5-ylamino)-10b,10c-dihydro-anthra[1,9-cd]iso-xazol-6-one-yl | H | | 86 |
| 1019 | 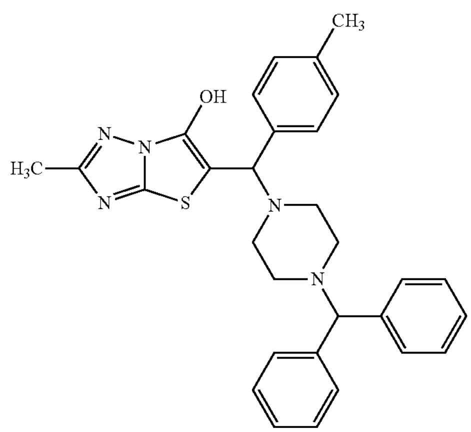 [SMILES: Cc1ccc(C(c2sc3nc(C)nn3c2O)N2CCN(C(c3ccccc3)c3ccccc3)CC2)cc1] | diphenyl-methyl | 2-Methyl-thiazolo[3,2-b][1,2,4]triazol-6-ol 4-methyl-phenyl methyl | H | | 87 |
| 1021 | 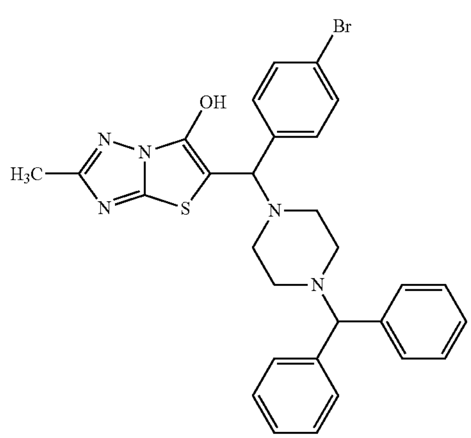 [SMILES: Cc1nc2sc(C(c3ccc(Br)cc3)N3CCN(C(c4ccccc4)c4ccccc4)CC3)c(O)n2n1] | diphenyl-methyl | 2-Methyl-thiazolo[3,2-b][1,2,4]triazol-6-ol 4-methyl-phenyl methyl | H | | 92 |

TABLE 3-continued

Exemplary Formula VII Trp-p8 Antagonists of Formula II Agonist Compounds

| Ref. No. | Chemical Structure | R[17] | R[18] | R[19]/ R[20] | R[21] | Rel. Viab. (%) at 10 μM |
|---|---|---|---|---|---|---|
| 1026 | 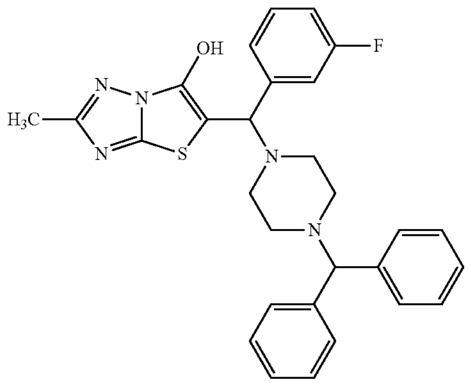 | diphenyl-methyl | 2-Methyl-thiazolo[3,2-b][1,2,4]triazol-6-ol 4-methyl-phenyl methyl | H | | 92 |
| 1027 | 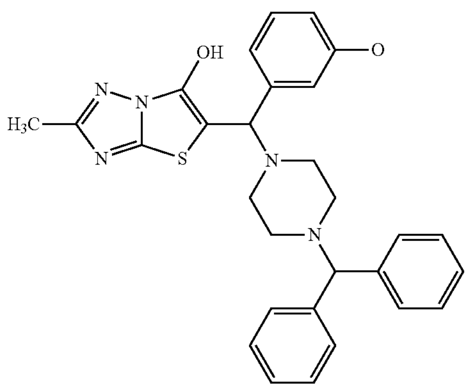 [SMILES: Cc1nc2sc(C(c3cccc(O)c3)N3CCN(C(c4ccccc4)c4ccccc4)CC3)c(O)n2n1] | diphenyl-methyl | 2-Methyl-thiazolo[3,2-b][1,2,4]triazol-6-ol 4-methyl-phenyl methyl | H | | 84 |
| 1028 | 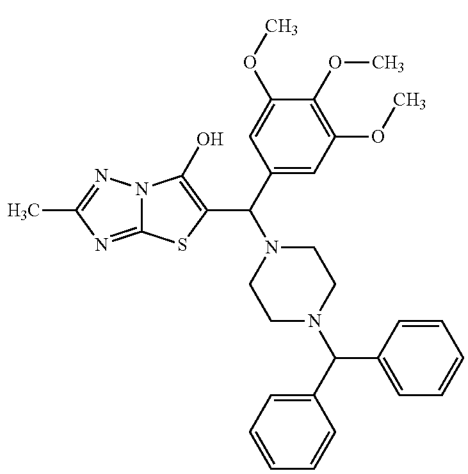 [SMILES: COc1cc(C(c2sc3nc(C)nn3c2O)N2CCN(C(c3ccccc3)c3ccccc3)CC2)cc(OC)c1OC] | diphenyl-methyl | 2-Methyl-thiazolo[3,2-b][1,2,4]triazol-6-ol 4-methyl-phenyl methyl | H | | 85 |

TABLE 3-continued

Exemplary Formula VII Trp-p8 Antagonists of Formula II Agonist Compounds

| Ref. No. | Chemical Structure | R¹⁷ | R¹⁸ | R¹⁹/ R²⁰ | R²¹ | Rel. Viab. (%) at 10 μM |
|---|---|---|---|---|---|---|
| 1039 | 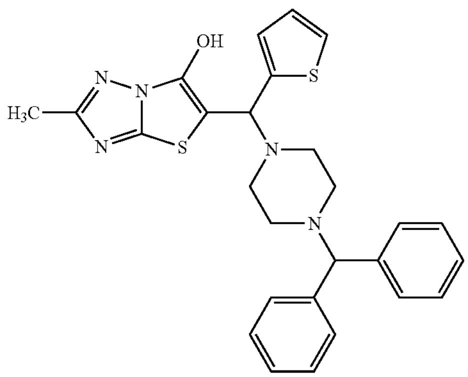 [SMILES: Cc1nc2sc(C(c3cccs3)N3CCN(C(c4ccccc4)c4ccccc4)CC3)c(O)n2n1] | diphenyl-methyl | 2-Methyl-thiazolo[3,2-b][1,2,4]triazol-6-ol 4-methyl-phenyl methyl | H | | 84 |
| 1069 | 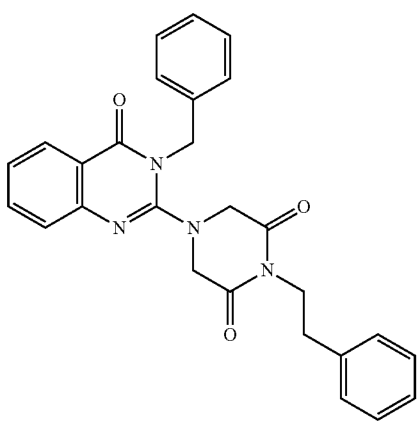 [SMILES: O=C1CN(c2nc3ccccc3c(=O)n2Cc2ccccc2)CC(=O)N1CCc1ccccc1] | 2-phenylethyl | 3-benzyl-3H-quin-azolin-4-one-2-yl | O | | 86 |
| 1262 | 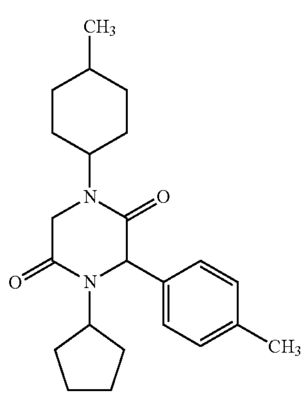 [SMILES: Cc1ccc(C2C(=O)N(C3CCC(C)CC3)CC(=O)N2C2CCCC2)cc1] | 4-hydroxy-cyclohexyl | cyclopentyl | O | 4-methyl-phenyl | 86 |

TABLE 3-continued

Exemplary Formula VII Trp-p8 Antagonists of Formula II Agonist Compounds

| Ref. No. | Chemical Structure | R$^{17}$ | R$^{18}$ | R$^{19}$/R$^{20}$ | R$^{21}$ | Rel. Viab. (%) at 10 μM |
|---|---|---|---|---|---|---|
| 1280 | 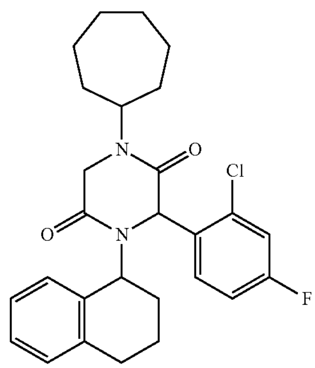 [SMILES: O=C1C(c2ccc(F)cc2Cl)N(C2CCCc3ccccc32)C(=O)CN1C1CCCCCC1] | cycloheptyl | tetrahydro-naphthyl | O | 2-chloro-4-fluoro-phenyl | 87 |
| 1283 | 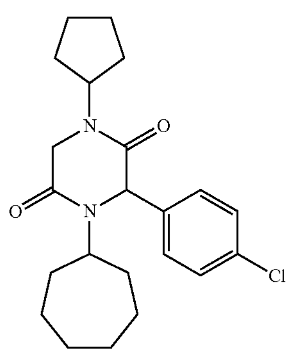 [SMILES: O=C1C(c2ccc(Cl)cc2)N(C2CCCCCC2)C(=O)CN1C1CCCC1] | cyclopentyl | cyclooctyl | O | 4-chloro-phenyl | 100 |
| 1284 | 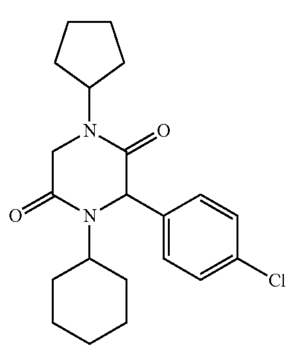 [SMILES: O=C1C(c2ccc(Cl)cc2)N(C2CCCCC2)C(=O)CN1C1CCCC1] | cyclopentyl | cyclohexyl | O | 4-chloro-phenyl | 95 |

TABLE 3-continued

Exemplary Formula VII Trp-p8 Antagonists of Formula II Agonist Compounds

| Ref. No. | Chemical Structure | $R^{17}$ | $R^{18}$ | $R^{19}/R^{20}$ | $R^{21}$ | Rel. Viab. (%) at 10 μM |
|---|---|---|---|---|---|---|
| 1313 | 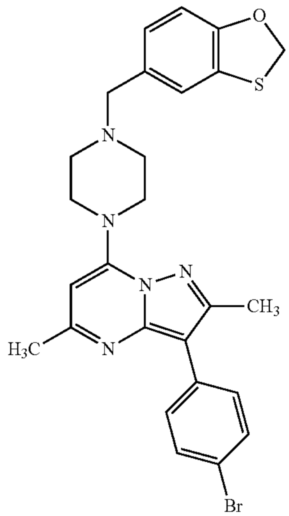 [SMILES: Cc1cc(N2CCN(Cc3ccc4c(c3)SCO4)CC2)n2nc(C)c(-c3ccc(Br)cc3)c2n1] | C-Benzo[1,3]dioxol-5-yl-methyl | C-[3-(4-Chlorophenyl)-2,5-dimethyl-pyrazolo[1,5-a]pyrimidin-7-yl]-methyl | H | | 92 |
| 1323 | 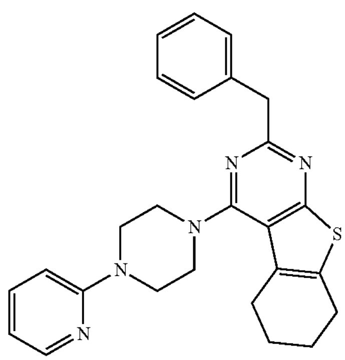 [SMILES: c1ccc(Cc2nc(N3CCN(c4ccccn4)CC3)c3c4c(sc3n2)CCCC4)cc1] | 2-Pyridyl | C-(2-Benzyl-5,6,7,8-tetrahydro-benzo[4,5]thieno[2,3-d]pyrimidin-4-yl)-methyl | H | | 88 |
| 2496 | 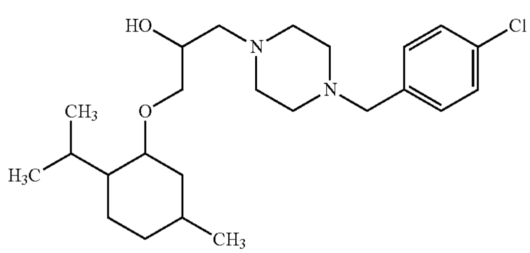 [SMILES: CC1CCC(C(C)C)C(OCC(O)CN2CCN(Cc3ccc(Cl)cc3)CC2)C1] | 4-chloro-benzyl | 1-yl-3-(2-isopropyl-5-methyl-cyclo-hexyl-oxy)-propan-2-ol | H | | 82 |

Example 11

In Vitro Screen using a Calcium Flux Assay for Trp-p8 Antagonist Compounds Based upon their Abilities to Suppress the Calcium Influx Induced by Trp-p8 Agonists in CHO/Trp-p8 Cells This example discloses an in vitro assay system employed to further screen and characterize candidate Trp-p8 antagonists.

Figure 5:
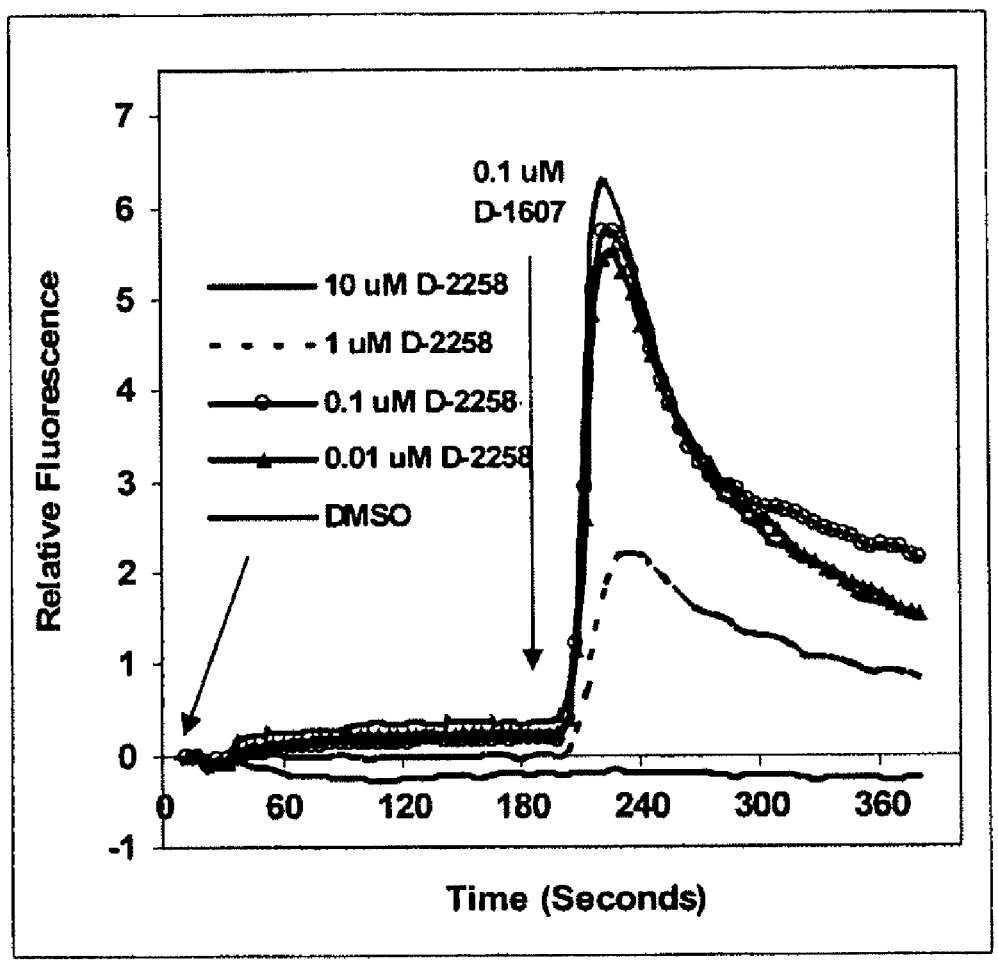
FIG. 5 is a graph depicting the screening and characterization of Trp-p8 antagonists by the calcium flux assay performed at 37° C. CHO/Trp-p8 cells were loaded with the calcium indicator dye, Fura-2; and the increase in intracellular calcium in response to compounds was determined by the increase in fluorescence. Fura-2 dye loaded CHO/Trp-p8 cells were exposed to 1% DMSO or D-2258, at different concentrations, in 1% DMSO at 37° C. Three minutes later, D-1607 was added to the cells. When cells were exposed to effective concentrations of the antagonist, D-2258, their ability to respond to the agonist D-1607 was significantly reduced or eliminated altogether.

Trp-p8 antagonists were also screened and characterized using a calcium flux assay at 37° C. as described in Example 8 with the following two distinctions: (1) the compound was pre-mixed with the control agonist or only the control agonist is added to the cells and suppression of the response to the agonist is a measure of the potency of the compound as an antagonist and (2) the compound, at different concentrations, was added to the cells followed by addition of the control agonist after 2-3 minutes and the suppression of response induced by agonist was a measure of potency of the compound as an antagonist. Exemplary results are presented in FIG. 5.

Example 12

An Animal Model System for Assaying the In vivo Efficacy of Candidate Trp-p8 Agonists and Antagonists for the Treatment of Cancer This Example provides an animal model system suitable for determining the in vivo efficacy of candidate Trp-p8 modulators—including both agonists and antagonists.

Human prostate cancer xenografts expressing Trp-P8 (from Dr. Robert Vessella's lab in University of Washington—as assessed by in situ hybridization and immunohistochemistry using a protein specific rabbit polyclonal antibody, T-904) as well as CHO (Chinese Hamster Ovary) and EL-4 (Mouse Thymoma) cell lines were engineered to express Trp-P8 and used to establish tumor models in mice. Trp-P8 expression in these transfectants was confirmed by western blots and immunofluorescence using a Trp-p8 specific antibody (GS 2.20) as well as by response to known agonists in a calcium influx functional assay. In addition, these transfected cell lines were susceptible to killing by Trp-p8 agonists as evident from the ATP viability and apoptosis assays (as described herein in Examples 7 and 8).

A tumor model in mice was established by subcutaneously injecting CHO/Trp-P8 cells in SCID mice. Trp-p8 expression in tumors excised from these mice was confirmed by RT-PCR and western blot analysis. Further tumor model development is carried out using the human prostate cancer xenografts described above in athymic nude or SCID mice and using an EL4/Trp-p8 transfectant in normal mice. Prostate xenografts from other sources and other cell lines that may be engineered to express Trp-p8 are also potential candidates for building more model systems.

Based on results from in vitro and in vivo evaluations, a set of trp-p8 agonists will be chosen to determine efficacy in mice. The in vitro evaluations would include potency in cell killing assay, aqueous solubility, plasma binding study and metabolic stability (potential for a compound to be metabolized by liver as determined by using hepatocytes and/or mouse microsomes). The in vivo evaluations would include pharmacokinetics and toxicity studies. The chosen compounds will be administered to mice with Trp-p8 expressing tumors by different routes [oral, intravenous, intraperitoneal, subcutaneous, intramuscular]. Tumor reduction and survival of these mice will be evaluated at different dosages of these compounds. The compound most effective in fighting tumor will be chosen for further investigations Although the present invention has been described in some detail by way of illustration and example for purposes of clarity of understanding, changes and modifications can be carried out without departing from the scope of the invention which is intended to be limited only by the scope of the appended claims.

We claim:

1. A method for decreasing the viability of a Trp-p8 expressing cell, said method comprising the step of contacting said cell with a compound of Formula IV

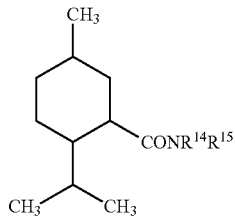

IV and pharmaceutically acceptable salts thereof, wherein
$R^{14}$ and $R^{15}$ together form a cyclic or heterocyclic group of up to 25 carbons and including the nitrogen atom.

2. The method of claim 1 wherein said cyclic or heterocyclic group is selected from the group consisting of 3-phenyl-piperidin-1-yl, 3-phenyl-pyrrolidin-1-yl, 6,7-dimethoxy-1-methyl-3,4-dihydro-1H-isoquinolin-2-yl, and 4-pyrimidin-2-yl-piperazin-1-yl.

3. A method for inducing apoptosis and/or necrosis in a cell expressing Trp-p8, said method comprising the step of administering to said cell a compound of Formula IV

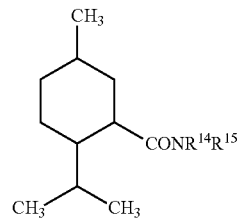

IV and pharmaceutically acceptable salts thereof, wherein
$R^{14}$ and $R^{15}$ together form a cyclic or heterocyclic group of up to 25 carbons and including the nitrogen atom.

4. A method for treating a disease associated with Trp-p8 expression, said method comprising the step of administering to a mammal an efficacious amount of a composition comprising a compound having the formula:

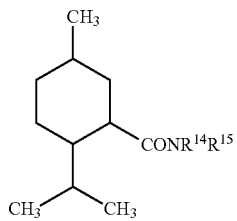

IV and pharmaceutically acceptable salts thereof, in combination with a pharmaceutically acceptable carrier or diluent, wherein $R^{14}$ and $R^{15}$ together form a cyclic or heterocyclic group of up to 25 carbons and including the nitrogen atom.

5. The method of claim 4 wherein said cyclic or heterocyclic group is selected from the group consisting of 3-phenyl-piperidin-1-yl, 3-phenyl-pyrrolidin-1-yl, 6,7-dimethoxy-1-methyl-3,4-dihydro-1H-isoquinolin-2-yl, and 4-pyrimidin-2-yl-piperazin-1-yl.

* * * * *